US008847006B2

(12) United States Patent
Jenkinson et al.

(10) Patent No.: US 8,847,006 B2
(45) Date of Patent: Sep. 30, 2014

(54) UTILITY OF SNP MARKERS ASSOCIATED WITH MAJOR SOYBEAN PLANT MATURITY AND GROWTH HABIT GENOMIC REGIONS

(75) Inventors: Jonathan Jenkinson, Ames, IA (US); John Tamulonis, Nevada, IA (US); James Narvel, Middletown, DE (US); Kenneth Gruys, Davis, CA (US); Henry Valentin, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1899 days.

(21) Appl. No.: 12/078,173

(22) Filed: Mar. 27, 2008

(65) Prior Publication Data

US 2008/0256660 A1 Oct. 16, 2008

Related U.S. Application Data

(60) Provisional application No. 60/920,531, filed on Mar. 28, 2007, provisional application No. 61/001,049, filed on Oct. 31, 2007.

(51) Int. Cl.
*A01H 1/04* (2006.01)
*C12N 15/10* (2006.01)
*C12Q 1/68* (2006.01)

(52) U.S. Cl.
CPC ............... *C12Q 1/6895* (2013.01); *A01H 1/04* (2013.01)
USPC .......................................... 800/267; 800/312

(58) Field of Classification Search
None
See application file for complete search history.

(56) References Cited

U.S. PATENT DOCUMENTS

| | | | |
|---|---|---|---|
| 4,563,417 A | 1/1986 | Albarella et al. | |
| 4,582,788 A | 4/1986 | Erlich | |
| 4,582,789 A | 4/1986 | Sheldon, III et al. | |
| 4,683,194 A | 7/1987 | Saiki et al. | |
| 4,683,202 A | 7/1987 | Mullis | |
| 4,992,375 A | 2/1991 | Wright | |
| 5,015,580 A | 5/1991 | Christou et al. | |
| 5,024,944 A | 6/1991 | Collins et al. | |
| 5,416,011 A | 5/1995 | Hinchee et al. | |
| 5,637,785 A | 6/1997 | Weigel | |
| 5,723,761 A | 3/1998 | Voelker et al. | |
| 5,952,544 A | 9/1999 | Browse et al. | |
| 5,955,329 A | 9/1999 | Yuan et al. | |
| 5,955,650 A | 9/1999 | Hitz | |
| 6,140,085 A | 10/2000 | Dean et al. | |
| 6,184,440 B1 | 2/2001 | Shoseyov et al. | |
| 6,331,664 B1 | 12/2001 | Rubin-Wilson et al. | |
| 6,486,383 B1 | 11/2002 | Burrell et al. | |
| 6,774,284 B1 | 8/2004 | Thompson et al. | |
| 7,002,058 B2 | 2/2006 | Martinell et al. | |
| 7,067,722 B2 | 6/2006 | Fillatti | |
| 7,951,998 B2 * | 5/2011 | Baley et al. ................... 800/312 |
| 2004/0006792 A1 | 1/2004 | Fillatti et al. | |
| 2004/0172682 A1 | 9/2004 | Kinney et al. | |
| 2006/0042527 A1 | 3/2006 | Deppermann | |
| 2006/0156435 A1 | 7/2006 | Ursin et al. | |
| 2006/0288444 A1 | 12/2006 | McCarroll et al. | |
| 2010/0293673 A1 * | 11/2010 | Bull ............................. 800/301 |

FOREIGN PATENT DOCUMENTS

| | | |
|---|---|---|
| AU | 715002 B2 | 6/1996 |
| EP | 0 119 448 A1 | 9/1984 |
| EP | 0 201 184 A2 | 12/1986 |
| EP | 0 237 362 A1 | 9/1987 |
| EP | 0 258 017 A2 | 3/1988 |
| WO | WO 96/17069 A2 | 6/1996 |
| WO | WO 2005/021761 A1 | 3/2005 |
| WO | WO-2008/021413 A1 * | 2/2008 |

OTHER PUBLICATIONS

Savoy et al. Agronomy Journal 84: 394-398 (1992).*
PI 462312 (Ankur) deposited 1981.*
Byron et al., "Comparison of Three Selection Procedures for Development of Early-Maturing Soybean Lines", *Crop Science* 31(3):656-660 (1991).
International Search Report mailed Aug. 20, 2008 in PCT/US2008/003973.
Lee et al., "Identification of quantitative trait loci for plant height, lodging, and maturity in a soybean population segregating for growth habit", *Theor Appl Genet* 92:516-523 (1996).
Mansur et al., "Determining the linkage of quantitative trait loci to RFLP markers using extreme phenotypes of recombinant inbreds of soybean (*Glycine max* L. Merr.)", *Theor Appl Genet* 86:914-918 (1993).
Rafalski, "Applicants of single nucleotide polymorphisms in crop genetics", *Current Opinion in Plant Biology* 5(2):94-100 (2002).
Song et al., "A selected set of trinucleotide simple sequence repeat markers for soybean cultivar identification", *Plant Varieties and Seeds* 12:207-220 (1999).
Yamanaka et al., "Quantitative Trait Locus Analysis of Flowering Time in Soybean Using a RFLP Linkage Map", *Breeding Science* 50:109-115 (2000).
Yoon et al., "BARCSoySNP23: a panel of 23 selected SNPs for soybean cultivar identification", *Theor Appl Genet* 114:885-899 (2007).
Zhang et al., "QTL mapping of ten agronomic traits on the soybean (*Glycine max* L. Merr.) genetic map and their association with EST markers", *Theor Appl Genet* 108:1131-1139 (2004).

(Continued)

*Primary Examiner* — David T Fox
(74) *Attorney, Agent, or Firm* — Arnold & Porter LLP; Lawrence Levin, Jr.; David Marsh

(57) ABSTRACT

The invention includes methods and compositions of genomic regions for screening and selecting plants and seeds from the genus *Glycine* associated with soybean plant maturity and growth habit. The invention also includes methods and compositions for screening plants and seeds from the genus *Glycine* with markers associated with genomic regions that are related to the plant maturity and plant growth habit of *Glycine* plants.

33 Claims, 3 Drawing Sheets

(56) References Cited

OTHER PUBLICATIONS

Barwale et al., "Plant regeneration from callus cultures of several soybean genotypes via embryogenesis and organogenesis," *Planta*, 167:473-481 (1986).
Cheng et al., "Plant regeneration from soybean cotyledonary node segments in culture," *Plant Science Letters*, 19:91-99 (1980).
Clemente et al., "Progeny Analysis of Glyphosate Selected Transgenic Soybeans Derived from *Agrobacterium*-Mediated Transformation," *Crop Science*, 40:797-803 (2000).
Cregan et al., "An Integrated Genetic Linkage Map of the Soybean Genome," *Crop Science*, 39:1464-1490 (1999).
Garner et al., "Effect of the Relative Length of Day and Night and Other Factors of the Environment on Growth and Reproduction in Plants," *J. Agric. Res.* 18(2), 553-606 (1920).
Kameya et al., "Plant Regeneration from Hypocotyl Sections of *Glycine* Species," *Plant Science Letters*, 21:289-294 (1981).
Kanehisa, "Use of statistical criteria for screening potential homologies in nucleic acid sequences," *Nucleic Acids Research*, 12(1):203-213 (1984).
Kartha et al., "Plant regeneration from meristems of grain legumes: soybean, cowpea, peanut, chickpea, and bean," *Canadian Journal of Botany*, 59:1671-1679 (1981).
Mansur et al., "Genetic Mapping of Agronomic Traits Using Recombinant Inbred Lines of Soybean," *Crop Science*, 36:1327-1336 (1996).
Mullis et al., "Specific Enzymatic Amplification of DNA In Vitro: The Polymerase Chain Reaction," *Cold Spring Harbor Symposium on Quantitative Biology*, 51:263-273 (1986).
Piper el al., "Temperature and Cultivar Effects on Soybean Seed Oil and Protein Concentrations," *JAOCS*, 76(10):1233-1241 (1999).
Prober et al., "A System for Rapid DNA Sequencing with Fluorescent Chain-Terminating Dideoxynucleotides," *Science*, 238:336-341 (1987).
Ranch et al., "Plant Regeneration from Embryo-Derived Tissue Cultures of Soybeans," *In Vitro Cellular & Developmental Biology*, 21(11):653-658 (1985).
Saka et al., "Stimulation of Multiple Shoot Formation on Soybean Stem Nodes in Culture," *Plant Science Letters*, 19:193-201 (1980).
Shoemaker et al., "Molecular Genetic Mapping of Soybean: Map Utilization," *Crop Science*, 32:1091-1098 (1992).
Shoemaker et al., "Integration of the Soybean Molecular and Classical Genetic Linkage Groups," *Crop Science*, 35:436-446 (1995).
Shoemaker et al., "Genome Duplication in Soybean (*Glycine* subgenus *soja*)," *Genetics*, 144:329-338 (1996).
Specht et al., "Soybean Response to Water: A QTL Analysis of Drought Tolerance," *Crop Science*, 41:493-509 (2001).
Tingey et al., "An RFLP Map of the Soybean Genome," *J. Cell Biochem. Suppl.*, 14E:291 (1990).
Wetmur et al., "Kinetics of Renaturation of DNA," *J. Mol. Biol.*, 31:349-370 (1968).
Wright et al., "Plant regeneration by organogenesis in *Glycine max*," *Plant Cell Reports*, 5:150-154 (1986).
Yaklich et al., "Analysis of Seed Protein and Oil from Soybean Northern and Southern Region Uniform Tests," *Crop Science*, 42:1504-1515 (2002).
Bernard, "Two Major Genes for Time of Flowering and Maturity in Soybeans", *Crop Science*, 11:242-244 (1971).
Buzzell, "Inheritance of a Soybean Flowering Response to Fluorescent-Daylength Conditions", *Can J. Genet Cytol*, 13:703-707 (1971).
Cober et al., "Genetic Control of Photoperiod Response in Early-Maturing, Near-Isogenic Soybean Lines", *Crop Science*, 36:601-605 (1996).
Cober et al., "A New Soybean Maturity and Photoperiod-Sensitivity Locus Linked to $E1$ and $T$", *Crop Science*, 41:698-701 (2001).
Curtis et al., "Agronomic and Phenological Differences of Soybean Isolines Differing in Maturity and Growth Habit", *Crop Science*, 40:1624-1629 (2000).
Lee et al., "Molecular Markers Associated with Soybean Plant Height, Lodging, and Maturity Across Locations", *Crop Science*, 36:728-735 (1996).
McBlain et al., "A Procedure to Identify Genes Affecting Maturity Using Soybean Isoline Testers", *Crop Science* 27:1127-1132 (1987).
Messina et al., "A Gene-Based Model to Stimulate Soybean Development and Yield Responses to Environment", *Crop Science*, 46:456-466 (2006).
Molnar et al., "Simple sequence repeat (SSR) markers linked to $E1$, $E3$, $E4$, and $E7$ maturity genes in soybean", *Genome*, 46:1024-1036 (2003).
Nissly et al., "Variation in Photoperiod Sensitivity for Time of Flowering and Maturity Among Soybean Strains of Maturity Group III", *Crop Science*, 21:833-836 (1981).
Tasma et al., "Mapping genetic loci for flowering time, maturity, and photoperiod insensitivity in soybean", *Molecular Breeding*, 8:25-35 (2001).
Tasma et al., "Mapping Flowering Time Gene Homologs in Soybean and Their Association with Maturity ($E$) Loci", *Crop Science*, 43:319-328 (2003).

\* cited by examiner

UTILITY OF SNP MARKERS ASSOCIATED WITH MAJOR SOYBEAN PLANT MATURITY AND GROWTH HABIT GENOMIC REGIONS

CROSS-REFERENCE TO RELATED APPLICATIONS

This application claims the benefit under 35 U.S.C. §119 (e) of U.S. Provisional Application Nos. 60/920,531, filed Mar. 28, 2007, and 61/001,049, filed Oct. 31, 2007. The entirety of each of these applications is hereby incorporated by reference.

INCORPORATION OF THE SEQUENCE LISTING

Two copies of the Sequence Listing and a computer readable form of the sequence listing on CD-ROM, each containing the file named "SequenceListing.txt", which is 140,000 bytes in size (measured in MS-Windows) are filed herewith and herein incorporated by reference. A paper copy of the Sequence Listing and a computer readable form of the sequence listing on diskette, containing the file named "pa_seq_54590.txt" which is 143,360 bytes in size (measured in MS-Windows) and which was recorded on Mar. 14, 2007 and filed in U.S. Application No. 60/920,531 are herein incorporated by reference. The file named "SequenceListing-revised.txt," which is 143,064 bytes in size (measured in Windows XP) and which was created on Nov. 24, 2010 is herein expressly incorporated by reference.

FIELD OF THE INVENTION

The invention includes methods and compositions of genomic regions for screening and selecting plants and seeds from the genus *Glycine* associated with soybean plant maturity and growth habit. The invention also includes methods and compositions for screening plants and seeds from the genus *Glycine* with markers associated with genomic regions that are related to the plant maturity and plant growth habit of *Glycine* plants.

BACKGROUND OF THE INVENTION

The soybean, *Glycine max* (L.) Merril, is a major economic crop worldwide and is a primary source of vegetable oil and protein (Sinclair and Backman, *Compendium of Soybean Diseases*, 3rd Ed. APS Press, St. Paul, Minn., p. 106. (1989)). The growing demand for low cholesterol and high fiber diets has also increased importance of soybean as a health food.

Soybean varieties grown in the United States have a narrow genetic base. Six introductions, 'Mandarin,' 'Manchu,' 'Mandarin' (Ottawa), "Richland," 'AK' (Harrow), and 'Mukden,' contributed nearly 70% of the germplasm represented in 136 cultivar releases. The genetic base of cultivated soybean could be widened through the use of exotic species. In addition, exotic species may possess such key traits as disease and stress resistance. At present, the traits of many exotic species are inaccessible in part due to limitations with crossing soybean plants from extremely different maturity groups. Most soybean variety development crosses are made between parents within 10 maturity days of each other. If the parents differ greatly in maturity, the progeny plants segregate widely for maturity. In order for breeders to obtain and select for soybean plants of the desired maturity group, they must produce and maintain a large number of progeny plants, the practice of which is cost prohibitive.

Plant maturity and yield are closely associated in soybean. An increase of one day in maturity may be equivalent to a ~0.7 bu/A increase in yield. Conversely, a decrease in maturity is often penalized with a ~0.7 bu/A decrease in yield. The correlation of plant maturity and yield confounds the evaluation of potential quantitative trail loci (QTLs) and candidate genes associated with yield. The ability to genetically fix maturity within a soybean plant would be helpful and assist in elucidating traits associated with yield.

Soybean plants are short day plants, therefore flowering is initiated by short days due to a decrease in photoperiod (Garner & Allard, *J. Agric. Res.* 18, 553-606 (1920)). Consequently, photoperiod (day length) and temperature response of the soybean plant determine areas of plant adaptation. Due to photoperiod sensitivity, soybean genotypes are often grown in narrow zones of latitude to optimize yield. Northern soybean varieties, in contrast to Southern varieties, initiate flowering with longer days. Northern varieties planted south of their adaptation zone exhibit accelerated flowering, limited plant growth and reduced yield. Southern soybean varieties planted north of their adaptation zone will have delayed flowering with a potential for frost damage that may reduce yield.

Soybean plant varieties are classified based on bands of adaptation that are determined by latitude and day length. In North America, soybeans are categorized into 13 maturity groups with the designations ranging from maturity groups 000, 00, 0, and I through X. The earliest maturity group 000 soybeans are adapted to the north (45° latitude), while the latest maturity group X soybeans are adapted to regions near the equator. Soybean plants in maturity groups 000 to IV have indeterminate plant structure, while soybean plants in maturity groups V through X have determinate plant structure. Determinate varieties cease vegetative growth after the main stem terminates in a cluster of mature pods. Indeterminate varieties develop leaves and flowers simultaneously throughout a portion of their reproductive period, with one to three pods at the terminal apex. Early maturity varieties (000 to III) are adapted to northern latitudes with the maturity designation increasing in southern latitudes. The maturity group is determined by the maturity date. Plants are considered mature when 95% of the pods have reached their mature color. The maturity date is typically described as a measurement of days after August $31^{st}$ in the northern hemisphere.

There is a need in the art of plant breeding to identify genomic regions associated with the maturity group of a soybean plant. At present, soybean breeders are limited to crossing plants within similar maturity groups. In addition, a number of traits, like oil levels, are influenced by latitude and maturity growing region. Therefore, there is a need for a rapid, cost-efficient method to pre-select for maturity group of soybean plants. The present invention includes a method for screening and selecting a soybean plant for a preferred plant maturity using single nucleotide polymorphism (SNP) technology.

SUMMARY OF THE INVENTION

Figure 1:
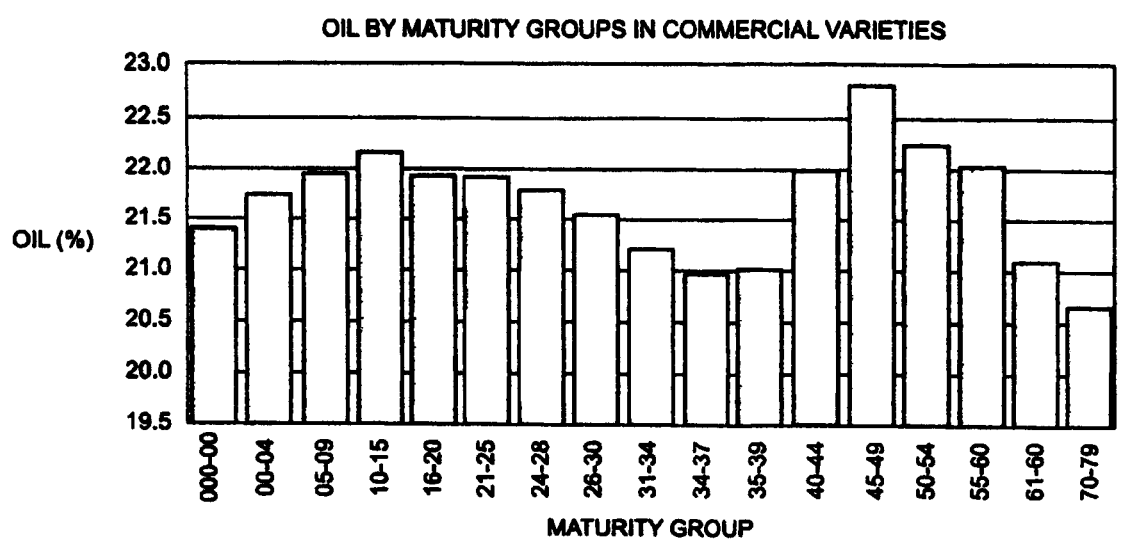
FIG. 1: Influence of maturity group on percent oil in commercial soybeans.

The present invention includes a method of establishing where a soybean plant or soybean seed should be grown by determining the allelic combination of a soybean plant or soybean seed by obtaining DNA from a soybean plant or soybean seed; determining if alleles at a locus within maturity genomic region 1 are homozygous or heterozygous; determining if alleles at a locus within maturity genomic region 2 are homozygous or heterozygous; determining if alleles at a locus within maturity genomic region 3 are homozygous or heterozygous; determining the allelic combination of the alleles within maturity genomic regions 1, 2, and 3; and assigning a maturity group value to the soybean plant or soybean seed.

In another aspect, the present invention includes a method of establishing where a soybean plant or soybean seed should be grown by determining the allelic combination of a soybean plant or soybean seed by obtaining DNA from a soybean plant or soybean seed; determining if alleles at a locus within maturity genomic region 1 are homozygous or heterozygous; determining if alleles at a locus within maturity genomic region 2 are homozygous or heterozygous; determining if alleles at a locus within maturity genomic region 3 are homozygous or heterozygous; determining if alleles at a locus within maturity genomic region 2 are homozygous or heterozygous; determining the allelic combination of the alleles within maturity genomic regions 1, 2, 3 and 4; and assigning a maturity group value to the soybean plant or soybean seed.

The present invention also includes a method of providing information about the maturity of a soybean plant or soybean seed by obtaining DNA from the soybean seed or soybean plant and determining the allelic profile at a locus of genomic region 4.

The present invention also includes a method of establishing where a soybean plant or soybean seed should be grown by determining the allelic combination of a soybean plant or soybean seed by obtaining DNA from a soybean plant or soybean seed; determining if an allele within maturity genomic region 1 is homozygous or heterozygous; determining if an allele within maturity genomic region 2 is homozygous or heterozygous; determining if an allele within maturity genomic region 3 is homozygous or heterozygous; and determining the allelic combination of the alleles within maturity genomic regions 1, 2, and 3.

An aspect of the present invention includes a method of establishing where a soybean plant or soybean seed should be grown by determining the allelic combination of a soybean plant by obtaining DNA from a soybean plant or soybean seed; determining if an allele within maturity genomic region 1 is homozygous or heterozygous; determining if an allele within maturity genomic region 2 is homozygous or heterozygous; determining the allelic combination of the alleles within maturity genomic regions 1 and 2; and assigning a maturity growth value to the soybean plant or soybean seed.

In an aspect of the present invention, a method of soybean plant breeding includes crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group.

An aspect of the present invention includes a method of selecting a soybean plant for germplasm improvement by determining a maturity group by crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group; and incorporating the selected soybean plant into a use selected from any of using the soybean plant for breeding, advancement of the soybean plant through self-fertilization, trait integration, use of soybean plant or parts thereof for transformation, and use of soybean plants or parts thereof for mutagenesis.

Another aspect of the present invention includes a method of co-selecting a soybean plant for expression of a non-maturity phenotypic trait and a maturity trait by crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group; and determining the desired geography for the progeny soybean plant growth, and a method for determining the non-maturity phenotype.

In one aspect the present invention includes a method of soybean plant breeding by assaying a soybean plant for the presence of a marker sequences selected from the group consisting of SEQ ID NO: 143 through SEQ ID NO: 213; and associating the soybean plant with a maturity group.

In another aspect the present invention includes a method of soybean plant breeding comprising crossing a parent soybean plant having a desired trait with a second parent soybean plant, wherein the parent soybean plants differ in soybean plant maturity by over 5 days, over 10 days, 10 days-20 days, or 10 days-30 days, by crossing a parent soybean plant comprising a desired trait with a second parent soybean plant; obtaining progeny soybean seed from the cross; screening a progeny soybean seed for the trait; screening a progeny soybean seed for a desired maturity group using a marker selected from the group consisting of SEQ ID NO: 143 through SEQ ID NO: 213 to determine the desired geographical growing region; and selecting a progeny soybean seed containing the desired trait and desired soybean plant maturity.

An aspect of the present invention includes a method of soybean plant breeding by crossing at least two different parent soybean plants, wherein the parent soybean plants differ in soybean plant maturity by over 5 days, over 10 days, 10 days-20 days, or 10 days-30 days; obtaining a progeny soybean seed from the cross; genotyping a progeny soybean seed of the cross with a genetic marker; and selecting a soybean seed possessing a genotype for preferred maturity.

Another aspect of the present invention includes a method of screening soybean seeds based on soybean plant maturity group by obtaining DNA from a soybean seed; determining if an allele within maturity genomic region 1 is homozygous or heterozygous; determining if an allele within maturity genomic region 2 is homozygous or heterozygous; determining if an allele within maturity genomic region 3 is homozygous or heterozygous; and assigning a maturity growth value to the soybean seed.

One aspect of the present invention includes a method to select a soybean seed based on indeterminate or determinate growth habit comprising determining if maturity genomic region 3 is homozygous or heterozygous.

Another aspect of the present invention includes a method of distributing a soybean plant based on maturity group by obtaining DNA from a soybean plant; determining if an allele within maturity genomic region 1 is homozygous or heterozygous; determining if an allele within maturity genomic region 2 is homozygous or heterozygous; determining if an allele within maturity genomic region 3 is homozygous or heterozygous; and assigning a maturity growth value to the soybean plant; and shipping the soybean plant to a preferred geographic region.

Another aspect of the present invention includes a method to isolate indeterminate-early maturity soybean seeds by obtaining DNA from the soybean seed using a non-destructive method; determining if an allele within maturity genomic region 1 is homozygous or heterozygous; and determining if an allele within maturity genomic region 2 is homozygous or heterozygous.

An aspect of the present invention includes a method of determining if a soybean seed will grow into a soybean plant having a maturity group of III-VI by determining a homozygous or heterozygous marker within the soybean seed using a marker with the nucleic acid sequence of SEQ ID NO: 151.

Another aspect of the present invention includes a method of determining if a soybean seed will grow into a soybean plant having a maturity group between 0.0-III.0 comprising determining if an 11-basepair insertion within the nucleic acid sequence of SEQ ID NO: 149 exists in the soybean seed.

An aspect of the present invention includes a method to determine if a soybean plant has a maturity group of 0.0-III.9 by determining if an allele within maturity genomic region 1 is homozygous or heterozygous; determining if an allele within maturity genomic region 2 is homozygous or heterozygous; and assigning a maturity group value for the soybean plant between 0.0-III.9.

One aspect of the present invention is a method of introgressing an allele into a soybean plant by crossing at least two different parent soybean plants; obtaining a progeny soybean plant from the cross; screening the progeny soybean plant of the cross for the allele; obtaining DNA from a soybean seed of the progeny soybean plant using a non-destructive method; and selecting a soybean seed, wherein the soybean seed comprises the allele and a nucleic acid sequence selected from the group consisting of SEQ ID NOs: 143-213.

Another aspect of the present invention includes a method of introducing a desired trait into a soybean plant by crossing at least two different parent soybean plants, wherein at least one parent soybean plant has a desired trait; obtaining a progeny soybean seed from the cross; obtaining DNA from a soybean seed of the progeny soybean plant using a non-destructive method; assaying the progeny soybean seed of the cross for evidence of the desired trait; and selecting the soybean seed with the desired trait and a desired maturity group. In a preferred aspect, the desired trait is transgenic.

A further aspect of the present invention includes a method of introgressing an allele into a soybean plant by crossing at least two different parent soybean plants; obtaining a progeny soybean plant from the cross; obtaining DNA from a soybean seed of the progeny soybean plant using a non-destructive method; and selecting a soybean seed with the allele and a nucleic acid sequence selected from the group consisting of SEQ ID NOs: 143-174.

A method of soybean plant breeding by crossing at least two different parent soybean plants, wherein the parent soybean plants differ in soybean plant maturity by over 10 days; obtaining progeny soybean seed from the cross; genotyping the progeny soybean seed of the cross with a genetic marker selected from the group consisting of SEQ ID NOs: 143-213; and selecting a soybean seed with a desired maturity group.

An aspect of the present invention includes a method of detecting maturity genomic region 4 by detecting an allele using a marker selected from any of SEQ ID NO: 175-180. Another aspect of the present invention includes a method of detecting maturity genomic region 5 by detecting an allele using a marker selected from any of SEQ ID NO: 181-189. Another aspect of the present invention includes a method of detecting maturity genomic region 6 by detecting an allele using a marker selected from any of SEQ ID NO: 190-196. Another aspect of the present invention includes a method of detecting maturity genomic region 7 by detecting an allele using a marker selected from any of SEQ ID NO: 197-203. Another aspect of the present invention includes a method of detecting maturity genomic region 8 by detecting an allele using a marker selected from any of SEQ ID NO: 204-213.

A further aspect of the present invention includes a soybean plant comprising within its genome an introgressed haplotype associated with maturity, wherein the introgression is facilitated by at least one of the markers from SEQ ID NO: 143-213.

BRIEF DESCRIPTION OF NUCLEIC ACID SEQUENCES

SEQ ID NO: 1 is a forward PCR primer for the amplification of SEQ ID NO: 143.
SEQ ID NO: 2 is a reverse PCR primer for the amplification of SEQ ID NO: 143.
SEQ ID NO: 3 is a forward PCR primer for the amplification of SEQ ID NO: 144.
SEQ ID NO: 4 is a reverse PCR primer for the amplification of SEQ ID NO: 144.
SEQ ID NO: 5 is a forward PCR primer for the amplification of SEQ ID NO: 145.
SEQ ID NO: 6 is a reverse PCR primer for the amplification of SEQ ID NO: 145.
SEQ ID NO: 7 is a forward PCR primer for the amplification of SEQ ID NO: 146.
SEQ ID NO: 8 is a reverse PCR primer for the amplification of SEQ ID NO: 146.
SEQ ID NO: 9 is a forward PCR primer for the amplification of SEQ ID NO: 147.
SEQ ID NO: 10 is a reverse PCR primer for the amplification of SEQ ID NO: 147.
SEQ ID NO: 11 is a forward PCR primer for the amplification of SEQ ID NO: 148.
SEQ ID NO: 12 is a reverse PCR primer for the amplification of SEQ ID NO: 148.
SEQ ID NO: 13 is a forward PCR primer for the amplification of SEQ ID NO: 149.
SEQ ID NO: 14 is a reverse PCR primer for the amplification of SEQ ID NO: 149.
SEQ ID NO: 15 is a forward PCR primer for the amplification of SEQ ID NO: 150.
SEQ ID NO: 16 is a reverse PCR primer for the amplification of SEQ ID NO: 150.
SEQ ID NO: 17 is a forward PCR primer for the amplification of SEQ ID NO: 151.
SEQ ID NO: 18 is a reverse PCR primer for the amplification of SEQ ID NO: 151.
SEQ ID NO: 19 is a forward PCR primer for the amplification of SEQ ID NO: 152.
SEQ ID NO: 20 is a reverse PCR primer for the amplification of SEQ ID NO: 152.
SEQ ID NO: 21 is a forward PCR primer for the amplification of SEQ ID NO: 153.
SEQ ID NO: 22 is a reverse PCR primer for the amplification of SEQ ID NO: 153.
SEQ ID NO: 23 is a forward PCR primer for the amplification of SEQ ID NO: 154.
SEQ ID NO: 24 is a reverse PCR primer for the amplification of SEQ ID NO: 154.

SEQ ID NO: 25 is a forward PCR primer for the amplification of SEQ ID NO: 155.
SEQ ID NO: 26 is a reverse PCR primer for the amplification of SEQ ID NO: 155.
SEQ ID NO: 27 is a forward PCR primer for the amplification of SEQ ID NO: 156.
SEQ ID NO: 28 is a reverse PCR primer for the amplification of SEQ ID NO: 156.
SEQ ID NO: 29 is a forward PCR primer for the amplification of SEQ ID NO: 157.
SEQ ID NO: 30 is a reverse PCR primer for the amplification of SEQ ID NO: 157.
SEQ ID NO: 31 is a forward PCR primer for the amplification of SEQ ID NO: 158.
SEQ ID NO: 32 is a reverse PCR primer for the amplification of SEQ ID NO: 158.
SEQ ID NO: 33 is a forward PCR primer for the amplification of SEQ ID NO: 159.
SEQ ID NO: 34 is a reverse PCR primer for the amplification of SEQ ID NO: 159.
SEQ ID NO: 35 is a forward PCR primer for the amplification of SEQ ID NO: 160.
SEQ ID NO: 36 is a reverse PCR primer for the amplification of SEQ ID NO: 160.
SEQ ID NO: 37 is a forward PCR primer for the amplification of SEQ ID NO: 161.
SEQ ID NO: 38 is a reverse PCR primer for the amplification of SEQ ID NO: 161.
SEQ ID NO: 39 is a forward PCR primer for the amplification of SEQ ID NO: 162.
SEQ ID NO: 40 is a reverse PCR primer for the amplification of SEQ ID NO: 162.
SEQ ID NO: 41 is a forward PCR primer for the amplification of SEQ ID NO: 163.
SEQ ID NO: 42 is a reverse PCR primer for the amplification of SEQ ID NO: 163.
SEQ ID NO: 43 is a forward PCR primer for the amplification of SEQ ID NO: 164.
SEQ ID NO: 44 is a reverse PCR primer for the amplification of SEQ ID NO: 164.
SEQ ID NO: 45 is a forward PCR primer for the amplification of SEQ ID NO: 165.
SEQ ID NO: 46 is a reverse PCR primer for the amplification of SEQ ID NO: 165.
SEQ ID NO: 47 is a forward PCR primer for the amplification of SEQ ID NO: 166.
SEQ ID NO: 48 is a reverse PCR primer for the amplification of SEQ ID NO: 166.
SEQ ID NO: 49 is a forward PCR primer for the amplification of SEQ ID NO: 167.
SEQ ID NO: 50 is a reverse PCR primer for the amplification of SEQ ID NO: 167.
SEQ ID NO: 51 is a forward PCR primer for the amplification of SEQ ID NO: 168.
SEQ ID NO: 52 is a reverse PCR primer for the amplification of SEQ ID NO: 168.
SEQ ID NO: 53 is a forward PCR primer for the amplification of SEQ ID NO: 169.
SEQ ID NO: 54 is a reverse PCR primer for the amplification of SEQ ID NO: 169.
SEQ ID NO: 55 is a forward PCR primer for the amplification of SEQ ID NO: 170.
SEQ ID NO: 56 is a reverse PCR primer for the amplification of SEQ ID NO: 170.
SEQ ID NO: 57 is a forward PCR primer for the amplification of SEQ ID NO: 171.
SEQ ID NO: 58 is a reverse PCR primer for the amplification of SEQ ID NO: 171.
SEQ ID NO: 59 is a forward PCR primer for the amplification of SEQ ID NO: 172.
SEQ ID NO: 60 is a reverse PCR primer for the amplification of SEQ ID NO: 172.
SEQ ID NO: 61 is a forward PCR primer for the amplification of SEQ ID NO: 173.
SEQ ID NO: 62 is a reverse PCR primer for the amplification of SEQ ID NO: 173.
SEQ ID NO: 63 is a forward PCR primer for the amplification of SEQ ID NO: 174.
SEQ ID NO: 64 is a reverse PCR primer for the amplification of SEQ ID NO: 174.
SEQ ID NO: 65 is a forward PCR primer for the amplification of SEQ ID NO: 175.
SEQ ID NO: 66 is a reverse PCR primer for the amplification of SEQ ID NO: 175.
SEQ ID NO: 67 is a forward PCR primer for the amplification of SEQ ID NO: 176.
SEQ ID NO: 68 is a reverse PCR primer for the amplification of SEQ ID NO: 176.
SEQ ID NO: 69 is a forward PCR primer for the amplification of SEQ ID NO: 177.
SEQ ID NO: 70 is a reverse PCR primer for the amplification of SEQ ID NO: 177.
SEQ ID NO: 71 is a forward PCR primer for the amplification of SEQ ID NO: 178.
SEQ ID NO: 72 is a reverse PCR primer for the amplification of SEQ ID NO: 178.
SEQ ID NO: 73 is a forward PCR primer for the amplification of SEQ ID NO: 179.
SEQ ID NO: 74 is a reverse PCR primer for the amplification of SEQ ID NO: 179.
SEQ ID NO: 75 is a forward PCR primer for the amplification of SEQ ID NO: 180.
SEQ ID NO: 76 is a reverse PCR primer for the amplification of SEQ ID NO: 180.
SEQ ID NO: 77 is a forward PCR primer for the amplification of SEQ ID NO: 181.
SEQ ID NO: 78 is a reverse PCR primer for the amplification of SEQ ID NO: 181.
SEQ ID NO: 79 is a forward PCR primer for the amplification of SEQ ID NO: 182.
SEQ ID NO: 80 is a reverse PCR primer for the amplification of SEQ ID NO: 182.
SEQ ID NO: 81 is a forward PCR primer for the amplification of SEQ ID NO: 183.
SEQ ID NO: 82 is a reverse PCR primer for the amplification of SEQ ID NO: 183.
SEQ ID NO: 83 is a forward PCR primer for the amplification of SEQ ID NO: 184.
SEQ ID NO: 84 is a reverse PCR primer for the amplification of SEQ ID NO: 184.
SEQ ID NO: 85 is a forward PCR primer for the amplification of SEQ ID NO: 185.
SEQ ID NO: 86 is a reverse PCR primer for the amplification of SEQ ID NO: 185.
SEQ ID NO: 87 is a forward PCR primer for the amplification of SEQ ID NO: 186.
SEQ ID NO: 88 is a reverse PCR primer for the amplification of SEQ ID NO: 186.
SEQ ID NO: 89 is a forward PCR primer for the amplification of SEQ ID NO: 187.
SEQ ID NO: 90 is a reverse PCR primer for the amplification of SEQ ID NO: 187.

SEQ ID NO: 91 is a forward PCR primer for the amplification of SEQ ID NO: 188.
SEQ ID NO: 92 is a reverse PCR primer for the amplification of SEQ ID NO: 188.
SEQ ID NO: 93 is a forward PCR primer for the amplification of SEQ ID NO: 189.
SEQ ID NO: 94 is a reverse PCR primer for the amplification of SEQ ID NO: 189.
SEQ ID NO: 95 is a forward PCR primer for the amplification of SEQ ID NO: 190.
SEQ ID NO: 96 is a reverse PCR primer for the amplification of SEQ ID NO: 190.
SEQ ID NO: 97 is a forward PCR primer for the amplification of SEQ ID NO: 191.
SEQ ID NO: 98 is a reverse PCR primer for the amplification of SEQ ID NO: 191.
SEQ ID NO: 99 is a forward PCR primer for the amplification of SEQ ID NO: 192.
SEQ ID NO: 100 is a reverse PCR primer for the amplification of SEQ ID NO: 192.
SEQ ID NO: 101 is a forward PCR primer for the amplification of SEQ ID NO: 193.
SEQ ID NO: 102 is a reverse PCR primer for the amplification of SEQ ID NO: 193.
SEQ ID NO: 103 is a forward PCR primer for the amplification of SEQ ID NO: 194.
SEQ ID NO: 104 is a reverse PCR primer for the amplification of SEQ ID NO: 194.
SEQ ID NO: 105 is a forward PCR primer for the amplification of SEQ ID NO: 195.
SEQ ID NO: 106 is a reverse PCR primer for the amplification of SEQ ID NO: 195.
SEQ ID NO: 107 is a forward PCR primer for the amplification of SEQ ID NO: 196.
SEQ ID NO: 108 is a reverse PCR primer for the amplification of SEQ ID NO: 196.
SEQ ID NO: 109 is a forward PCR primer for the amplification of SEQ ID NO: 197.
SEQ ID NO: 110 is a reverse PCR primer for the amplification of SEQ ID NO: 197.
SEQ ID NO: 111 is a forward PCR primer for the amplification of SEQ ID NO: 198.
SEQ ID NO: 112 is a reverse PCR primer for the amplification of SEQ ID NO: 198.
SEQ ID NO: 113 is a forward PCR primer for the amplification of SEQ ID NO: 199.
SEQ ID NO: 114 is a reverse PCR primer for the amplification of SEQ ID NO: 199.
SEQ ID NO: 115 is a forward PCR primer for the amplification of SEQ ID NO: 200.
SEQ ID NO: 116 is a reverse PCR primer for the amplification of SEQ ID NO: 200.
SEQ ID NO: 117 is a forward PCR primer for the amplification of SEQ ID NO: 201.
SEQ ID NO: 118 is a reverse PCR primer for the amplification of SEQ ID NO: 201.
SEQ ID NO: 119 is a forward PCR primer for the amplification of SEQ ID NO: 202.
SEQ ID NO: 120 is a reverse PCR primer for the amplification of SEQ ID NO: 202.
SEQ ID NO: 121 is a forward PCR primer for the amplification of SEQ ID NO: 203.
SEQ ID NO: 122 is a reverse PCR primer for the amplification of SEQ ID NO: 203.
SEQ ID NO: 123 is a forward PCR primer for the amplification of SEQ ID NO: 204.
SEQ ID NO: 124 is a reverse PCR primer for the amplification of SEQ ID NO: 204.
SEQ ID NO: 125 is a forward PCR primer for the amplification of SEQ ID NO: 205.
SEQ ID NO: 126 is a reverse PCR primer for the amplification of SEQ ID NO: 205.
SEQ ID NO: 127 is a forward PCR primer for the amplification of SEQ ID NO: 206.
SEQ ID NO: 128 is a reverse PCR primer for the amplification of SEQ ID NO: 206.
SEQ ID NO: 129 is a forward PCR primer for the amplification of SEQ ID NO: 207.
SEQ ID NO: 130 is a reverse PCR primer for the amplification of SEQ ID NO: 207.
SEQ ID NO: 131 is a forward PCR primer for the amplification of SEQ ID NO: 208.
SEQ ID NO: 132 is a reverse PCR primer for the amplification of SEQ ID NO: 208.
SEQ ID NO: 133 is a forward PCR primer for the amplification of SEQ ID NO: 209.
SEQ ID NO: 134 is a reverse PCR primer for the amplification of SEQ ID NO: 209.
SEQ ID NO: 135 is a forward PCR primer for the amplification of SEQ ID NO: 210.
SEQ ID NO: 136 is a reverse PCR primer for the amplification of SEQ ID NO: 210.
SEQ ID NO: 137 is a forward PCR primer for the amplification of SEQ ID NO: 211.
SEQ ID NO: 138 is a reverse PCR primer for the amplification of SEQ ID NO: 211.
SEQ ID NO: 139 is a forward PCR primer for the amplification of SEQ ID NO: 212.
SEQ ID NO: 140 is a reverse PCR primer for the amplification of SEQ ID NO: 212.
SEQ ID NO: 141 is a forward PCR primer for the amplification of SEQ ID NO: 213.
SEQ ID NO: 142 is a reverse PCR primer for the amplification of SEQ ID NO: 213.
SEQ ID NO: 143 is a genomic sequence derived from *Glycine max* corresponding to maturity locus 1.
SEQ ID NO: 144 is a genomic sequence derived from *Glycine max* corresponding to maturity locus 1.
SEQ ID NO: 145 is a genomic sequence derived from *Glycine max* corresponding to maturity locus 1.
SEQ ID NO: 146 is a genomic sequence derived from *Glycine max* corresponding to maturity locus 1.
SEQ ID NO: 147 is a genomic sequence derived from *Glycine max* corresponding to maturity locus 1.
SEQ ID NO: 148 is a genomic sequence derived from *Glycine max* corresponding to maturity locus 1.
SEQ ID NO: 149 is a genomic sequence derived from *Glycine max* corresponding to maturity locus 1.
SEQ ID NO: 150 is a genomic sequence derived from *Glycine max* corresponding to maturity locus 1.
SEQ ID NO: 151 is a genomic sequence derived from *Glycine max* corresponding to maturity locus 1.
SEQ ID NO: 152 is a genomic sequence derived from *Glycine max* corresponding to maturity locus 1.
SEQ ID NO: 153 is a genomic sequence derived from *Glycine max* corresponding to maturity locus 1.
SEQ ID NO: 154 is a genomic sequence derived from *Glycine max* corresponding to maturity locus 1.
SEQ ID NO: 155 is a genomic sequence derived from *Glycine max* corresponding to maturity locus 1.
SEQ ID NO: 156 is a genomic sequence derived from *Glycine max* corresponding to maturity locus 2.

SEQ ID NO: 157 is a genomic sequence derived from *Glycine max* corresponding to maturity locus 2.
SEQ ID NO: 158 is a genomic sequence derived from *Glycine max* corresponding to maturity locus 2.
SEQ ID NO: 159 is a genomic sequence derived from *Glycine max* corresponding to maturity locus 2.
SEQ ID NO: 160 is a genomic sequence derived from *Glycine max* corresponding to maturity locus 2.
SEQ ID NO: 161 is a genomic sequence derived from *Glycine max* corresponding to maturity locus 2.
SEQ ID NO: 162 is a genomic sequence derived from *Glycine max* corresponding to maturity locus 3.
SEQ ID NO: 163 is a genomic sequence derived from *Glycine max* corresponding to maturity locus 3.
SEQ ID NO: 164 is a genomic sequence derived from *Glycine max* corresponding to maturity locus 3.
SEQ ID NO: 16.5 is a genomic sequence derived from *Glycine max* corresponding to maturity locus 3.
SEQ ID NO: 166 is a genomic sequence derived from *Glycine max* corresponding to maturity locus 3.
SEQ ID NO: 167 is a genomic sequence derived from *Glycine max* corresponding to maturity locus 3.
SEQ ID NO: 168 is a genomic sequence derived from *Glycine max* corresponding to maturity locus 3.
SEQ ID NO: 169 is a genomic sequence derived from *Glycine max* corresponding to maturity locus 3.
SEQ ID NO: 170 is a genomic sequence derived from *Glycine max* corresponding to maturity locus 3.
SEQ ID NO: 171 is a genomic sequence derived from *Glycine max* corresponding to maturity locus 3.
SEQ ID NO: 172 is a genomic sequence derived from *Glycine max* corresponding to maturity locus 3.
SEQ ID NO: 173 is a genomic sequence derived from *Glycine max* corresponding to maturity locus 3.
SEQ ID NO: 174 is a genomic sequence derived from *Glycine max* corresponding to maturity locus 3.
SEQ ID NO: 175 is a genomic sequence derived from *Glycine max* corresponding to maturity locus 4.
SEQ ID NO: 176 is a genomic sequence derived from *Glycine max* corresponding to maturity locus 4.
SEQ ID NO: 177 is a genomic sequence derived from *Glycine max* corresponding to maturity locus 4.
SEQ ID NO: 178 is a genomic sequence derived from *Glycine max* corresponding to maturity locus 4.
SEQ ID NO: 179 is a genomic sequence derived from *Glycine max* corresponding to maturity locus 4.
SEQ ID NO: 180 is a genomic sequence derived from *Glycine max* corresponding to maturity locus 4.
SEQ ID NO: 181 is a genomic sequence derived from *Glycine max* corresponding to maturity locus 5.
SEQ ID NO: 182 is a genomic sequence derived from *Glycine max* corresponding to maturity locus 5.
SEQ ID NO: 183 is a genomic sequence derived from *Glycine max* corresponding to maturity locus 5.
SEQ ID NO: 184 is a genomic sequence derived from *Glycine max* corresponding to maturity locus 5.
SEQ ID NO: 185 is a genomic sequence derived from *Glycine max* corresponding to maturity locus 5.
SEQ ID NO: 186 is a genomic sequence derived from *Glycine max* corresponding to maturity locus 5.
SEQ ID NO: 187 is a genomic sequence derived from *Glycine max* corresponding to maturity locus 5.
SEQ ID NO: 188 is a genomic sequence derived from *Glycine max* corresponding to maturity locus 5.
SEQ ID NO: 189 is a genomic sequence derived from *Glycine max* corresponding to maturity locus 5.
SEQ ID NO: 190 is a genomic sequence derived from *Glycine max* corresponding to maturity locus 6.
SEQ ID NO: 191 is a genomic sequence derived from *Glycine max* corresponding to maturity locus 6.
SEQ ID NO: 192 is a genomic sequence derived from *Glycine max* corresponding to maturity locus 6.
SEQ ID NO: 193 is a genomic sequence derived from *Glycine max* corresponding to maturity locus 6.
SEQ ID NO: 194 is a genomic sequence derived from *Glycine max* corresponding to maturity locus 6.
SEQ ID NO: 195 is a genomic sequence derived from *Glycine max* corresponding to maturity locus 6.
SEQ ID NO: 196 is a genomic sequence derived from *Glycine max* corresponding to maturity locus 6.
SEQ ID NO: 197 is a genomic sequence derived from *Glycine max* corresponding to maturity locus 7.
SEQ ID NO: 198 is a genomic sequence derived from *Glycine max* corresponding to maturity locus 7.
SEQ ID NO: 199 is a genomic sequence derived from *Glycine max* corresponding to maturity locus 7.
SEQ ID NO: 200 is a genomic sequence derived from *Glycine max* corresponding to maturity locus 7.
SEQ ID NO: 201 is a genomic sequence derived from *Glycine max* corresponding to maturity locus 7.
SEQ ID NO: 202 is a genomic sequence derived from *Glycine max* corresponding to maturity locus 7.
SEQ ID NO: 203 is a genomic sequence derived from *Glycine max* corresponding to maturity locus 7.
SEQ ID NO: 204 is a genomic sequence derived from *Glycine max* corresponding to maturity locus 8.
SEQ ID NO: 205 is a genomic sequence derived from *Glycine max* corresponding to maturity locus 8.
SEQ ID NO: 206 is a genomic sequence derived from *Glycine max* corresponding to maturity locus 8.
SEQ ID NO: 207 is a genomic sequence derived from *Glycine max* corresponding to maturity locus 8.
SEQ ID NO: 208 is a genomic sequence derived from *Glycine max* corresponding to maturity locus 8.
SEQ ID NO: 209 is a genomic sequence derived from *Glycine max* corresponding to maturity locus 8.
SEQ ID NO: 210 is a genomic sequence derived from *Glycine max* corresponding to maturity locus 8.
SEQ ID NO: 211 is a genomic sequence derived from *Glycine max* corresponding to maturity locus 8.
SEQ ID NO: 212 is a genomic sequence derived from *Glycine max* corresponding to maturity locus 8.
SEQ ID NO: 213 is a genomic sequence derived from *Glycine max* corresponding to maturity locus 8.
SEQ ID NO: 214 is a probe for the detection of the SNP of SEQ ID NO: 143.
SEQ ID NO: 215 is a probe for the detection of the SNP of SEQ ID NO: 143.
SEQ ID NO: 216 is a probe for the detection of the SNP of SEQ ID NO: 144.
SEQ ID NO: 217 is a probe for the detection of the SNP of SEQ ID NO: 144.
SEQ ID NO: 218 is a probe for the detection of the SNP of SEQ ID NO: 145.
SEQ ID NO: 219 is a probe for the detection of the SNP of SEQ ID NO: 145.
SEQ ID NO: 220 is a probe for the detection of the SNP of SEQ ID NO: 146.
SEQ ID NO: 221 is a probe for the detection of the SNP of SEQ ID NO: 146.
SEQ ID NO: 222 is a probe for the detection of the SNP of SEQ ID NO: 147.

SEQ ID NO: 223 is a probe for the detection of the SNP of SEQ ID NO: 147.
SEQ ID NO: 224 is a probe for the detection of the SNP of SEQ ID NO: 148.
SEQ ID NO: 225 is a probe for the detection of the SNP of SEQ ID NO: 148.
SEQ ID NO: 226 is a probe for the detection of the SNP of SEQ ID NO: 149.
SEQ ID NO: 227 is a probe for the detection of the SNP of SEQ ID NO: 149.
SEQ ID NO: 228 is a probe for the detection of the SNP of SEQ ID NO: 150.
SEQ ID NO: 229 is a probe for the detection of the SNP of SEQ ID NO: 150.
SEQ ID NO: 230 is a probe for the detection of the SNP of SEQ ID NO: 151.
SEQ ID NO: 231 is a probe for the detection of the SNP of SEQ ID NO: 151.
SEQ ID NO: 232 is a probe for the detection of the SNP of SEQ ID NO: 152.
SEQ ID NO: 233 is a probe for the detection of the SNP of SEQ ID NO: 152.
SEQ ID NO: 234 is a probe for the detection of the SNP of SEQ ID NO: 153.
SEQ ID NO: 235 is a probe for the detection of the SNP of SEQ ID NO: 153.
SEQ ID NO: 236 is a probe for the detection of the SNP of SEQ ID NO: 154.
SEQ ID NO: 237 is a probe for the detection of the SNP of SEQ ID NO: 154.
SEQ ID NO: 238 is a probe for the detection of the SNP of SEQ ID NO: 155.
SEQ ID NO: 239 is a probe for the detection of the SNP of SEQ ID NO: 155.
SEQ ID NO: 240 is a probe for the detection of the SNP of SEQ ID NO: 156.
SEQ ID NO: 241 is a probe for the detection of the SNP of SEQ ID NO: 156.
SEQ ID NO: 242 is a probe for the detection of the SNP of SEQ ID NO: 157.
SEQ ID NO: 243 is a probe for the detection of the SNP of SEQ ID NO: 157.
SEQ ID NO: 244 is a probe for the detection of the SNP of SEQ ID NO: 158.
SEQ ID NO: 245 is a probe for the detection of the SNP of SEQ ID NO: 158.
SEQ ID NO: 246 is a probe for the detection of the SNP of SEQ ID NO: 159.
SEQ ID NO: 247 is a probe for the detection of the SNP of SEQ ID NO: 159.
SEQ ID NO: 248 is a probe for the detection of the SNP of SEQ ID NO: 160.
SEQ ID NO: 249 is a probe for the detection of the SNP of SEQ ID NO: 160.
SEQ ID NO: 250 is a probe for the detection of the SNP of SEQ ID NO: 161.
SEQ ID NO: 251 is a probe for the detection of the SNP of SEQ ID NO: 161.
SEQ ID NO: 252 is a probe for the detection of the SNP of SEQ ID NO: 162.
SEQ ID NO: 253 is a probe for the detection of the SNP of SEQ ID NO: 162.
SEQ ID NO: 254 is a probe for the detection of the SNP of SEQ ID NO: 163.
SEQ ID NO: 255 is a probe for the detection of the SNP of SEQ ID NO: 163.
SEQ ID NO: 256 is a probe for the detection of the SNP of SEQ ID NO: 164.
SEQ ID NO: 257 is a probe for the detection of the SNP of SEQ ID NO: 164.
SEQ ID NO: 258 is a probe for the detection of the SNP of SEQ ID NO: 165.
SEQ ID NO: 259 is a probe for the detection of the SNP of SEQ ID NO: 165.
SEQ ID NO: 260 is a probe for the detection of the SNP of SEQ ID NO: 166.
SEQ ID NO: 261 is a probe for the detection of the SNP of SEQ ID NO: 166.
SEQ ID NO: 262 is a probe for the detection of the SNP of SEQ ID NO: 167.
SEQ ID NO: 263 is a probe for the detection of the SNP of SEQ ID NO: 167.
SEQ ID NO: 264 is a probe for the detection of the SNP of SEQ ID NO: 168.
SEQ ID NO: 265 is a probe for the detection of the SNP of SEQ ID NO: 168.
SEQ ID NO: 266 is a probe for the detection of the SNP of SEQ ID NO: 169.
SEQ ID NO: 267 is a probe for the detection of the SNP of SEQ ID NO: 169.
SEQ ID NO: 268 is a probe for the detection of the SNP of SEQ ID NO: 170.
SEQ ID NO: 269 is a probe for the detection of the SNP of SEQ ID NO: 170.
SEQ ID NO: 270 is a probe for the detection of the SNP of SEQ ID NO: 171.
SEQ ID NO: 271 is a probe for the detection of the SNP of SEQ ID NO: 171.
SEQ ID NO: 272 is a probe for the detection of the SNP of SEQ ID NO: 172.
SEQ ID NO: 273 is a probe for the detection of the SNP of SEQ ID NO: 172.
SEQ ID NO: 274 is a probe for the detection of the SNP of SEQ ID NO: 173.
SEQ ID NO: 275 is a probe for the detection of the SNP of SEQ ID NO: 173.
SEQ ID NO: 276 is a probe for the detection of the SNP of SEQ ID NO: 174.
SEQ ID NO: 277 is a probe for the detection of the SNP of SEQ ID NO: 174.
SEQ ID NO: 278 is a probe for the detection of the SNP of SEQ ID NO: 175.
SEQ ID NO: 279 is a probe for the detection of the SNP of SEQ ID NO: 175.
SEQ ID NO: 280 is a probe for the detection of the SNP of SEQ ID NO: 176.
SEQ ID NO: 281 is a probe for the detection of the SNP of SEQ ID NO: 176.
SEQ ID NO: 282 is a probe for the detection of the SNP of SEQ ID NO: 177.
SEQ ID NO: 283 is a probe for the detection of the SNP of SEQ ID NO: 177.
SEQ ID NO: 284 is a probe for the detection of the SNP of SEQ ID NO: 178.
SEQ ID NO: 285 is a probe for the detection of the SNP of SEQ ID NO: 178.
SEQ ID NO: 286 is a probe for the detection of the SNP of SEQ ID NO: 179.
SEQ ID NO: 287 is a probe for the detection of the SNP of SEQ ID NO: 179.
SEQ ID NO: 288 is a probe for the detection of the SNP of SEQ ID NO: 180.

SEQ ID NO: 289 is a probe for the detection of the SNP of SEQ ID NO: 180.
SEQ ID NO: 290 is a probe for the detection of the SNP of SEQ ID NO: 181.
SEQ ID NO: 291 is a probe for the detection of the SNP of SEQ ID NO: 181.
SEQ ID NO: 292 is a probe for the detection of the SNP of SEQ ID NO: 182.
SEQ ID NO: 293 is a probe for the detection of the SNP of SEQ ID NO: 182.
SEQ ID NO: 294 is a probe for the detection of the SNP of SEQ ID NO: 183.
SEQ ID NO: 295 is a probe for the detection of the SNP of SEQ ID NO: 183.
SEQ ID NO: 296 is a probe for the detection of the SNP of SEQ ID NO: 184.
SEQ ID NO: 297 is a probe for the detection of the SNP of SEQ ID NO: 184.
SEQ ID NO: 298 is a probe for the detection of the SNP of SEQ ID NO: 185.
SEQ ID NO: 299 is a probe for the detection of the SNP of SEQ ID NO: 185.
SEQ ID NO: 300 is a probe for the detection of the SNP of SEQ ID NO: 186.
SEQ ID NO: 301 is a probe for the detection of the SNP of SEQ ID NO: 186.
SEQ ID NO: 302 is a probe for the detection of the SNP of SEQ ID NO: 187.
SEQ ID NO: 303 is a probe for the detection of the SNP of SEQ ID NO: 187.
SEQ ID NO: 304 is a probe for the detection of the SNP of SEQ ID NO: 188.
SEQ ID NO: 305 is a probe for the detection of the SNP of SEQ ID NO: 188.
SEQ ID NO: 306 is a probe for the detection of the SNP of SEQ ID NO: 189.
SEQ ID NO: 307 is a probe for the detection of the SNP of SEQ ID NO: 189.
SEQ ID NO: 308 is a probe for the detection of the SNP of SEQ ID NO: 190.
SEQ ID NO: 309 is a probe for the detection of the SNP of SEQ ID NO: 190.
SEQ ID NO: 310 is a probe for the detection of the SNP of SEQ ID NO: 191.
SEQ ID NO: 311 is a probe for the detection of the SNP of SEQ ID NO: 191.
SEQ ID NO: 312 is a probe for the detection of the SNP of SEQ ID NO: 192.
SEQ ID NO: 313 is a probe for the detection of the SNP of SEQ ID NO: 192.
SEQ ID NO: 314 is a probe for the detection of the SNP of SEQ ID NO: 193.
SEQ ID NO: 315 is a probe for the detection of the SNP of SEQ ID NO: 193.
SEQ ID NO: 316 is a probe for the detection of the SNP of SEQ ID NO: 194.
SEQ ID NO: 317 is a probe for the detection of the SNP of SEQ ID NO: 194.
SEQ ID NO: 318 is a probe for the detection of the SNP of SEQ ID NO: 195.
SEQ ID NO: 319 is a probe for the detection of the SNP of SEQ ID NO: 195.
SEQ ID NO: 320 is a probe for the detection of the SNP of SEQ ID NO: 196.
SEQ ID NO: 321 is a probe for the detection of the SNP of SEQ ID NO: 196.
SEQ ID NO: 322 is a probe for the detection of the SNP of SEQ ID NO: 197.
SEQ ID NO: 323 is a probe for the detection of the SNP of SEQ ID NO: 197.
SEQ ID NO: 324 is a probe for the detection of the SNP of SEQ ID NO: 198.
SEQ ID NO: 325 is a probe for the detection of the SNP of SEQ ID NO: 198.
SEQ ID NO: 326 is a probe for the detection of the SNP of SEQ ID NO: 199.
SEQ ID NO: 327 is a probe for the detection of the SNP of SEQ ID NO: 199.
SEQ ID NO: 328 is a probe for the detection of the SNP of SEQ ID NO: 200.
SEQ ID NO: 329 is a probe for the detection of the SNP of SEQ ID NO: 200.
SEQ ID NO: 330 is a probe for the detection of the SNP of SEQ ID NO: 201.
SEQ ID NO: 331 is a probe for the detection of the SNP of SEQ ID NO: 201.
SEQ ID NO: 332 is a probe for the detection of the SNP of SEQ ID NO: 202.
SEQ ID NO: 333 is a probe for the detection of the SNP of SEQ ID NO: 202.
SEQ ID NO: 334 is a probe for the detection of the SNP of SEQ ID NO: 203.
SEQ ID NO: 335 is a probe for the detection of the SNP of SEQ ID NO: 203.
SEQ ID NO: 336 is a probe for the detection of the SNP of SEQ ID NO: 204.
SEQ ID NO: 337 is a probe for the detection of the SNP of SEQ ID NO: 204.
SEQ ID NO: 338 is a probe for the detection of the SNP of SEQ ID NO: 205.
SEQ ID NO: 339 is a probe for the detection of the SNP of SEQ ID NO: 205.
SEQ ID NO: 340 is a probe for the detection of the SNP of SEQ ID NO: 206.
SEQ ID NO: 341 is a probe for the detection of the SNP of SEQ ID NO: 206.
SEQ ID NO: 342 is a probe for the detection of the SNP of SEQ ID NO: 207.
SEQ ID NO: 343 is a probe for the detection of the SNP of SEQ ID NO: 207.
SEQ ID NO: 344 is a probe for the detection of the SNP of SEQ ID NO: 208.
SEQ ID NO: 345 is a probe for the detection of the SNP of SEQ ID NO: 208.
SEQ ID NO: 346 is a probe for the detection of the SNP of SEQ ID NO: 209.
SEQ ID NO: 347 is a probe for the detection of the SNP of SEQ ID NO: 209.
SEQ ID NO: 348 is a probe for the detection of the SNP of SEQ ID NO: 210.
SEQ ID NO: 349 is a probe for the detection of the SNP of SEQ ID NO: 210.
SEQ ID NO: 350 is a probe for the detection of the SNP of SEQ ID NO: 211.
SEQ ID NO: 351 is a probe for the detection of the SNP of SEQ ID NO: 211.
SEQ ID NO: 352 is a probe for the detection of the SNP of SEQ ID NO: 212.
SEQ ID NO: 353 is a probe for the detection of the SNP of SEQ ID NO: 212.
SEQ ID NO: 354 is a probe for the detection of the SNP of SEQ ID NO: 213.

SEQ ID NO: 355 is a probe for the detection of the SNP of SEQ ID NO: 213.

DEFINITIONS

A "maturity group value" can be any indicative number, symbol, or combination of both that provides an indication of when a plant will mature.

A "dominant maturity allele" is an allele that, when present either in single copy (heterozygous) or two copies (homozygous), affects the maturity of the plant.

A "recessive maturity allele" is an allele that, when present in one copy (heterozygous), does not affect the maturity of a plant.

As used herein, determinate growth habit refers to ceasing of vegetative growth after the main stem terminates in a cluster of mature pods.

As used herein, indeterminate growth habit refers to the development of leaves and flowers simultaneously throughout a portion of their reproductive period, with one to three pods at the terminal apex.

As used herein, an allelic combination is the combination of alleles present at more than one characterized location or loci. An example of an allelic combination is allelic combination 10, which is homozygous dominant at maturity genomic region 1; homozygous recessive at maturity genomic region 2; and homozygous dominant at maturity genomic region 3.

As used herein, "line" refers to a group of individual plants from the similar parentage with similar traits. An "elite line" is any line that has resulted from breeding and selection for superior agronomic performance. Additionally, an elite line is sufficiently homogenous and homozygous to be used for commercial production. Elite lines may be used in the further breeding efforts to develop new elite lines. An elite plant is any plant from an elite line.

As used herein, "a trait" refers to an observable and/or measurable characteristic of an organism, such as a trait of a plant, for example, tolerance to an herbicide, insect and microbe. A trait can be conventional and transgenic. Non-limiting examples of traits include herbicide tolerance, increased yield, insect control, fungal disease resistance, virus resistance, nematode resistance, bacterial disease resistance, mycoplasma disease resistance, altered oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels.

As used herein, "a transgene" refers to a foreign gene that is placed into an organism by the process of plant transformation. In certain aspects, a soybean plant provided by the invention may comprise one or more transgene(s).

As used herein, "altered" means increased or decreased at maturity. In this aspect, a mature seed as defined by a seed that is harvested in the field for commercial agricultural practices, such as sale for feed. In an aspect, a soybean plants are selected for preferred geographies for expression of at least one phenotypic trait. The phenotypic trait includes altered levels of a substance or a molecule, such as proteins, oils, or gamma linolenic acid. "Altered" can include any relative increase or decrease of function or production of a gene product of interest, in an aspect up to and including complete elimination of function or production of that gene product. When levels of a gene product are compared, such a comparison is preferably carried out between organisms with a similar genetic background. Preferably, a similar genetic background is a background where the organisms being compared share 50% or greater, more preferably 75% or greater, and, even more preferably 90% or greater sequence identity of nuclear genetic material. In another aspect, a similar genetic background is a background where the plants are isogenic except for one or more markers of the present invention.

As used herein, a "cultivar" is a race or variety of a plant that has been created or selected intentionally and maintained through cultivation.

As used herein, the term "tissue culture" indicates a composition comprising isolated cells of the same or a different type or a collection of such cells organized into parts of a plant.

DETAILED DESCRIPTION OF THE INVENTION

Determination of the maturity group value of a soybean plant or seed is important in selecting where a soybean plant should be grown. An aspect of the present invention provides for a method of establishing where a plant or seed should be grown. A suitable region of a soybean plant or seed can be established. Establishment of a region can include selection of a suitable maturity belt region. Maturity belts range in the United States from 000 in the extreme northern U.S. to VIII in the southern Gulf Coast states. The present invention can also be used to determine other maturity belts including IX and X. The present invention can further be utilized to determine whether a plant is suitable for one, two, or more maturity belts or regions.

A suitable geographic region can be selected using a method of the present invention. In addition to maturity belts, other geographic regions that can be selected include maturity group 0 regions, such as and without limitation, Western Maine, North Dakota, Central Montana, Northwestern Oregon; maturity group 1 regions, such as and without limitation, northern Wisconsin, South Dakota; maturity group 2 regions, such as and without limitation, Vermont, Southern Massachusetts, Northern Connecticut, New York, Central Florida, Michigan, Northern Illinois, Southern Wisconsin, Iowa, Nebraska, Colorado, Central California; maturity group 3 regions, such as and without limitation, Western New Hampshire, Pennsylvania, Ohio, Indiana, Southern Illinois, Northern Missouri, Kansas, Southeast Wyoming, Colorado; maturity group 4 regions, such as and without limitation, Maryland, Northern Virginia, Kentucky, Western West Virginia, Central Missouri, Texas, Western Oklahoma; maturity group 5 regions, such as and without limitation, Central Virginia, North Carolina, Central and Western North Carolina, Mississippi, Louisiana, Tennessee; maturity group 6 regions, such as and without limitation, North Carolina, Eastern South Carolina; and maturity group 7 regions, such as and without limitation, Georgia, and Alabama. In another aspect, a seed of the present invention can be sent to a geographic region that is desirable to optimize a trait, such as yield.

The present invention also provides methods of selecting a suitable geographic region and methods for determining the maturity group of a soybean plant or seed by genotypic analysis. One aspect of the present invention includes a method of establishing where a soybean plant should be grown by obtaining DNA from the soybean plant; and determining if an allele within maturity genomic region 1 is homozygous or heterozygous using marker SEQ ID NO: 151.

The present invention allows the determination of allelic combinations. Allelic combinations can be any combination of alleles. In one aspect, it can be a combination of 2, 3, 4, 5, 6, 7, or 8 pairs of alleles that occupy a genetic locus. In another aspect, the alleles can be located within 2, 3, 4, 5, 6, 7, or 8 or more maturity genomic regions. Such maturity regions can be selected from maturity genomic region 1, maturity genomic region 2, maturity genomic region 3, maturity genomic region 4, maturity genomic region 5, maturity genomic region 6, maturity genomic region 7, or maturity genomic region 8, etc.

Alleles at any combination of maturity regions can be determined individually or in combination. One illustrative combination is a combination of more than one pair of alleles at maturity regions 1, 2, and 3. Another illustrative combination is a combination of more than one pair of alleles at maturity regions 1 and 2. "Allelic combinations" is intended to include, without limitation, any of homozygous dominant, homozygous recessive, and heterozygous alternatives at a particular locus.

Determination of an allele or the combination of alleles at a locus or loci can be carried out by any appropriate methodology. In an aspect, various assays can be used, such as a Taq-Man® assay, Real Time PCR, and nucleic acid sequencing, and simple sequence repeat mapping, to detect the genotype. In an aspect of the present invention, the assay includes a nucleic acid molecule of the present invention. Nucleic acids include deoxynucleic acids (DNA) and ribonucleic acids (RNA) and functionally equivalent analogues thereof.

Nucleic acids for use in the present invention can be obtained from a plant, such as from a plant part which includes a leaf, vascular tissue, flower, pod, seed, root, stem, or a portion of any.

In one aspect, nucleic acids are obtained from a plant or plant part using a non-destructive method. In an aspect, the plant part is a seed. In an aspect, the nucleic acids are obtained from a seed in a non-destructive manner, which provides for a seed that is viable. For example, DNA can be obtained from a seed by chipping the seed with a sharp knife at a part furthest away from the 'eye' or by pricking carefully with a needle to puncture the seed. Any method that will obtain DNA for analysis or allow in situ analysis of the DNA can be used provided that the plant or plant part retains the ability to grow. If DNA is taken from a seed and the seed is still viable, the method can be considered non-destructive. Exemplary methods to sample seeds without affecting the germination viability of the seeds are detailed in US Patent Application Publication 20060042527A1, hereby incorporated by reference. In an aspect, seeds are sampled by feeding the seeds individually to a sampling station, removing a sample from the seed in the sampling station, conveying the sample to a compartment in a sample tray and conveying the seed to a corresponding compartment in a seed tray.

In an aspect, the maturity genomic region associated with plant maturity and plant growth habit of the present invention is introduced or selected within the genus *Glycine*. The genus *Glycine* includes the wild perennial soybeans and have a wide array of genetic diversity. For example, the cultivated soybean (*Glycine max* (L.) Merr.) and its wild annual progenitor (*Glycine soja* (Sieb. and Zucc.)) belong to the subgenus *Soja*, contain 2n=40 chromosomes, are cross-compatible, usually produce vigorous fertile $F_1$ hybrids, and carry similar genomes. Crosses between cultivated *Glycine* species and wild perennial *Glycine* species have variable success among accessions.

The present invention further provides that the selected plant is from the group consisting of members of the genus *Glycine*, more specifically from the group consisting of *Glycine arenaria, Glycine argyrea, Glycine canescens, Glycine clandestine, Glycine curvata, Glycine cyrtoloba, Glycine falcate, Glycine latifolia, Glycine latrobeana, Glycine max, Glycine microphylla, Glycine pescadrensis, Glycine pindanica, Glycine rubiginosa, Glycine soja, Glycine* sp., *Glycine stenophita, Glycine tabacina*, and *Glycine tomentella*. In an aspect the plant of the present invention is selected from an elite *Glycine max* line.

The present invention also provides a soybean plant selected for a desired plant maturity by screening for a maturity marker in the soybean plant or seed, the selection comprising assaying genomic nucleic acids for the presence of a marker molecule that is genetically linked to a genomic region associated with a plant maturity in the soybean plant, where the genomic region is also located on a linkage group associated with a soybean plant of a preferred plant maturity.

Methods of the present invention include determining if a locus contains a polymorphism, or is homozygous or heterozygous at a maturity region selected from maturity genomic region 1, maturity genomic region 2, maturity genomic region 3, maturity genomic region 4, maturity genomic region 5, maturity genomic region 6, maturity genomic region 7, and/or maturity genomic region 8 by detecting a polymorphism within a nucleic acid molecule comprising a sequence or fragment thereof selected from the group consisting of SEQ ID NOs: 143-174, or complements thereof. The present invention includes the identification of alleles at eight maturity group regions. These regions are termed maturity genomic regions 1 through 8.

The state of homozygosity or heterozygosity and dominance or recessivity of maturity genomic region 1 can be monitored by assaying for an allele of 1, 2, 3, 4, 5, 6, 7, 8, 9, 10, 11, 12, or 13 or more genetic markers selected from the group consisting of NS0093385, NS0093976, NS0096829, NS0097798, NS0098982, NS00995929, NS0099746, NS0103749, NS0123747, NS0124601, NS0125408, NS0128378, and NS0135390. SNP marker DNA sequences for region 1 include those presented as SEQ ID NO: 143 through SEQ ID NO: 155 and can be amplified using the primers indicated as SEQ ID NO: 1 through SEQ ID NO: 26 with probes indicated as SEQ ID NO: 214 through SEQ ID NO: 239. In another aspect, a maturity genomic region 1 is a region associated with SEQ ID NOs: 143-149, 154-155. In another aspect, a maturity genomic region 1 is a region associated with SEQ ID NO: 149 or SEQ ID NO: 151 or both. In an aspect, maturity genomic region 1 can span 1 centiMorgan (cM), 5 cM, 10 cM, 15 cM, 20 cM, or 30 cM either side of SEQ ID NO: 149 or SEQ ID NO: 151.

An aspect of the present invention includes a method of determining if a soybean seed will grow into a soybean plant having a maturity group of III-VI by determining a homozygous or heterozygous marker within the soybean seed using a marker with the nucleic acid sequence of SEQ ID NO: 151. In a preferred aspect, the homozygous marker can be recessive or dominant. In another preferred aspect, the maturity of the plant is delayed where the marker is homozygous dominant.

Another aspect of the present invention includes a method of determining if a soybean seed will grow into a soybean plant having a maturity group between 0.0-III.0 comprising determining if an 11-basepair insertion within the nucleic acid sequence of SEQ ID NO: 149 exists in the soybean seed.

The state of homozygosity or heterozygosity and dominance or recessivity of maturity genomic region 2 may be monitored by assaying for an allele of 1, 2, 3, 4, 5, or 6 or more genetic markers including those selected from the group consisting of NS0118907, NS0122182, NS0126989, NS097952, NS0123506 and NS0095677. SNP marker DNA sequences for region 2 include those presented as SEQ ID NO: 156 through SEQ ID NO: 161 and can be amplified using the primers indicated as SEQ ID NO: 27 through SEQ ID NO: 38 with probes indicated as SEQ ID NO: 240 through SEQ ID NO: 251. In another aspect, a maturity genomic region 2 is a region associated with SEQ ID NO: 158. In another aspect, a maturity genomic region 2 is a region associated with SEQ ID NOs: 156-161. In an aspect, maturity genomic region 2 can span 1 cM, 5 cM, 10 cM, 15 cM, 20 cM, or 30 cM either side of SEQ ID NO: 158.

The state of homozygosity or heterozygosity and dominance or recessivity of maturity genomic region 3 may be monitored by assaying for an allele of 1, 2, 3, 4, 5, 6, 7, 8, 9, 10, 11, 12, or 13 or more genetic markers including those selected from the group consisting of NS0098853, NS0092561, NS0093197, NS0094891, NS0096225, NS0103853, NS0113929, NS0115535, NS0121511, NS0136544, NS0119569, NS0123708, and NS0114317. SNP marker DNA sequences for region 3 including those presented as SEQ ID NO: 162 through SEQ ID NO: 174 and can be amplified using the primers indicated as SEQ ID NO: 39 through SEQ ID NO: 64 with probes indicated as SEQ ID NO: 252 through SEQ ID NO: 277. In another aspect, a maturity genomic region 3 is a region associated with SEQ ID NOs: 164, 167, 171-174. In another aspect, a maturity genomic region 3 is a region associated with SEQ ID NO: 169. In an aspect, maturity genomic region 3 can span 1 cM, 5 cM, 10 cM, 15 cM, 20 cM, or 30 cM either side of SEQ ID NO: 169.

The state of homozygosity or heterozygosity and dominance or recessivity of maturity genomic region 4 may be monitored by assaying for an allele of 1, 2, 3, 4, 5, or 6 or more genetic markers including those selected from the group consisting of NS0092743, NS0098176, NS0100078, NS0137415, NS0095530, and NS0129004. SNP marker DNA sequences for region 4 are presented as SEQ ID NO: 175 through SEQ ID NO: 180 and can be amplified using the primers indicated as SEQ ID NO: 65 through SEQ ID NO: 76 with probes indicated as SEQ ID NO: 278-289. In another aspect, a maturity genomic region 4 is a region associated with SEQ ID NO: 178. In an aspect, maturity genomic region 4 can span 1 cM, 5 cM, 10 cM, 15 cM, 20 cM, or 30 cM either side of SEQ ID NO: 178. An aspect of the present invention includes a method of detecting maturity genomic region 4 by detecting an allele using a marker selected from any of SEQ ID NO: 175-180.

The state of homozygosity or heterozygosity and dominance or recessivity of maturity genomic region 5 may be monitored by assaying for an allele of 1, 2, 3, 4, 5, 6, 7, 8, or 9 or more genetic markers including those selected from the group consisting of NS0120015, NS0113878, NS0101863, NS0115066, NS0123168, NS0119165, NS0123724, NS0103446, and NS0099024. SNP marker DNA sequences for region 5 including those presented as SEQ ID NO: 181 through SEQ ID NO: 189 and can be amplified using the primers indicated as SEQ ID NO: 77 through SEQ ID NO: 94 with probes indicated as SEQ ID NO: 290 through SEQ ID NO: 307. In another aspect, a maturity genomic region 5 is a region associated with SEQ ID NO: 187. In an aspect, maturity genomic region 5 can span 1 cM, 5 cM, 10 cM, 15 cM, 20 cM, or 30 cM either side of SEQ ID NO: 187. An aspect of the present invention includes a method of detecting maturity genomic region 5 by detecting an allele using a marker selected from any of SEQ ID NO: 181-189.

The state of homozygosity or heterozygosity and dominance or recessivity of maturity genomic region 6 may be monitored by assaying for an allele of 1, 2, 3, 4, 5, 6, or 7 or more genetic markers including those selected from the group consisting of NS0116125, NS0125770, NS0103755, NS0125713, NS0124590, NS0119281, and NS0102717. SNP marker DNA sequences for region 6 including those presented as SEQ ID NO: 190 through SEQ ID NO: 196 and can be amplified using the primers indicated as SEQ ID NO: 95 through SEQ ID NO: 108 with probes indicated as SEQ ID NO: 308 through SEQ ID NO: 321. In another aspect, a maturity genomic region 6 is a region associated with SEQ ID NO: 192. In an aspect, maturity genomic region 6 can span 1 cM, 5 cM, 10 cM, 15 cM, 20 cM, or 30 cM either side of SEQ ID NO: 192. An aspect of the present invention includes a method of detecting maturity genomic region 6 by detecting an allele using a marker selected from any of SEQ ID NO: 190-196.

The state of homozygosity or heterozygosity and dominance or recessivity of maturity genomic region 7 may be monitored by assaying for an allele of 1, 2, 3, 4, 5, 6, or 7 or more genetic markers including those selected from the group consisting of NS0095211, NS0099531, NS0099417, NS0097307, NS0103004, NS0102630, and NS0102915. SNP DNA sequences for region 7 including those presented as SEQ ID NO: 197 through SEQ ID NO: 203 and can be amplified using the primers indicated as SEQ ID NO: 109 through SEQ ID NO: 122 with probes indicated as SEQ ID NO: 322 through SEQ ID NO: 335. In another aspect, a maturity genomic region 7 is a region associated with SEQ ID NO: 202. In an aspect, maturity genomic region 7 can span 1 cM, 5 cM, 10 cM, 15 cM, 20 cM, or 30 cM either side of SEQ ID NO: 202. An aspect of the present invention includes a method of detecting maturity genomic region 7 by detecting an allele using a marker selected from any of SEQ ID NO: 197-203.

The state of homozygosity or heterozygosity and dominance or recessivity of maturity genomic region 8 may be monitored by assaying for an allele of 1, 2, 3, 4, 5, 6, 7, 8, 9, or 10 or more genetic markers including those selected from the group consisting of N0102362, NS0100652, NS017716, NS0119574, NS0127728, NS0099639, NS0103255, NS0119106, NS0101020, and NS0101779. SNP DNA sequences for region 8 including those presented as SEQ ID NO: 204 through SEQ ID NO: 213 and can be amplified using the primers indicated as SEQ ID NO: 123 through SEQ ID NO: 142 with probes indicated as SEQ ID NO: 336 through SEQ ID NO: 355. In another aspect, a maturity genomic region 8 is a region associated with SEQ ID NO: 204. In an aspect, maturity genomic region 8 can span 1 cM, 5 cM, 10 cM, 15 cM, 20 cM, or 30 cM either side of SEQ ID NO: 204. An aspect of the present invention includes a method of detecting maturity genomic region 8 by detecting an allele using a marker selected from any of SEQ ID NO: 204-213.

Nucleic acid molecules of the present invention or fragments thereof are capable of specifically hybridizing to other nucleic acid molecules, also included in the present invention, under certain circumstances. In an aspect, the nucleic acid molecules of the present invention contain any of SEQ ID NO: 143-213, complements thereof and fragments of any. In another aspect, the nucleic acid molecules of the present invention include nucleic acid molecules that hybridize, for example, under high or low stringency, substantially homologous sequences, or that have both to these molecules. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual, 2nd Edition*, Cold Spring Harbor Press, Cold Spring Harbor, N.Y. (1989)), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa, *Nucl. Acids Res.* 12:203-213, 1984; and Wetmur and Davidson, *J. Mol. Biol.* 31:349-370, 1968. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5× Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments. Detection of DNA segments via hybridization is well-known to those of skill in the art, and thus depending on the application envisioned, one will desire to employ varying hybridization conditions to achieve varying degrees of selectivity of probe towards target sequence and the method of choice will depend on the desired results.

As used herein, an agent, be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al., *Science* 238:336-340 (1987); European Patent No. 144914), chemical labels (U.S. Pat. No. 4,582,789; U.S. Pat. No. 4,563,417), modified bases (European Patent No. 119448), all of which are herein incorporated by reference in their entirety).

In an aspect, an agent of the present invention will specifically hybridize to one or more of the nucleic acid molecules set forth in SEQ ID NO: 143 through SEQ ID NO: 213 or complements thereof or fragments of either under moderately stringent conditions, for example at about 2.0×SSC and about 65° C. In an aspect, a nucleic acid of the present invention will specifically hybridize to one or more of the nucleic acid molecules set forth in SEQ ID NO: 143 through SEQ ID NO: 213 or complements or fragments of either under high stringency conditions.

Agents of the present invention include genetic markers. Examples of such markers include nucleic acid molecules comprising nucleic acid sequences selected from the group consisting of SEQ ID NOs: 143-213. Examples of public marker databases include, for example: Soybase, an Agricultural Research Service, and United States Department of Agriculture. Other genetic markers are disclosed within.

Agents of the present invention include fragment nucleic acid molecules of the present invention. Fragments can contain significant portions of, or indeed most of, SEQ ID NOs: 143-213. In an aspect, the fragments are between 100 and 200 consecutive residues, 150 and 300 consecutive residues, 50 and 150 consecutive residues, or 20 and 50 consecutive residues long of a nucleic molecule of the present invention. In another aspect, the fragment comprises at least 50, 100, 200, 300, 400, or 500 consecutive residues of SEQ ID NOs: 143-213. In an aspect, a fragment nucleic acid molecule is capable of selectively hybridizing to SEQ ID NOs: 143-213.

In one aspect of the present invention, a preferred marker nucleic acid molecule of the present invention has the nucleic acid sequence set forth in SEQ ID NO: 143 through. SEQ ID NO: 213 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 143 through SEQ ID NO: 213 or complement thereof or fragments of either. In a further aspect of the present invention, a preferred marker nucleic acid molecule of the present invention shares between 95% and 100% sequence identity with the sequence set forth in SEQ ID NO: 143 through SEQ ID NO: 213 or complement thereof or fragments of either. In an aspect of the present invention, a preferred marker nucleic acid molecule of the present invention shares between 98% and 100% sequence identity with the nucleic acid sequence set forth in SEQ ID NO: 143 through SEQ ID NO: 213 or complement thereof or fragments of either.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

The present invention further provides one or more single nucleotide polymorphism (SNP) markers. The detection of polymorphic sites in a sample of DNA, RNA, or cDNA may be facilitated through the use of nucleic acid amplification methods. Such methods include those that specifically increase the concentration of polynucleotides that span the polymorphic site, or include that site and sequences located either distal or proximal to it. Such amplified molecules can be readily detected by gel electrophoresis or other means.

A method of achieving such amplification employs the polymerase chain reaction (PCR) (Mullis et al. 1986 Cold Spring Harbor Symp. Quant. Biol. 51:263-273; European Patent No. 50,424; European Patent No. 84,796; European Patent No. 258,017; European Patent No. 237,362; European Patent No. 201,184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Alleles that associate with plant maturity can be determined based on linkage analysis of plants and nucleic acid molecules of the present invention. A number of molecular genetic maps of *Glycine* have been reported (Mansur et al., *Crop Sci.* 36: 1327-1336 (1996); Shoemaker et al., *Genetics* 144: 329-338 (1996); Shoemaker et al., *Crop Science* 32: 1091-1098 (1992), Shoemaker et al., *Crop Science* 35: 436-446 (1995); Tinley and Rafalski, *J. Cell Biochem. Suppl.* 14E: 291 (1990); Cregan et al., *Crop Science* 39:1464-1490 (1999)). *Glycine max, Glycine soja* and *Glycine max* x. *Glycine soja* share linkage groups (Shoemaker et al., *Genetics* 144: 329-338 (1996)). A linkage group (LG) is a set of genes that tend to be inherited together from generation to generation. As used herein, reference to the linkage groups (LG), D1b; C2; O; L; and I and of *Glycine max* refers to the linkage group that corresponds to linkage groups, D1b, C2, O, L; and I from the genetic map of *Glycine max* (Mansur et al., *Crop Science.* 36: 1327-1336 (1996)); Cregan et al., *Crop Science* 39:1464-1490 (1999), and Soybase, Agricultural Research Service, United States Department of Agriculture.

Genome-wide surveys revealed SNP markers associated with maturity genomic region 1 are located on linkage group (LG) C2, maturity genomic region 2 is located on LG O, maturity genomic region 3 is located on LG L, maturity genomic region 4 is located on LG I, maturity genomic region 5 is located on LG L, maturity genomic region 6 is located on LG D1b+W, maturity genomic region 7 is located on LG G, and maturity genomic region 8 is located on LG M.

In an aspect, the present invention can be used to identify additional markers associated with maturity genomic regions 1-8. The present invention includes a maturity marker within 1 cM, 5 cM, 10 cM, 15 cM, or 30 cM of SEQ ID NO: 143-213. Similarly, one or more markers mapped within 1, 5, 10, 20 and 30 cM or less from the marker molecules of the present invention can be used for the selection or introgression of the region associated with maturity and/or plant growth habit. The present invention includes a maturity marker that is linked with SEQ ID NO: 143-213 and delays maturity. The present invention includes a substantially purified nucleic acid molecule comprising a maturity marker within 5 kilobases, 10 kilobases, 20 kilobases, 30 kilobases, 100 kilobases, 500 kilobases, 1,000 kilobases, 10,000 kilobases, 25,000 kilobases, or 50,000 kilobases of a marker selected from the group consisting of SEQ ID NO: 143-213. The present invention includes a maturity marker within 5 kilobases, 10 kilobases, 20 kilobases, 30 kilobases, 100 kilobases, 500 kilobases, 1,000 kilobases, 10,000 kilobases, 25,000 kilobases, or 50,000 kilobases of any of SEQ ID NO: 143-213 that cosegregates with any of SEQ ID NO: 143-213. Similarly, one or more markers mapped within 5 kilobases, 10 kilobases, 20 kilobases, 30 kilobases, 100 kilobases, 500 kilobases, 1,000 kilobases, 10,000 kilobases, 25,000 kilobases, or 50,000 kilobases or less from the marker molecules of the present invention can be used for the selection or introgression of the region associated with maturity and/or plant growth habit.

A maturity genomic region is a physical region of a plant chromosome that has been associated with determining a plant's maturity date. A plant is considered mature when 95% of its pods have reached their mature color. In one aspect of the present invention, the maturity date of a plant is the number of days after August 31$^{st}$ in the northern hemisphere. Alleles of maturity genomic regions 1-8 can influence the maturity date of a plant.

In one aspect, the maturity date of a plant can determine the maturity group of a plant. Herein, relative maturity refers to a soybean plant maturity group subdividing a maturity group into tenths, for example III.5. Relative maturity provides a more exact description of plant maturity. The number following the decimal point refers to the relative earliness or lateness with a maturity group, for example, IV.2 is an early group IV variety and IV.9 is a late group IV.

In another aspect, maturity group can be determined by reference to a commercialized strain for a maturity group. For example, a commercialized strain with a known maturity group is grown in an experiment with a new soybean line and the relative maturity of the new soybean line is ascertained by counting the number of days after August 31st and comparing to the commercialized strain. Maturity group refers to an industry division of groups of varieties based on a range in latitudes which the plant is best adapted and most productive. Soybean varieties are classified into 13 recognized maturity groups with the designations ranging from maturity groups 000, 00, 0, and I through X, where 000 represents the earliest maturing variety and X represents the latest maturing variety. The maturity groups have corresponding maturity belts.

Soybean plants in maturity groups 000 to IV have an indeterminate plant habit, while soybean plants in maturity groups V through X have a determinate plant habit. Early maturity varieties (000 to III) are adapted to northern latitudes with longer day lengths with the maturity designation increasing in southern latitudes with shorter day lengths.

An increase in maturity can correlate with an increase in yield or other traits such as oil concentration. The correlation of plant maturity and other traits confounds the evaluation of potential markers and candidate genes associated with other traits such as yield. Identification of genomic regions associated with plant maturity, but not with another trait, can allow breeders to genetically fix plant maturity within a soybean plant and separately elucidate other traits, such as those associated with yield.

The present invention includes a method of establishing where a soybean plant or soybean seed should be grown by determining the allelic combination of a soybean plant or soybean seed by obtaining DNA from a soybean plant or soybean seed; determining if alleles at a locus within maturity genomic region 1 are homozygous or heterozygous; determining if alleles at a locus within maturity genomic region 2 are homozygous or heterozygous; determining if alleles at a locus within maturity genomic region 3 are homozygous or heterozygous; determining the allelic combination of the alleles within maturity genomic regions 1, 2, and 3; and assigning a maturity group value to the soybean plant or soybean seed. In a preferred aspect, determining if alleles at a locus are homozygous or heterozygous includes detecting a polymorphism with a nucleic acid molecule having a sequence of any of SEQ ID NOs: 143-174, or complements thereof.

In another aspect, the present invention includes a method of establishing where a soybean plant or soybean seed should be grown by determining the allelic combination of a soybean plant or soybean seed by obtaining DNA from a soybean plant or soybean seed; determining if alleles at a locus within maturity genomic region 1 are homozygous or heterozygous; determining if alleles at a locus within maturity genomic region 2 are homozygous or heterozygous; determining if alleles at a locus within maturity genomic region 3 are homozygous or heterozygous; determining if alleles at a locus within maturity genomic region 2 are homozygous or heterozygous; determining the allelic combination of the alleles within maturity genomic regions 1, 2, 3 and 4; and assigning a maturity group value to the soybean plant or soybean seed.

The present invention also includes a method of providing information about the maturity of a soybean plant or soybean seed by obtaining DNA from the soybean seed or soybean plant and determining the allelic profile at a locus of genomic region 4.

The present invention also includes a method of establishing where a soybean plant or soybean seed should be grown by determining the allelic combination of a soybean plant or soybean seed by obtaining DNA from a soybean plant or soybean seed; determining if an allele within maturity genomic region 1 is homozygous or heterozygous; determining if an allele within maturity genomic region 2 is homozygous or heterozygous; determining if an allele within maturity genomic region 3 is homozygous or heterozygous; and determining the allelic combination of the alleles within maturity genomics regions 1, 2, and 3.

In a preferred aspect, the soybean plant or soybean seed is homozygous for the alleles within maturity genomics regions 1, 2, and 3. In a preferred aspect, the homozygous alleles are either dominant or recessive. In another aspect, the soybean plant or soybean seed is homozygous for the alleles within maturity genomics regions 1 and 2. In a preferred aspect, the homozygous alleles are either dominant or recessive. In another aspect, the soybean plant or soybean seed is homozygous for the alleles within maturity genomics regions 2 and 3. In a preferred aspect, the homozygous alleles are either dominant or recessive. In another aspect, the soybean plant or soybean seed is heterozygous for the alleles within maturity genomics regions 1, 2, and 3. In another aspect, the soybean plant or soybean seed is heterozygous for the alleles within maturity genomics regions 1 and 2. In another aspect, the soybean plant or soybean seed is heterozygous for the alleles within maturity genomics regions 2 and 3. In a preferred aspect, the allelic combination is allelic combination 10, allelic combination 11, allelic combination 12, allelic combination 13, allelic combination 14, allelic combination 15, allelic combination 16, allelic combination 17, allelic combination 18, and allelic combination 19.

An aspect of the present invention includes a method of establishing where a soybean plant or soybean seed should be grown by determining the allelic combination of a soybean plant by obtaining DNA from a soybean plant or soybean seed; determining if an allele within maturity genomic region 1 is homozygous or heterozygous; determining if an allele within maturity genomic region 2 is homozygous or heterozygous; determining the allelic combination of the alleles within maturity genomic regions 1 and 2; and assigning a maturity growth value to the soybean plant or soybean seed. In a preferred aspect, determining whether an allele is homozygous or heterozygous includes detecting a polymorphism from any of SEQ ID NOs: 143-161. In a preferred aspect, the allelic combination is allelic combination 1, allelic combination 2, allelic combination 3, allelic combination 4, allelic combination 5, allelic combination 6, allelic combination 7, allelic combination 8, and allelic combination 9. In a preferred aspect, the soybean plant or soybean seed is obtained from a cross of an early maturity group parent soybean plant and a mid-maturity parent soybean plant. In a preferred aspect, the early maturity group parent soybean plant is between 00.0-I.0 and the mid-maturity parent soybean plant is between III.0-IV.9

An aspect of the present invention includes a method to determine if a soybean plant has a maturity group of 0.0-III.9 by determining if an allele within maturity genomic region 1 is homozygous or heterozygous; determining if an allele within maturity genomic region 2 is homozygous or heterozygous; and assigning a maturity group value for the soybean plant between 0.0-III.9. In a preferred aspect, maturity in the soybean plant is reached at least 5 days before a soybean plant that is homozygous dominant within maturity genomic region 1, homozygous dominant within maturity genomic region 2 and is grown under the same environmental conditions.

Another aspect of the present invention includes a method to determine if the maturity of a soybean plant is in a 00.0-III.0 maturity group by determining if an allele within maturity genomic region 1 is homozygous or heterozygous; determining if an allele within maturity genomic region 2 is homozygous or heterozygous; and assigning a maturity group value for the soybean plant between 00.0-III.0. In a preferred aspect, a selected soybean seed is homozygous recessive at maturity genomic region 1 and homozygous recessive at maturity genomic region 2 and has a maturity group between 0.5-II.0. In a preferred aspect, a soybean seed is selected that is homozygous recessive at maturity genomic region 1 and heterozygous dominant at maturity genomic region 2 and has a maturity group between I.5-II.9.

The present invention includes a method where the maturity group of a progeny plant is predicted by whether an allele in maturity genomic region 1 is homozygous dominant, homozygous recessive, or heterozygous and whether an allele in maturity genomic region 2 is homozygous dominant, homozygous recessive, or heterozygous. In an aspect, if the maturity group of a plant is between 0 and II, the maturity group can be identified by determining the allelic combination of maturity genomic regions 1 and 2 in a plant or seed. See, for example, Table 9.

In an alternate aspect, if the maturity group of a plant is between III and V, the maturity group can be identified by determining the allelic combination of maturity genomic regions 1, 2 and 3 in a plant or seed. See, for example, Table 9. In an aspect, if the maturity group of a plant is between IV and V, the maturity group can be identified by determining the allelic combination of maturity genomic regions 1, 2 and 3 in a plant or seed. See, for example, Table 9.

In another aspect, the maturity group of the parent plants is known. In an aspect, the maturity groups of the parent plants are different by more than 10 days, between 10 days—20 days, between 10 days-30 days, more than 2 maturity groups, less than 2 maturity groups, between maturity groups 000 and VI. In an aspect, the maturity group of a progeny plant resulting from a cross with at least one parent having a maturity group of 0-II is identified by determining the allelic combination of maturity genomic regions 1 and 2. In another aspect, the maturity group of a progeny plant resulting from a cross with parent plants having a maturity group of III, IV, V, or III-V is identified by determining the allelic combination of maturity genomic regions 1, 2 and 3.

In an aspect, more dominant alleles at a locus in a maturity group region correlate with a delay in maturity. In another aspect, an increase in the number of dominant alleles correlates with a delay in maturity.

In an aspect, parent plants with a difference in maturity group greater than 1.5, 2, 2.5, 3, 3.5 are crossed and their maturity group identified by determining the allelic combination. In an aspect, parent plants with a difference in maturity group between 1 and 3, between 1 and 4, between 2 and 3, between 2 and 5, between 2 and 6, between 2 and 7 are crossed and their maturity group identified by determining the allelic combination of the progeny. In an aspect, parent plants with a difference in maturity group greater than 1.5, 2, 2.5, 3, 3.5 are crossed and their maturity group identified by determining the allelic combination.

In an aspect, a progeny plant has a maturity group earlier than one parent by 5, 10, or 15 days. In another aspect a progeny plant has a maturity group later than one parent plant by 5, 10, or 15 days. In an aspect, a progeny plant has a maturity group earlier than both parents by 5, 10, or 15 days. In another aspect, a progeny plant has a maturity group later than both parent plants by 5, 10, or 15 days.

In an aspect, an early parent of maturity group 0.1 is crossed with a later maturity parent plant that is a 1.9, and the progeny plants with allelic combination 1 are 0.1-0.5 maturity. In another aspect, an early parent with maturity of 0.9 is crossed with a plant having 3.5 maturity, and the plants having allelic combination 1 are maturity group 1.0-1.5.

In an aspect, the maturity group of a progeny seed is determined from a cross between a very early maturity parent plant with a later maturity parent plant. In an aspect, the very early maturity parent plant is a maturity group 00.0-0.9 and the later maturity parent plant is a maturity group III.5-IV.5. In an aspect, the very early maturity parent plant is a maturity group 00 and the later maturity parent plant is a maturity group III or IV. In an aspect, DNA can be obtained from plants or plant parts such as seeds in the $F_1$, $F_2$, $F_3$, $F_4$ or later populations. In an aspect, one or more plants or plant parts are genotyped for alleles in genomic regions 1 and 2. In an aspect, the alleles are determined using the SNP markers NS0128378 (genomic maturity region 1) and NS0118907 (genomic maturity region 2).

In an aspect, the plants are phenotyped for maturity by counting the number of days after August $31^{st}$ until a plant matures. In an aspect, a plant is considered mature when 95% of the pods are brown. In an aspect, when alleles from markers associated with maturity genomic regions 1 and 2 are homozygous recessive, the progeny plant will reach maturity 15, 14, 12, 11, 10, 9, or 8 days sooner than the maturity group if the alleles from markers associated with maturity genomic regions 1 and 2 are homozygous dominant. In an aspect, if an allele from a marker associated with maturity genomic region 1 is homozygous dominant and an allele from a marker associated with maturity genomic region 2 is heterozygous, then the progeny plant will reach maturity between 1 day, 1-2 days, 2-3 days, 2-4 days, or 3-5 days earlier than if the alleles from markers associated with maturity genomic regions 1 and 2 are homozygous dominant.

In another aspect of the present invention, multiple seeds can be selected or bulked. Multiple seeds may include greater than or equal to 2, 3, 4, 5, 6, 10, 50, 100, 500, 1000, 5,000, 10,000 or more seeds. One or multiple seeds can be distributed to a geographic region suitable for growth of one or multiple plants. In this aspect, seeds selected can be distributed or shipped to an appropriate region.

The present invention also provides multiple soybean seeds in which greater than 50%, 60%, 70%, 80%, 90%, 95%, or 99% of the seeds will grow into plants where the variation in maturity group is within one maturity group, not more than 2 groups or 20 days after August $31^{st}$, not more than 1 group or 10 days after August $31^{st}$, not more than 0.9 group or nine days after August $31^{st}$, not more than 5 days after August $31^{st}$ or 0.5 group, or with a maturity group between 0.0-II.0, 000.0-III.9. The multiple soybean seeds can grow into soybean plants having indeterminate soybean plant habit or having determinate soybean plant habit. One aspect of the present invention includes a method to select a soybean seed based on indeterminate or determinate growth habit comprising determining if maturity genomic region 3 is homozygous or heterozygous. In one aspect, 85% of the multiple soybean seeds can reach maturity within 10 days, 5 days, 3 days of each other. In another aspect, 95% of the multiple soybean seeds can reach maturity within 10 days, 5 days, 3 days of each other.

Another aspect of the present invention includes a method to isolate indeterminate-early maturity soybean seeds by obtaining DNA from the soybean seed using a non-destructive method; determining if an allele within maturity genomic region 1 is homozygous or heterozygous; and determining if an allele within maturity genomic region 2 is homozygous or heterozygous.

Such multiple seeds may be in a container. The container of soybean seeds can contain any number, weight, or volume of seeds. For example, a container can contain at least, or greater than, about 10, 25, 50, 100, 200, 300, 400, 500, 600, 700, 80, 90, 1000, 1500, 2000, 2500, 3000, 3500, 4000, 5000, 7500, or 10,000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, 30 pounds, 40 pounds, 50 pounds, 60 pounds, 70 pounds, 80 pounds, 100 pounds, 200 pounds, 300 pounds, 500 pounds, or 1000 pounds or more seeds.

Containers of soybean seeds can be any container available in the art. For example, a container can be a box, a bag, a can, a packet, a pouch, a tape roll, a pail, or a tube.

In another aspect, the seeds contained in the containers of soybean seeds can be treated or untreated soybean seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coating can be any form of seed coating including, but not limited to, pelleting, film coating, and encrustments.

One aspect of the present invention includes a method of distributing a soybean plant based on maturity group by obtaining DNA from a soybean plant; determining if an allele within maturity genomic region 1 is homozygous or heterozygous; determining if an allele within maturity genomic region 2 is homozygous or heterozygous; determining if an allele within maturity genomic region 3 is homozygous or heterozygous; and assigning a maturity growth value to the soybean plant; and shipping the soybean plant to a preferred geographic region.

A plant of the invention may also comprise a gene that confers resistance to insect, pest, viral or bacterial attack. Such a gene may be a transgene. For example, a gene conferring resistance to a pest, such as soybean cyst nematode was described in U.S. Pat. No. 7,154,021, herein incorporated by reference.

Transgenes may also be used to alter protein metabolism. For example, U.S. Pat. No. 5,545,545, herein incorporated by reference, describes lysine-insensitive maize dihydrodipicolinic acid synthase (DHPS), which is substantially resistant to concentrations of L-lysine which otherwise inhibit the activity of native DHPS. Similarly, EP 0640141, herein incorporated by reference, describes sequences encoding lysine-insensitive aspartokinase (AK) capable of causing a higher than normal production of threonine, as well as a subfragment encoding antisense lysine ketoglutarate reductase for increasing lysine.

In another aspect, a transgene may be employed that alters plant carbohydrate metabolism. For example, fructokinase genes are known for use in metabolic engineering of fructokinase gene expression in transgenic plants and their fruit (see U.S. Pat. No. 6,031,154, herein incorporated by reference). A further example of transgenes that may be used are genes that alter grain yield. For example, U.S. Pat. No. 6,486,383, herein incorporated by reference, describes modification of starch content in plants with subunit proteins of adenosine diphosphoglucose pyrophosphorylase ("ADPG PPase"). In EP0797673, herein incorporated by reference, transgenic plants are discussed in which the introduction and expression of particular DNA molecules results in the formation of easily mobilized phosphate pools outside the vacuole and an enhanced biomass production and/or altered flowering behavior. Still further known are genes for altering plant maturity. U.S. Pat. No. 6,774,284, herein incorporated by reference, describes DNA encoding a plant lipase and methods of use thereof for controlling senescence in plants. U.S. Pat. No. 6,140,085, herein incorporated by reference, discusses FCA genes for altering flowering characteristics, particularly timing of flowering. U.S. Pat. No. 5,637,785, herein incorporated by reference, discusses genetically modified plants having modulated flower development such as having early floral meristem development and comprising a structural gene encoding the LEAFY protein in its genome.

In another aspect, the present invention provides methods and compositions for the preferred deployment of conventional and transgenic traits related to fatty acid synthesis and oil content. Using present invention, breeders can tailor trait integration to geographies for preferred trait expression, whether the trait is conventional (for example, a mutation) or transgenic. For example, a transgene may be employed that alters plant oil biosynthesis and oil composition. In particular, linoleic acid (LA) (18:2, $\Delta 9, 12$) is produced from oleic acid (18:1, $\Delta 9$) by a $\Delta 12$-desaturase (encoded by FAD2) while alpha linolenic acid (ALA) (18:3, $\Delta 9, 12, 15$) is produced from LA by a $\Delta 15$-desaturase (encoded by FAD3). Moreover, stearidonic acid (SDA) (18:4, $\Delta 6, 9, 12, 15$) and gamma linolenic acid (GLA) (18:3, $\Delta 6, 9, 12$) are polyunsaturated fatty acids (PUFAs) produced from LA and ALA by a $\Delta 6$-desaturase. Various genes encoding desaturases have been described. For example, U.S. Pat. No. 5,952,544, herein incorporated by reference, describes nucleic acid fragments isolated and cloned from *Brassica napus* that encode fatty acid desaturase enzymes. Expression of the *B. napus* $\Delta 15$-desaturase of the '544 patent resulted in accumulation of ALA. U.S. Pat. Publication 20060156435, herein incorporated by reference, describes the expression of fungal $\Delta 15$-desaturases to increase omega-3 fatty acid profiles in plants. PCT Publication WO05/021761, herein incorporated by reference, discusses genetically engineered plants which produce both SDA and GLA as a result of expressing a $\Delta 6$-desaturase and a $\Delta 15$-desaturase. Long chain PUFAs such as EPA and DHA can be produced in plants as disclosed in US Pat. Publication 20040172682, herein incorporated by reference.

Inhibition of the endogenous soy FAD2 gene through use of transgenes that inhibit the expression of FAD2 has been shown to confer a desirable mid-oleic acid (18:1) phenotype (i.e. soybean seed comprising about 50% and 75% oleic acid by weight). Transgenes and transgenic plants that provide for inhibition of the endogenous FAD2 gene expression and a mid-oleic phenotype are disclosed in U.S. Pat. No. 7,067,722, herein incorporated by reference. In contrast, wild type soybean plants that lack FAD2 inhibiting transgenes typically produce seed with oleic acid compositions of less than 20%. Inhibition of the endogenous FAD3 gene gene through use of transgenes that inhibit the expression of FAD3 has been shown to confer a desirable linolenic acid (18:3) phenotype. A "FATB" or "palmitoyl-ACP thioesterase" gene encodes an enzyme (FATB) capable of catalyzing the hydrolytic cleavage of the carbon-sulfur thioester bond in the panthothene prosthetic group of palmitoyl-ACP as its preferred reaction. Hydrolysis of other fatty acid-ACP thioesters may also be catalyzed by this enzyme. Representative FATB-1 sequences include, without limitation, those set forth in U.S Pat. Publication 20040006792 and U.S. Pat. Nos. 5,955,329; 5,723,761; 5,955,650; and 6,331,664, herein incorporated by reference. When the amount of FATB is decreased in a plant cell, a decreased amount of saturated fatty acids such as palmitate and stearate may be provided. Thus, a decrease in expression of FATB may result in an increased proportion of unsaturated fatty acids such as oleic acid (18:1). The simultaneous suppression of FAD2, FAD3, and FATB expression thereby results in driving the FAS pathway toward an overall increase in mono-unsaturated fatty acids of 18-carbon length, such as oleic acid (C18:1). See U.S. Pat. No. 5,955,650, herein incorporated by reference.

In an aspect, the present invention provides methods and compositions for the preferred deployment of conventional and transgenic traits related to fatty acid synthesis and oil content. Soybean seed oil levels are highly impacted by environment. Oil concentration increases with decreasing latitude, therefore, soybeans in maturity groups 00-I generally have lower oil levels than later maturing soybeans (Yaklich et al. 2002. *Crop Sci* 42:1504-1515). The decrease in oil concentrations is attributed to lower temperatures and shorter growing season (Piper and Boote 1999 J. Am. Oil Chem. Soc. 76:1233-124). In addition, soybeans cultivated under drought stress tend to produce seeds with decreased protein and increased oil (Specht et al. 2001 Crop Sci 41:493-509). Using present invention, breeders can tailor trait integration to geographies for preferred trait expression, whether the trait is conventional (for example, a mutation) or transgenic.

Genes for altering plant morphological characteristics are also known and may be used in accordance with the invention. U.S. Pat. No. 6,184,440, herein incorporated by reference, discusses genetically engineered plants which display altered structure or morphology as a result of expressing a cell wall modulation transgene. Examples of cell wall modulation transgenes include a cellulose binding domain, a cellulose binding protein, or a cell wall modifying protein or enzyme such as endoxyloglucan transferase, xyloglucan endo-transglycosylase, an expansin, cellulose synthase, or a novel isolated endo-1,4-β-glucanase.

Methods for introduction of a transgene, for instance to soybean, are well known in the art and include biological and physical plant transformation protocols. See, for example, Miki et al. (1990), Clemente et al. (Clemente et al., *Crop Sci.*, 40:797-803, 2000), and U.S. Pat. No. 7,002,058, all herein incorporated by reference. A further aspect of the invention relates to tissue cultures of a soybean variety of the invention. Exemplary types of tissue cultures are protoplasts, calli and plant cells that are intact in plants or parts of plants. Plant parts include, but not limited to, embryos, pollen, flowers, leaves, roots, root tips, anthers, vascular tissue, pod, stem, seed, or a portion thereof, or a cell isolated from the plant. In an aspect, the tissue culture comprises plant parts such as embryos, protoplasts, meristematic cells, pollen, leaves or anthers. In these ways, plants of the present invention or parts thereof be grown in culture and regenerated. Exemplary procedures for preparing tissue cultures of regenerable soybean cells and regenerating soybean plants therefrom, are disclosed in U.S. Pat. No. 4,992,375; U.S. Pat. No. 5,015,580; U.S. Pat. No. 5,024,944, and U.S. Pat. No. 5,416,011, each of the disclosures of which is specifically incorporated herein by reference in its entirety. An important ability of a tissue culture is the capability to regenerate fertile plants. For transformation to be efficient and successful, DNA must be introduced into cells that give rise to plants or germ-line tissue.

In particular, methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters,* 19: 193-201 (1980); Cheng et al., *Plant Science Letters,* 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985)). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986)).

Once a transgene is introduced into a variety it may readily be transferred by crossing. By using backcrossing, essentially all of the desired morphological and physiological characteristics of a variety are recovered in addition to the locus transferred into the variety via the backcrossing technique. Backcrossing methods can be used with the present invention to improve or introduce a characteristic into a plant (Poehlman and Sleper, In: *Breeding Field Crops*, Iowa State University Press, Ames, 1995; Fehr, *Principles of Cultivar Development* Vol. 1, pp. 2-3 (1987), herein incorporated by reference).

The present invention includes a method of soybean plant breeding by crossing at least two different parent soybean plants, where the parent soybean plants differ in plant maturity by over 10 days, 10 days-20 days, 10 days-30 days; obtaining a progeny seed from the cross; genotyping a progeny seed of the cross with a genetic marker; and selecting a soybean seed possessing a genotype for preferred maturity. The present invention also includes a method of soybean plant breeding by assaying a soybean plant for the presence of a marker sequences selected from SEQ ID NO: 143 through SEQ ID NO: 213; and associating the soybean plant with a maturity group. The present invention also includes a method of soybean plant breeding comprising crossing a parent soybean plant having a desired trait with a second parent soybean plant, where the parent soybean plants differ in soybean plant maturity by over 10 days, 10 days-20 days, 10 days-30 days, by crossing a parent soybean plant comprising a desired trait with a second parent soybean plant; obtaining progeny soybean seed from the cross; screening a progeny soybean seed for the trait; screening a progeny soybean seed for a desired maturity group using a marker selected from the group consisting of SEQ ID NO: 143 through SEQ ID NO: 213 to determine the desired geographical growing region; and selecting a progeny soybean seed containing the desired trait and desired soybean plant maturity.

In an aspect of the present invention, a method of soybean plant breeding includes crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group. In a preferred aspect, the maturity phenotype of the progeny soybean plant or soybean seed is unknown. In another preferred aspect, the progeny is grown under conditions that are unsuitable for determining maturity of the soybean plant. In another preferred aspect, the parent soybean plants differ in soybean plant maturity by over 5 days, over 10 days, 10 days-20 days, 10 days-30 days. herein a maturity phenotype of at least one of the two different parent soybean plants is unknown. In a preferred aspect, the maturity phenotype of both of the two different parent soybean plants is unknown. In a preferred aspect, the progeny soybean plant is not photoperiod sensitive. In another preferred aspect, at least one parent soybean plant is not photoperiod sensitive. In a preferred aspect, both parent soybean plants are not photoperiod sensitive. In a preferred aspect, the maturity genomic region is characterized by a dominant allele identified in Table 6. In a preferred aspect, the maturity genomic region is characterized by a recessive allele identified in Table 6.

In an aspect of the present invention, at least one or both parent soybean plant are an elite variety. In an aspect of the present invention, a progeny soybean plant is an exotic soybean plant or one or both parent soybean plants are exotic soybean plants.

An aspect of the present invention includes a method of selecting a soybean plant for germplasm improvement by determining a maturity group by crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group; and incorporating the selected soybean plant into a use selected from the group consisting of using the soybean plant for breeding, advancement of the soybean plant through self-fertilization, trait integration, use of soybean plant or parts thereof for transformation, and use of soybean plants or parts thereof for mutagenesis.

Another aspect of the present invention includes a method of co-selecting a soybean plant for expression of a non-maturity phenotypic trait and a maturity trait by crossing at least two different parent soybean plants; obtaining a progeny soybean plant from the cross; nondestructive genotyping a progeny soybean plant or soybean seed of the cross with a genetic marker characterizing a maturity genomic region; and selecting a soybean plant possessing a genotype for a desired maturity group; and to determine the desired geography for the progeny soybean plant growth, and a method for determining the non-maturity phenotype.

In a preferred aspect, the method for detecting the non-maturity phenotype is a genotypic or phenotypic method. In a preferred aspect, the non-maturity phenotypic trait is any of herbicide tolerance, increased yield, insect control, fungal disease resistance, virus resistance, nematode resistance, bacterial disease resistance, mycoplasma disease resistance, altered oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid soybean seed production, reduced allergenicity, biopolymers, and biofuels.

In another preferred aspect, a phenotypic trait is any of altered protein and oil composition, altered levels of a molecule selected from the group consisting of protein, oil, linolenic acid, stearic acid, palmitic acid, oleic acid, linoleic acid, stearidonic acid, alpha-linolenic acid, gamma linolenic acid, docosahexaenoic acid, eicosapentaenoic acid, docosapentaenoic acid, and combinations thereof.

In one aspect, plants of the present invention can be used in activities related to germplasm improvement, non-limiting examples of which include using the plant for breeding, advancement of the plant through self-fertilization, trait integration, use of plant or parts thereof for transformation, and use of plants or parts thereof for mutagenesis. Non-limiting examples of breeding decisions include progeny selection, parent selection, and recurrent selection for at least one haplotype. In another aspect, breeding decisions relating to development of plants for commercial release comprise advancing plants for testing, advancing plants for purity, purification of sublines during development, variety development, and hybrid development. In yet other aspects, breeding decisions and germplasm improvement activities comprise transgenic event selection, making breeding crosses, testing and advancing a plant through self-fertilization, using plants or parts thereof for transformation, using plants or parts thereof for candidates for expression constructs, and using plants or parts thereof for mutagenesis. The choice of breeding method depends on the mode of plant reproduction, the heritability of the trait(s) being improved, and the type of cultivar used commercially (e.g., $F_1$ hybrid cultivar, pureline cultivar, etc).

Descriptions of breeding methods that are commonly used for soybeans can be found in one of several reference books (e.g. Fehr, *Principles of Cultivar Development* Vol. 1, pp. 2-3 (1987)).

In one aspect the present invention includes a method of soybean plant breeding by assaying a soybean plant for the presence of a marker sequences selected from the group consisting of SEQ ID NO: 143 through SEQ ID NO: 213; and associating the soybean plant with a maturity group.

In another aspect the present invention includes a method of soybean plant breeding comprising crossing a parent soybean plant having a desired trait with a second parent soybean plant, wherein the parent soybean plants differ in soybean plant maturity by over 5 days, over 10 days, 10 days-20 days, or 10 days-30 days, by crossing a parent soybean plant comprising a desired trait with a second parent soybean plant; obtaining progeny soybean seed from the cross; screening a progeny soybean seed for the trait; screening a progeny soybean seed for a desired maturity group using a marker selected from the group consisting of SEQ ID NO: 143 through SEQ ID NO: 213 to determine the desired geographical growing region; and selecting a progeny soybean seed containing the desired trait and desired soybean plant maturity. In a preferred aspect, the desired trait is transgenic.

An aspect of the present invention includes a method of soybean plant breeding by crossing at least two different parent soybean plants, wherein the parent soybean plants differ in soybean plant maturity by over 5 days, over 10 days, 10 days-20 days, or days-30 days; obtaining a progeny soybean seed from the cross; genotyping a progeny soybean seed of the cross with a genetic marker; and selecting a soybean seed possessing a genotype for preferred maturity.

Another aspect of the present invention includes a method of screening soybean seeds based on soybean plant maturity group by obtaining DNA from a soybean seed; determining if an allele within maturity genomic region 1 is homozygous or heterozygous; determining if an allele within maturity genomic region 2 is homozygous or heterozygous; determining if an allele within maturity genomic region 3 is homozygous or heterozygous; and assigning a maturity growth value to the soybean seed.

One aspect of the present invention is a method of introgressing an allele into a soybean plant by crossing at least two different parent soybean plants; obtaining a progeny soybean plant from the cross; screening the progeny soybean plant of the cross for the allele; obtaining DNA from a soybean seed of the progeny soybean plant using a non-destructive method; and selecting a soybean seed, wherein the soybean seed comprises the allele and a nucleic acid sequence selected from the group consisting of SEQ ID NOs: 143-213. In a preferred aspect, the selected soybean seed further has a second sequence selected from the group consisting of SEQ ID NOs: 143-213. In another preferred aspect, the allele is selected from any or both of SCN resistance and root rot resistance.

Another aspect of the present invention includes a method of introducing a desired trait into a soybean plant by crossing at least two different parent soybean plants, wherein at least one parent soybean plant has a desired trait; obtaining a progeny soybean seed from the cross; obtaining DNA from a soybean seed of the progeny soybean plant using a non-destructive method; assaying the progeny soybean seed of the cross for evidence of the desired trait; and selecting the soybean seed with the desired trait and a desired maturity group. In a preferred aspect, the desired trait is transgenic.

A further aspect of the present invention includes a method of introgressing an allele into a soybean plant by crossing at least two different parent soybean plants; obtaining a progeny soybean plant from the cross; obtaining DNA from a soybean seed of the progeny soybean plant using a non-destructive method; and selecting a soybean seed with the allele and a nucleic acid sequence selected from the group consisting of SEQ ID NOs: 143-174.

Another aspect of the present invention includes a method of soybean plant breeding by crossing at least two different parent soybean plants, wherein the parent soybean plants differ in soybean plant maturity by over 10 days; obtaining progeny soybean seed from the cross; genotyping the progeny soybean seed of the cross with a genetic marker selected from the group consisting of SEQ ID NOs: 143-213; and selecting a soybean seed with a desired maturity group. A further aspect of the present invention includes a soybean plant comprising within its genome an introgressed haplotype associated with maturity, wherein the introgression is facilitated by at least one of the markers from SEQ ID NO: 143-213 or of the markers 143-162.

Having now generally described the invention, the same will be more readily understood through reference to the following examples which are provided by way of illustration, and are not intended to be limiting of the present invention, unless expressly specified.

EXAMPLES

Example 1

Discovery of Molecular Markers Associated with Genomic Regions Affecting Plant Maturity Soybean is a short day plant, therefore flowering is initiated by short days due to a decrease in photoperiod (Garner & Allard, *J. Agric. Res.* 18, 553-606 (1920)). Consequently, photoperiod (day length) and temperature response of the soybean plant determines areas of plant adaptation. Due to photoperiod sensitivity, soybean genotypes are grown to narrow zones of latitude to optimize yield. Northern soybean varieties, in contrast to Southern varieties, initiate flowering with longer days. Northern varieties planted south of their adaptation zone exhibit accelerated flowering, limited plant growth and reduced yield. Southern soybean varieties planted north of their adaptation zone will have delayed flowering with a potential for frost damage that may reduce yield. Most soybean variety development crosses are made between parents within 10 maturity days of each other. If the parents differ greatly in maturity, progeny plants segregate widely for maturity. In order for breeders to obtain and select for soybean plants of a desire maturity group, they must produce and maintain a large number of progeny plants, the practice of which is cost prohibitive. Identification of genomic regions associated with plant maturity facilitated crosses between parents outside 10 maturity days of each other without maintain a large number of progeny plants.

To identify genomic regions associated with plant maturity, 258 soybean lines (129 pairs of differing maturity groups) are genotyped with one thousand, four hundred single nucleotide polymorphism (SNP) markers, distributed across the 20 linkage groups of the soybean genetic linkage map. In addition, 258 soybean lines are phenotyped for yield and plant maturity. Associations between SNP marker genotype and plant maturity phenotype are then evaluated. This was done in multiple environments (Tables 2-3).

TABLE 1

Initial identification of maturity genomic regions via marker assisted breeding

| Region | Marker | SEQ ID NO: | Effect (Δ d) | P-value |
|---|---|---|---|---|
| 1 | NS0125408 | 148 | −0.05071 | 0.009068 |
| 1 | NS0098982 | 155 | 1.242281 | 0.01081 |
| 2 | NS0123506 | 156 | −0.57638 | 0.021863 |
| 3 | NS0093197 | 164 | 1.274868 | 1.92E−09 |
| 3 | NS0136544 | 171 | 1.162352 | 1.33E−10 |
| 3 | NS0119569 | 172 | −1.87063 | 3.79E−15 |
| 3 | NS0114317 | 174 | 1.419675 | 3.01E−08 |
| 5 | NS0123168 | 188 | −0.21704 | 0.025498 |
| 6 | NS0103755 | 190 | −0.02572 | 0.011701 |
| 7 | NS0095211 | 199 | −0.09176 | 2.99E−07 |
| 7 | NS0097307 | 200 | −0.09023 | 6.66E−07 |
| 7 | NS0102630 | 202 | −0.08407 | 2.26E−06 |
| 7 | NS0102915 | 203 | −0.08226 | 5.19E−06 |
| 8 | NS0100652 | 206 | 1.75824 | 3.92E−06 |
| 8 | NS0119574 | 207 | 0.446757 | 0.045212 |
| 8 | NS0101020 | 212 | 0.829784 | 0.000462 |

TABLE 2

Estimated effect in days of maturity genomic regions

| Region | Marker | SEQ ID NO: | Est. effect on plant maturity (Δ d) | Effect (Δd) | P-value |
|---|---|---|---|---|---|
| 1 | NS0124601 | 143 | 4.7 | 0.309636 | 0.156883 |
| 1 | NS0096829 | 145 | 4.8 | 0.444689 | 0.022932 |
| 1 | NS0099746 | 146 | 4.7 | 0.315142 | 0.191492 |
| 1 | NS0123747 | 147 | 4.9 | 0.714394 | 0.011568 |
| 1 | NS0125408 | 148 | 4.8 | 0.538569 | 0.015846 |
| 1 | NS0128378 | 149 | 4.9 | 0.757069 | 0.01699 |
| 1 | NS0093976 | 154 | 5.1 | 0.989792 | 0.061019 |
| 1 | NS0098982 | 155 | 5.2 | 1.242281 | 0.01081 |
| 2 | NS0123506 | 156 | 4.1 | 0.911763 | 0.007307 |
| 2 | NS0097952 | 157 | 5.6 | 4.069668 | 5.06E−30 |
| 2 | NS0118907 | 158 | 6.3 | 5.477999 | 1.01E−33 |
| 2 | NS0126989 | 160 | 4.6 | 1.994585 | 0.000191 |
| 2 | NS0095677 | 161 | 3.8 | 0.473053 | 0.10136 |
| 3 | NS0093197 | 164 | 5.2 | 1.274868 | 1.92E−09 |
| 3 | NS0103853 | 167 | 6 | 2.937938 | 3.78E−09 |
| 3 | NS0136544 | 171 | 6.4 | 3.765493 | 3.23E−11 |
| 3 | NS0119569 | 172 | 5.8 | 2.409513 | 1.72E−21 |
| 3 | NS0123708 | 173 | 6 | 2.876505 | 3.44E−26 |
| 3 | NS0114317 | 174 | 5.9 | 2.627908 | 1.69E−22 |
| 4 | NS0098176 | 176 | 4.3 | 1.068684 | 6.45E−12 |
| 4 | NS0100078 | 177 | 4 | 0.479955 | 0.073839 |
| 4 | NS0095530 | 179 | 4.5 | 1.364994 | 2.50E−09 |
| 4 | NS0129004 | 180 | 4.5 | 1.48424 | 8.04E−08 |
| 5 | NS0099024 | 181 | 3.4 | 0.732455 | 0.112193 |
| 5 | NS0101863 | 182 | 3.3 | 0.434912 | 0.078906 |
| 5 | NS0103446 | 183 | 3.1 | 0.181809 | 0.058299 |
| 5 | NS0123168 | 188 | 3.2 | 0.217041 | 0.025498 |
| 6 | NS0103755 | 190 | 1.2 | 0.609071 | 0.140857 |
| 6 | NS0116125 | 191 | 0.9 | 0.456086 | 0.152892 |
| 6 | NS0125713 | 192 | 1.1 | 0.566084 | 0.036335 |
| 6 | NS0125770 | 193 | 0.8 | 0.414212 | 0.009099 |
| 6 | NS0119281 | 194 | 1.6 | 0.797885 | 0.038077 |
| 6 | NS0124590 | 195 | 1.4 | 0.706375 | 0.000889 |
| 6 | NS0102717 | 196 | 1.5 | 0.749548 | 0.000246 |
| 7 | NS0099531 | 197 | 1.3 | 0.636575 | 0.000701 |
| 7 | NS0099417 | 198 | 2.4 | 1.181523 | 0.015954 |
| 7 | NS0095211 | 199 | 1.7 | 0.835736 | 0.099501 |
| 7 | NS0097307 | 200 | 0.2 | 0.090232 | 6.66E−07 |
| 7 | NS0102630 | 202 | 2.1 | 1.029761 | 0.046938 |
| 7 | NS0102915 | 203 | 2.5 | 1.231387 | 4.37E−09 |
| 8 | NS0102362 | 204 | 4.8 | 2.23831 | 1.23E−09 |

TABLE 2-continued

Estimated effect in days of maturity genomic regions

| Region | Marker | SEQ ID NO: | Est. effect on plant maturity (Δ d) | Effect (Δd) | P-value |
|---|---|---|---|---|---|
| 8 | NS0117716 | 205 | 4.3 | 1.171503 | 9.09E−06 |
| 8 | NS0100652 | 206 | 4.6 | 1.75824 | 3.92E−06 |
| 8 | NS0119574 | 207 | 4.3 | 1.195594 | 4.79E−05 |
| 8 | NS0127728 | 208 | 4.5 | 1.630904 | 3.33E−07 |
| 8 | NS0099639 | 209 | 4.2 | 1.037891 | 0.015656 |
| 8 | NS0103255 | 210 | 4.2 | 0.975115 | 0.001037 |
| 8 | NS0119106 | 211 | 4.3 | 1.18298 | 0.023909 |
| 8 | NS0101020 | 212 | 4.1 | 0.829784 | 0.000462 |
| 8 | NS0101779 | 213 | 4.2 | 1.000886 | 0.000563 |

The approximate locations of informative markers indicating a state of dominance or recessivity of genomic regions 1, 2, 3, 4, 5, 6, 7, and 8 are determined based upon a survey of polymorphisms among a panel of 258 soybean lines (Table 3 and 4). One factor in choosing these informative markers is based on which marker has the largest effect or is associated with the largest delay in maturity such that it is indicative of the maturity phenotype. Another factor in choosing these informative markers is based on the lowest P value, such that the marker does not get lost in the event of recombination. The markers with lower P value are more likely to be consistently associated with the maturity phenotype across different soybean populations (different parents, different pedigrees). Markers with strong association and predictive of introgression of the genomic region are listed in Table 5. For NS0128378, the SNP is actually an 11-bp indel, where "D" represents the deletion (***********) and "I" represents the insertion (TTCGAAGATTT (SEQ ID NO: 356)).

TABLE 3

Position of SNP markers associated with regions 1, 2, 3, 4, 5, 6, 7 and 8.

| Region | LG | Position (cM) | Marker | Polymorphism position on Consensus Sequence | SEQ ID NO: |
|---|---|---|---|---|---|
| 1 | C2 | 113.7 | NS0124601 | 884 | 143 |
| 1 | C2 | 121.9 | NS0103749 | 96 | 144 |
| 1 | C2 | 121.9 | NS0096829 | 225 | 145 |
| 1 | C2 | 121.9 | NS0099746 | 330 | 146 |
| 1 | C2 | 121.9 | NS0123747 | 56 | 147 |
| 1 | C2 | 121.9 | NS0125408 | 133 | 148 |
| 1 | C2 | 121.9 | NS0128378 | 212 | 149 |
| 1 | C2 | 129.3 | NS0135390 | 108 | 150 |
| 1 | C2 | 123 | NS0099529 | 243 | 151 |
| 1 | C2 | 124.3 | NS0097798 | 325 | 152 |
| 1 | C2 | 129.4 | NS0093385 | 109 | 153 |
| 1 | C2 | 134.7 | NS0093976 | 242 | 154 |
| 1 | C2 | 134.7 | NS0098982 | 383 | 155 |
| 2 | O | 125.4 | NS0123506 | 126 | 156 |
| 2 | O | 127.7 | NS0097952 | 420 | 157 |
| 2 | O | 134.9 | NS0118907 | 450 | 158 |
| 2 | O | 151.4 | NS0122182 | 104 | 159 |
| 2 | O | 150.8 | NS0126989 | 251 | 160 |
| 2 | O | 158.5 | NS0095677 | 202 | 161 |
| 3 | L | 99.4 | NS0098853 | 82 | 162 |
| 3 | L | 111.5 | NS0092561 | 190 | 163 |
| 3 | L | 99.4 | NS0093197 | 225 | 164 |
| 3 | L | 100.4 | NS0094891 | 83 | 165 |
| 3 | L | 99.4 | NS0096225 | 471 | 166 |
| 3 | L | 136.2 | NS0103853 | 341 | 167 |
| 3 | L | 114.2 | NS0113929 | 685 | 168 |
| 3 | L | 114.2 | NS0115535 | 433 | 169 |
| 3 | L | 113.6 | NS0121511 | 512 | 170 |
| 3 | L | 132.9 | NS0136544 | 208 | 171 |
| 3 | L | 143.1 | NS0119569 | 262 | 172 |
| 3 | L | 145.8 | NS0123708 | 530 | 173 |
| 3 | L | 155.9 | NS0114317 | 331 | 174 |
| 4 | I | 48.3 | NS0092743 | 217 | 175 |
| 4 | I | 49.6 | NS0098176 | 92 | 176 |
| 4 | I | 66.4 | NS0100078 | 1412 | 177 |
| 4 | I | 58.3 | NS0137415 | 231 | 178 |
| 4 | I | 33.4 | NS0095530 | 327 | 179 |
| 4 | I | 32.3 | NS0129004 | 1014 | 180 |
| 5 | L | 40.1 | NS0099024 | 69 | 181 |
| 5 | L | 35.7 | NS0101863 | 381 | 182 |
| 5 | L | 40.1 | NS0103446 | 69 | 183 |
| 5 | L | 35.9 | NS0113878 | 375 | 184 |
| 5 | L | 36.8 | NS0115066 | 298 | 185 |
| 5 | L | 36.9 | NS0119165 | 181 | 186 |
| 5 | L | 36.8 | NS0120015 | 449 | 187 |
| 5 | L | 36 | NS0123168 | 75 | 188 |
| 5 | L | 38.8 | NS0123724 | 42 | 189 |
| 6 | D1b + W | 172.5 | NS0103755 | 45 | 190 |
| 6 | D1b + W | 164.1 | NS0116125 | 409 | 191 |
| 6 | D1b + W | 176.3 | NS0125713 | 392 | 192 |
| 6 | D1b + W | 165.4 | NS0125770 | 1074 | 193 |
| 6 | D1b + W | 134.8 | NS0119281 | 596 | 194 |
| 6 | D1b + W | 157.6 | NS0124590 | 1092 | 195 |
| 6 | D1b + W | 177.2 | NS0102717 | 402 | 196 |
| 7 | G | 111.5 | NS0099531 | 287 | 197 |
| 7 | G | 122.1 | NS0099417 | 408 | 198 |
| 7 | G | 125.7 | NS0095211 | 251 | 199 |
| 7 | G | 125.7 | NS0097307 | 426 | 200 |
| 7 | G | 130.4 | NS0103004 | 430 | 201 |
| 7 | G | 132.1 | NS0102630 | 186 | 202 |
| 7 | G | 131.2 | NS0102915 | 193 | 203 |
| 8 | M | 37.7 | NS0102362 | 74 | 204 |
| 8 | M | 42.2 | NS0117716 | 74 | 205 |
| 8 | M | 44.2 | NS0100652 | 247 | 206 |
| 8 | M | 44.2 | NS0119574 | 367 | 207 |
| 8 | M | 42.8 | NS0127728 | 650 | 208 |
| 8 | M | 48.8 | NS0099639 | 362 | 209 |
| 8 | M | 64.8 | NS0103255 | 289 | 210 |
| 8 | M | 64.8 | NS0119106 | 417 | 211 |
| 8 | M | 67.1 | NS0101020 | 238 | 212 |
| 8 | M | 67.1 | NS0101779 | 147 | 213 |

Allele-specific fluorescence-resonance-energy-transfer (FRET) probes are used in Real-Time PCR assays. Two FRET probes bearing different fluorescent reporter dyes are used, where a unique dye is incorporated into an oligonucleotide that can anneal with high specificity to only one of the two alleles. The reporter dyes are 2'-chloro-7'-phenyl-1,4-dichloro-6-carboxyfluorescein (VIC) and 6-carboxyfluorescein phosphoramidite (FAM).

TABLE 4

Listing of SNP markers associated with regions 1, 2, 3, 4, 5, 6, 7 and 8.

| Region | Marker | SEQ ID NO: | SEQ ID NO: Forward Primer | SEQ ID NO: Reverse Primer | SEQ ID NO: FAM Probe | FAM Allele | SEQ ID NO: VIC probe | VIC allele |
|---|---|---|---|---|---|---|---|---|
| 1 | NS0124601 | 143 | 1 | 2 | 214 | T | 215 | G |
| 1 | NS0103749 | 144 | 3 | 4 | 216 | G | 217 | A |
| 1 | NS0096829 | 145 | 5 | 6 | 218 | C | 219 | A |
| 1 | NS0099746 | 146 | 7 | 8 | 220 | G | 221 | A |
| 1 | NS0123747 | 147 | 9 | 10 | 222 | T | 223 | A |
| 1 | NS0125408 | 148 | 11 | 12 | 224 | T | 225 | C |
| 1 | NS0128378 | 149 | 13 | 14 | 226 | TTCGAAGATTT | 227 | ********** |
| 1 | NS0135390 | 150 | 15 | 16 | 228 | T | 229 | G |
| 1 | NS0099529 | 151 | 17 | 18 | 230 | T | 231 | A |
| 1 | NS0097798 | 152 | 19 | 20 | 232 | G | 233 | A |
| 1 | NS0093385 | 153 | 21 | 22 | 234 | T | 235 | C |
| 1 | NS0093976 | 154 | 23 | 24 | 236 | G | 237 | C |
| 1 | NS0098982 | 155 | 25 | 26 | 238 | C | 239 | * |
| 2 | NS0123506 | 156 | 27 | 28 | 240 | T | 241 | G |
| 2 | NS0097952 | 157 | 29 | 30 | 242 | G | 243 | A |
| 2 | NS0118907 | 158 | 31 | 32 | 244 | C | 245 | A |
| 2 | NS0122182 | 159 | 33 | 34 | 246 | T | 247 | C |
| 2 | NS0126989 | 160 | 35 | 36 | 248 | T | 249 | A |
| 2 | NS0095677 | 161 | 37 | 38 | 250 | T | 251 | C |
| 3 | NS0098853 | 162 | 39 | 40 | 252 | AG | 253 | ** |
| 3 | NS0092561 | 163 | 41 | 42 | 254 | T | 255 | C |
| 3 | NS0093197 | 164 | 43 | 44 | 256 | G | 257 | A |
| 3 | NS0094891 | 165 | 45 | 46 | 258 | T | 259 | G |
| 3 | NS0096225 | 166 | 47 | 48 | 260 | C | 261 | A |
| 3 | NS0103853 | 167 | 49 | 50 | 262 | T | 263 | C |
| 3 | NS0113929 | 168 | 51 | 52 | 264 | G | 265 | C |
| 3 | NS0115535 | 169 | 53 | 54 | 266 | T | 267 | G |
| 3 | NS0121511 | 170 | 55 | 56 | 268 | T | 269 | C |
| 3 | NS0136544 | 171 | 57 | 58 | 270 | T | 271 | C |
| 3 | NS0119569 | 172 | 59 | 60 | 272 | T | 273 | A |
| 3 | NS0123708 | 173 | 61 | 62 | 274 | G | 275 | A |
| 3 | NS0114317 | 174 | 63 | 64 | 276 | G | 277 | A |
| 4 | NS0092743 | 175 | 65 | 66 | 278 | AGAA | 279 | **** |
| 4 | NS0098176 | 176 | 67 | 68 | 280 | T | 281 | C |
| 4 | NS0100078 | 177 | 69 | 70 | 282 | T | 283 | G |
| 4 | NS0137415 | 178 | 71 | 72 | 284 | T | 285 | C |

TABLE 4-continued

Listing of SNP markers associated with regions 1, 2, 3, 4, 5, 6, 7 and 8.

| Region | Marker | SEQ ID NO: | SEQ ID NO: Forward Primer | SEQ ID NO: Reverse Primer | SEQ ID NO: FAM Probe | FAM Allele | SEQ ID NO: VIC probe | VIC allele |
|---|---|---|---|---|---|---|---|---|
| 4 | NS0095530 | 179 | 73 | 74 | 286 | T | 287 | A |
| 4 | NS0129004 | 180 | 75 | 76 | 288 | G | 289 | A |
| 5 | NS0099024 | 181 | 77 | 78 | 290 | G | 291 | A |
| 5 | NS0101863 | 182 | 79 | 80 | 292 | G | 293 | A |
| 5 | NS0103446 | 183 | 81 | 82 | 294 | G | 295 | A |
| 5 | NS0113878 | 184 | 83 | 84 | 296 | G | 297 | A |
| 5 | NS0115066 | 185 | 85 | 86 | 298 | T | 299 | A |
| 5 | NS0119165 | 186 | 87 | 88 | 300 | G | 301 | A |
| 5 | NS0120015 | 187 | 89 | 90 | 302 | G | 303 | C |
| 5 | NS0123168 | 188 | 91 | 92 | 304 | T | 305 | C |
| 5 | NS0123724 | 189 | 93 | 94 | 306 | G | 307 | A |
| 6 | NS0103755 | 190 | 95 | 96 | 308 | T | 309 | A |
| 6 | NS0116125 | 191 | 97 | 98 | 310 | T | 311 | C |
| 6 | NS0125713 | 192 | 99 | 100 | 312 | G | 313 | A |
| 6 | NS0125770 | 193 | 101 | 102 | 314 | G | 315 | A |
| 6 | NS0119281 | 194 | 103 | 104 | 316 | G | 317 | A |
| 6 | NS0124590 | 195 | 105 | 106 | 318 | T | 319 | C |
| 6 | NS0102717 | 196 | 107 | 108 | 320 | G | 321 | A |
| 7 | NS0099531 | 197 | 109 | 110 | 322 | AA | 323 | ** |
| 7 | NS0099417 | 198 | 111 | 112 | 324 | G | 325 | C |
| 7 | NS0095211 | 199 | 113 | 114 | 326 | T | 327 | C |
| 7 | NS0097307 | 200 | 115 | 116 | 328 | G | 329 | C |
| 7 | NS0103004 | 201 | 117 | 118 | 330 | G | 331 | A |
| 7 | NS0102630 | 202 | 119 | 120 | 332 | C | 333 | A |
| 7 | NS0102915 | 203 | 121 | 122 | 334 | C | 335 | A |
| 8 | NS0102362 | 204 | 123 | 124 | 336 | T | 337 | C |
| 8 | NS0117716 | 205 | 125 | 126 | 338 | ACTT | 339 | **** |
| 8 | NS0100652 | 206 | 127 | 128 | 340 | T | 341 | A |
| 8 | NS0119574 | 207 | 129 | 130 | 342 | G | 343 | A |
| 8 | NS0127728 | 208 | 131 | 132 | 344 | G | 345 | A |
| 8 | NS0099639 | 209 | 133 | 134 | 346 | T | 347 | C |
| 8 | NS0103255 | 210 | 135 | 136 | 348 | T | 349 | C |
| 8 | NS0119106 | 211 | 137 | 138 | 350 | C | 351 | A |
| 8 | NS0101020 | 212 | 139 | 140 | 352 | C | 353 | C |
| 8 | NS0101779 | 213 | 141 | 142 | 354 | G | 355 | C |

TABLE 5

Most predictive markers for genomic regions associated with plant maturity and/or growth habit of soybean plants

| Region | Marker | SEQ ID NO: | Rec. Allele | Dom. Allele |
|---|---|---|---|---|
| 1 | NS0099529 | 151 | A | T |
| 1 | NS0128378 | 149 | *********** | TTCGAAGATTT |
| 2 | NS0118907 | 158 | A | C |
| 3 | NS0115535 | 169 | T | G |
| 4 | NS0137415 | 178 | C | T |
| 5 | NS0120015 | 187 | C | G |
| 6 | NS0125713 | 192 | A | G |
| 7 | NS0102630 | 202 | C | A |
| 8 | NS0102362 | 204 | C | T |

SNP markers associated with region 1 include SEQ ID NO: 143 through SEQ ID NO: 155. All of these SNP makers for region 1 map to a region on linkage group C2. Table 4 lists sequences for PCR amplification primers, indicated as SEQ ID NO: 1 through SEQ ID NO: 26, and probes indicated as SEQ ID NO: 214 through SEQ ID NO: 239. In Table 4, the sequence for the FAM. Allele in region 1, marker NS0128378, is SEQ ID NO:356. In Table 5, the Dom. Allele on row 3, marker NS0128378, is SEQ ID NO: 356.

SNP markers associated with region 2 include SEQ ID NO: 156 through SEQ ID NO: 161. All of these SNP makers for region 2 map to a region on linkage group O. Table 4 lists sequences for PCR amplification primers, indicated as SEQ ID NO: 27 through SEQ ID NO: 38, and probes indicated as SEQ ID NO: 240 through SEQ ID NO: 251.

SNP markers associated with region 3 include SEQ ID NO: 162 through SEQ ID NO: 174. All of these SNP makers for region 3 map to a region on linkage group L. Table 4 lists sequences for PCR amplification primers, indicated as SEQ ID NO: 39 through SEQ ID NO: 64, and probes indicated as SEQ ID NO: 252 through SEQ ID NO: 277.

SNP markers associated with region 4 include SEQ ID NO: 175 through SEQ ID NO: 180. All of these SNP makers for region 4 map to a region on linkage group I. Table 4 lists sequences for PCR amplification primers, indicated as SEQ ID NO: 65 through SEQ ID NO: 76 and probes indicated as SEQ ID NO: 278 through SEQ ID NO: 289.

SNP markers associated with region 5 include SEQ ID NO: 181 through SEQ ID NO: 189. All of these SNP makers for region 5 map to a region on linkage group L. Table 4 lists sequences for PCR amplification primers, indicated as SEQ ID NO: 77 through SEQ ID NO: 94, and probes indicated as SEQ ID NO: 290 through SEQ ID NO: 307.

SNP markers associated with region 6 include SEQ ID NO: 190 through SEQ ID NO: 196 of these SNP makers for region 6 map to a region on linkage group D1b. Table 4 lists sequences for PCR amplification primers, indicated as SEQ ID NO: 95 through SEQ ID NO: 108, and probes indicated as SEQ ID NO: 308 through SEQ ID NO: 321.

SNP markers associated with region 7 include SEQ ID NO: 197 through SEQ ID NO: 203. Table 4 lists sequences for PCR amplification primers, indicated as SEQ ID NO: 109 through SEQ ID NO: 122, and probes indicated as SEQ ID NO: 322 through SEQ ID NO: 333.

SNP markers associated with region 8 include SEQ ID NO: 204 through SEQ ID NO: 213 of these SNP makers map. Table 4 lists sequences for PCR amplification primers, indicated as SEQ ID NO: 123 through SEQ ID NO: 142 and probes indicated as SEQ ID NO: 336 through SEQ ID NO: 355.

Example 2

Identifying Allelic Combinations of Genomic Regions Associated with Plant Maturity in Early Maturity Group Soybeans Genomic regions 1 and 2 are used to predict the plant maturity of progeny plant resulting from a cross between early maturity and mid-maturity parents (III-V). In particular, the allelic combinations of genomic regions 1 and 2 are correlated with a delay in plant maturity. To determine the correlation between allelic combinations of region 1 and 2 and delay in plant maturity, three populations are developed from crossing an early maturity parent (maturity group 00) with a mid-maturity parent (maturity group III or IV) (Table 6). Populations 1-3 are used to determine the association of the composition of genomic regions 1 and 2 with delay in plant maturity.

TABLE 6

Maturity group phenotype of parents in soybean populations

| Population | Maturity Group of Female Parent | Maturity Group of Female Parent |
|---|---|---|
| 1 | 00.9 | 3.1 |
| 2 | 00.9 | 3.4 |
| 3 | 00.9 | 4.1 |
| 4 | 5.9 | 4.7 |
| 5 | 5.9 | 5.1 |
| 6 | 5.8 | 4.7 |
| 7 | 4.1 | 00.9 |
| 8 | 3.1 | 00.9 |
| 9 | 3.4 | 00.9 |

The three populations segregate widely for maturity and are polymorphic at genomic regions 1 and 2. $F_3$ seed are obtained by selecting one pod per $F_2$ plant (modified single seed descent). The $F_3$ populations are planted in Guelph, ON and 1,214 $F_3$ individuals from all three populations are phenotyped for genomic regions 1 and 2 with the SNP markers NS0128378 (genomic region 1) and NS0118907 (genomic region 2). Individual plants in the $F_3$ populations are also genotyped for maturity by counting the number of days after August $31^{st}$ until plant matures; plants are considered mature when 95% of the pods were brown. The procedure is repeated with 1055 of the individual plants where each plant row is grown in Chile and phenotyped for maturity by counting the number of days after March $1^{st}$ until plant matures; plants are considered mature when 95% of the pods are brown. The procedure is repeated with experimental breeding lines developed from 88 of the 1055 individual plants. Table 8 compares the days to maturity of individual plants across all three populations and the genotype of the individuals at genomic regions 1 and 2. The markers associated with 1 and 2 explain 64% of the variation in plant maturity in year 1 and 94% of the variation in plant maturity in year 2.

TABLE 7

The association of days to maturity with composition of regions 1 and 2. Presence (1) or absence (0) of dominant allele indicated. Homozygous allele states are 0, 0 and 1, 1. Heterozygous allele state is 0, 1.

| Allelic Combination | Region 1 | Region 2 | Days to Maturity (D after August $31^{st}$) Year 1 | Year 2 |
|---|---|---|---|---|
| 1 | 0, 0 | 0, 0 | 19.2 | 9.5 |
| 2 | 0, 0 | 0, 1 | 25.7 | 13.5 |
| 3 | 0, 0 | 1, 1 | 33.6 | 15.5 |
| 4 | 0, 1 | 0, 0 | 26.2 | 16.4 |
| 5 | 0, 1 | 0, 1 | 40.3 | ND |
| 6 | 0, 1 | 1, 1 | 49.1 | 19.5 |
| 7 | 1, 1 | 0, 0 | 34.2 | 17.11 |
| 8 | 1, 1 | 0, 1 | 49.3 | 22.7 |
| 9 | 1, 1 | 1, 1 | 53.5 | 23.9 |
| | | Correlation: | 64% | 94% |

Example 3

Identifying Allelic Combinations of Genomic Regions Associated with Plant Maturity in Late Maturity Group Soybeans Genomic regions 1, 2, and 3 are used to predict the plant maturity of progeny plant resulting from a cross between late maturity and mid-maturity parents. In particular, some of the allelic combinations of genomic regions 1, 2 and 3 are correlated with a delay in plant maturity (Table 8 and 9). To determine the correlation between allelic combinations of region 1, 2 and 3 and delay in plant maturity, three $F_3$ populations are developed from crossing a late maturity group V with a late maturity group IV. The populations 4-6 following crosses are used to determine the association of the composition of genomic regions 1, 2 and 3 with delay in plant maturity.

The three segregate widely for maturity and are polymorphic at genomic regions 1, 2, and 3. $F_3$ seed are obtained by selecting one seed per $F_2$ plant (single seed descent). 5,984 $F_3$ individuals from all three population are genotyped with the SNP markers NS0099529 (genomic region 1), NS0118907 (genomic region 2), and NS0115535 (genomic region 3) and seeds with the same marker haplotype are bulked. $F_3$ seeds are planted.

TABLE 8

Summary of days to flowering for soybean lines containing various compositions of genomic regions 1, 2, and 3 for plant maturity. Presence (1) or absence (0) of dominant allele indicated. Homozygous allele states are 0, 0 and 1, 1. Heterozygous allele state is 0, 1. ND = no data.

| Allelic Combination | Region 1 | Region 2 | Region 3 | Days to flowering (DAP) Pop. 4 | Pop. 5 | Pop. 6 |
|---|---|---|---|---|---|---|
| 10 | 1, 1 | 0, 0 | 1, 1 | 57 | 57 | 57 |
| 11 | 1, 1 | 1, 0 | 1, 1 | 58 | 57 | 58 |
| 12 | 1, 1 | 1, 1 | 0, 0 | 58 | 59 | 55 |
| 14 | 1, 1 | 0, 0 | 0, 0 | ND | ND | 54 |
| 15 | 0, 1 | 0, 1 | 0, 1 | 59 | 57 | 56 |
| 16 | 0, 0 | 1, 1 | 1, 1 | 43 | 36 | 41 |
| 17 | 0, 0 | 0, 0 | 1, 1 | 44 | 38 | 45 |
| 18 | 0, 0 | 1, 1 | 0, 0 | 44 | 39 | 44 |
| 19 | 0, 0 | 0, 0 | 0, 0 | 44 | 38 | 43 |

The individuals are also phenotyped for maturity by counting the number of days after August $31^{st}$ until plant matures; plants are considered mature when 95% of the pods were brown. Genomic region 3 influences the time of maturity (Tables 8 and 9).

TABLE 9

Summary of days to plant maturity for soybean lines containing various compositions of genomic regions 1, 2, and 3 for plant maturity.

| Allelic Combination | Days to Maturity (D after Aug) Pop. 4 | Pop 5 | Pop 6 |
|---|---|---|---|
| 10 | 59 | 58 | 58 |
| 11 | 54 | 58 | 58 |
| 12 | 59 | 57 | 59 |
| 14 | ND | ND | 58 |
| 15 | 54 | 54 | 53 |
| 16 | 41 | 35 | 37 |
| 17 | 37 | 35 | 38 |
| 18 | 44 | 44 | 43 |
| 19 | 38 | 42 | 43 |

ND = no data.

Example 4

Discovery of Molecular Markers Associated with Genomic Regions Affecting Plant Growth Habit Plant growth habit is an important characteristic for late maturity group growing regions. To identify genomic regions associated with plant growth habit, three $F_3$ populations are developed from crossing a late maturity group V (determinate growth habit) with a late maturity group IV (indeterminate growth habit). Populations 4-6 are used to determine the association of the genomic region 3 with plant habit (Table 6). Seven hundred and seventy-four soybean lines are screened with the markers associated with genomic region 3. The three populations segregated widely for maturity and are polymorphic at genomic region 3. $F_3$ seed are obtained by selecting one seed per $F_2$ plant (single seed descent). 5,984 $F_3$ individuals from all three population were phenotyped with the SNP NS0115535 (genomic region 3) and seeds with the same marker haplotype are bulked. $F_3$ seeds are planted. A single marker, NS0115535, is determined to be most predictive and able to separate determinant group V varieties from indeterminant group IV and earlier varieties.

Example 5

Genomic Regions Associated with Growth Habit and Maturity Independent of Yield Plant maturity and yield are closely associated in soybean. An increase of one day in maturity may be equivalent to a ~0.7 bu/A increase in yield. The correlation of plant maturity and yield confounds the evaluation of potential QTLs and candidate genes associated with yield. Identification of genomic regions associated with plant maturity allows breeders to genetically fix plant maturity within a soybean plant and elucidate traits associated with yield.

Three soybean populations are generated from crossing a maturity group 0 with a maturity group III or IV. Populations 7-9 are used (Table 5). The progeny seed planted in Chile and then harvested seeds from those progeny plants are selected in Chile and the plants are grown in Ontario in 2006. Eighty-four progeny are screened with markers associated maturity regions 1 and 2 and evaluated for maturity days and yield (Table 10-12). Markers associated with regions 1 and 2 select for maturity and are independent of yield. For example, Progeny 0430 has significantly higher yield than Progeny 0083 (Table 11). The higher yield of Progeny 0430 is not attributed to differences in plant maturity due similar days to maturity and allelic states of maturity genomic regions 1 and 2.

TABLE 10

Summary of yield, maturity and the allelic combination for maturity regions 1 and 2.

| Pedigree | Progeny ID No. | Best Est. Yield (Bu/A) | Maturity Days | Allelic combination |
|---|---|---|---|---|
| Population 8 | 0117 | 30.93 | 5.50 | 1 |
| Population 8 | 0140 | 29.18 | 6.50 | 1 |
| Population 8 | 0234 | 32.84 | 6.50 | 1 |
| Population 8 | 0043 | 34.67 | 6.50 | 1 |
| Population 8 | 0267 | 36.80 | 7.00 | 1 |
| Population 8 | 0276 | 40.67 | 7.50 | 1 |
| Population 8 | 0243 | 42.88 | 9.50 | 1 |
| Population 8 | 0198 | 39.56 | 10.50 | 1 |
| Population 8 | 0325 | 33.42 | 11.00 | 1 |
| Population 8 | 0011 | 39.92 | 11.50 | 1 |
| Population 8 | 0390 | 41.22 | 11.50 | 1 |
| Population 8 | 0418 | 44.05 | 11.50 | 1 |
| Population 8 | 0119 | 41.62 | 9.50 | 2 |
| Population 8 | 0069 | 37.68 | 10.00 | 2 |
| Population 8 | 0274 | 38.90 | 10.00 | 2 |
| Population 8 | 0165 | 43.03 | 10.00 | 2 |
| Population 8 | 0219 | 39.67 | 12.50 | 2 |
| Population 8 | 0373 | 49.22 | 13.00 | 2 |
| Population 8 | 0089 | 50.41 | 17.00 | 2 |
| Population 8 | 0186 | 43.74 | 18.00 | 2 |
| Population 8 | 0395 | 43.20 | 9.50 | 3 |
| Population 8 | 0426 | 41.12 | 10.00 | 3 |
| Population 8 | 0256 | 43.83 | 10.00 | 3 |
| Population 8 | 0216 | 45.47 | 10.50 | 3 |
| Population 8 | 0367 | 47.94 | 11.50 | 3 |
| Population 8 | 0266 | 42.86 | 14.00 | 3 |
| Population 8 | 0285 | 42.04 | 16.00 | 3 |
| Population 8 | 0277 | 50.47 | 16.00 | 3 |
| Population 8 | 0188 | 45.62 | 17.50 | 3 |
| Population 8 | 0143 | 44.47 | 13.50 | 4 |
| Population 8 | 0101 | 41.22 | 14.50 | 4 |
| Population 8 | 0366 | 41.79 | 16.50 | 4 |
| Population 8 | 0340 | 47.41 | 11.50 | 7 |
| Population 8 | 0359 | 46.10 | 14.50 | 7 |
| Population 8 | 0184 | 46.24 | 14.50 | 7 |
| Population 8 | 0158 | 43.08 | 16.00 | 7 |
| Population 8 | 0401 | 50.95 | 16.00 | 7 |
| Population 8 | 0255 | 47.26 | 17.00 | 7 |
| Overall Mean | | 42.78 | 12.00 | |
| Non-Check Mean | | 42.60 | 12.38 | |
| Check Mean | | 44.08 | 9.25 | |
| # Locs | | 3 | 2 | |
| # Reps | | 3 | 2 | |
| CV | | 9.978 | 15.094 | |
| LSD(.05) | | 6.989 | 3.640 | |
| F-Statistic | | 4.525 | 7.670 | |
| P-Value | | 0.000 | 0.000 | |
| Repeatability | | 0.781 | 0.870 | |
| Root MSE | | 4.269 | 1.811 | |

TABLE 11

Summary of yield, maturity and the allelic combination for maturity regions 1 and 2.

| Pedigree | Progeny ID No. | Best Est. Yield (Bu/A) | Maturity (D) | Allelic Combination |
|---|---|---|---|---|
| Population 9 | 0381 | 38.46 | 11.00 | 1 |
| Population 9 | 0473 | 40.89 | 12.50 | 1 |
| Population 9 | 0371 | 36.86 | 9.00 | 2 |
| Population 9 | 0380 | 31.86 | 10.00 | 2 |
| Population 9 | 0263 | 43.01 | 11.00 | 2 |
| Population 9 | 0396 | 38.97 | 12.00 | 2 |
| Population 8 | 0083 | 29.01 | 15.00 | 2 |
| Population 8 | 0430 | 42.65 | 15.00 | 2 |
| Population 9 | 0299 | 39.96 | 16.00 | 2 |
| Population 8 | 0076 | 42.95 | 22.00 | 2 |
| Population 9 | 0142 | 32.31 | 11.50 | 3 |
| Population 9 | 0487 | 27.86 | 14.00 | 3 |
| Population 8 | 0240 | 43.66 | 15.50 | 3 |
| Population 9 | 0317 | 46.74 | 16.50 | 3 |
| Population 8 | 0392 | 38.21 | 18.50 | 3 |
| Population 9 | 0206 | 45.77 | 19.00 | 3 |
| Population 9 | 0254 | 44.06 | 19.50 | 3 |
| Population 8 | 0280 | 48.22 | 26.50 | 3 |
| Population 9 | 0262 | 41.41 | 17.50 | 4 |
| Population 9 | 0173 | 43.17 | 23.50 | 4 |
| Population 9 | 0032 | 33.65 | 13.50 | 6 |
| Population 9 | 0166 | 40.72 | 11.50 | 7 |
| Population 9 | 0188 | 42.19 | 16.50 | 7 |
| Population 9 | 0117 | 47.98 | 19.00 | 7 |
| Population 8 | 0229 | 45.34 | 20.00 | 7 |
| Population 9 | 0437 | 43.25 | 20.50 | 7 |
| Population 9 | 0077 | 34.05 | 10.50 | 8 |
| Population 9 | 0078 | 47.66 | 17.00 | 8 |
| Population 9 | 0187 | 37.18 | 27.00 | 8 |
| Population 8 | 0230 | 47.26 | 20.50 | 9 |
| Population 9 | 0368 | 46.49 | 21.50 | 9 |
| Population 9 | 0505 | 34.06 | 23.50 | 9 |
| Overall Mean | | 39.96 | 15.69 | |
| Non-Check Mean | | 40.38 | 16.57 | |
| Check Mean | | 37.07 | 9.50 | |
| # Locs | | 3 | 2 | |
| # Reps | | 3 | 2 | |
| CV | | 15.453 | 13.984 | |
| LSD(.05) | | 10.105 | 4.434 | |
| F-Statistic | | 2.546 | 10.862 | |
| P-Value | | 0.000 | 0.000 | |
| Repeatability | | 0.609 | 0.908 | |
| Root MSE | | 6.176 | 2.194 | |

TABLE 12

Summary of yield, maturity and the allelic combination for maturity regions 1 and 2.

| Pedigree | Progeny ID No. | Best Est. Yield (Bu/A) | Maturity (D) | Allelic Combination |
|---|---|---|---|---|
| Population 7 | 0121 | 35.25 | 8.50 | 1 |
| Population 7 | 0107 | 30.98 | 10.50 | 1 |
| Population 7 | 0251 | 36.59 | 10.50 | 1 |
| Population 7 | 0377 | 34.51 | 11.00 | 1 |
| Population 7 | 0375 | 34.34 | 11.50 | 1 |
| Population 7 | 0326 | 30.51 | 13.00 | 1 |
| Population 7 | 0216 | 42.26 | 10.50 | 2 |
| Population 7 | 0312 | 36.15 | 18.00 | 2 |
| Population 7 | 0298 | 41.40 | 19.00 | 2 |
| Population 7 | 0205 | 39.41 | 13.00 | 3 |
| Population 7 | 0139 | 38.59 | 14.50 | 3 |
| Population 7 | 0365 | 38.14 | 13.00 | 4 |
| Population 7 | 0004 | 39.79 | 12.50 | 5 |
| Population 7 | 0361 | 47.75 | 24.00 | 8 |
| Overall Mean | | 39.37 | 12.55 | |
| Non-Check Mean | | 37.79 | 13.57 | |
| Check Mean | | 44.10 | 9.50 | |
| # Locs | | 3 | 2 | |
| # Reps | | 3 | 2 | |
| CV | | 16.518 | 11.343 | |
| LSD(.05) | | 10.749 | 2.979 | |

TABLE 12-continued

Summary of yield, maturity and the allelic combination for maturity regions 1 and 2.

| Pedigree | Progeny ID No. | Best Est. Yield (Bu/A) | Maturity (D) | Allelic Combination |
|---|---|---|---|---|
| F-Statistic | | 3.074 | 16.491 | |
| P-Value | | 0.002 | 0.000 | |
| Repeatability | | 0.675 | 0.939 | |
| Root MSE | | 6.503 | 1.423 | |

Example 6

Utilization of Molecular Markers Associated with Plant Maturity to Select Geographic Region for Planting Seed Soybean genotypes are grown to narrow zones of latitude to optimize yield due to photoperiod sensitivity. Northern soybean varieties, in contrast to Southern varieties, initiate flowering with longer days. Northern varieties planted south of their adaptation zone exhibit accelerated flowering, limited plant growth and reduced yield. Southern soybean varieties planted north of their adaptation zone have delayed flowering with a potential for frost damage that may reduce yield. When the parents differ in plant maturity greater than 10 day, the progeny of the cross segregate widely for plant maturity. Molecular markers associated with plant maturity genomic regions allows breeders to cross with parents that differ in maturity greater than 10 days, select seed of the cross to grow in the appropriate maturity zone.

A $BC_2F_1$ soybean population is generated by crossing MG III.5 with MG 000 and the seed is selected for the appropriate maturity zone growing region using the molecular markers associated with plant maturity. Ninety-three $BC_2F_1$ plants are screened with 106 SNP markers to evaluate the genetic similarity to the recurrent MG III.5 parent (Table 13). Additionally, the SNP markers included markers associated with the maturity genomic regions 1, 2, 3, 4, and 5. Each individual is heterozygous for at least one maturity genomic region. Individual Progeny: 0107 is heterozygous for 1, 2, 3, 4, and 5 and may be used to select for individual varieties adapted to each maturity group zone. Individuals selected to move forward to the next generation based on adaptation to specific maturity group regions using the allelic combination for the genomic maturity regions.

TABLE 13

Summary of heterozygousity for maturity genomic regions with the F2 generation of MG III.5 parent/(MG III.5 parent * 2/MG 000 parent). Individuals within the population are selected for a geographic maturity group region with SNP markers associated maturity genomic regions.

| Plant | Similarity to MGIII.5 parent (%) | Heterozygous for genomic maturity region: | | | | |
|---|---|---|---|---|---|---|
| | | 1 | 2 | 3 | 4 | 5 |
| MG III.5 parent | 98.7 | | | | | |
| MG 000 parent | 2.6 | | | | | |
| Progeny: 0050 | 86.2 | x | | | x | x |
| Progeny: 0107 | 85.8 | | | x | x | |
| Progeny: 0050 | 84.9 | x | x | | | |
| Progeny: 0093 | 84.9 | x | | x | | |
| Progeny: 0050 | 82.8 | | x | x | x | x |
| Progeny: 0096 | 82.8 | | | | x | x |
| Progeny: 0107 | 82.3 | | x | | | |
| Progeny: 0096 | 81.9 | x | | | x | |
| Progeny: 0107 | 81.5 | x | x | x | x | x |
| Progeny: 0066 | 60.8 | | | | x | |
| Progeny: 0096 | 84.1 | x | | | x | x |
| Progeny: 0093 | 82.8 | x | x | | | |
| Progeny: 0050 | 81.9 | x | | | x | x |
| Progeny: 0050 | 81.9 | x | | | x | |
| Progeny: 0096 | 81.0 | x | | | x | |
| Progeny: 0046 | 80.6 | | x | x | x | x |
| Progeny: 0050 | 80.2 | x | x | x | | |
| Progeny: 0107 | 80.2 | x | | | x | x |
| Progeny: 0093 | 80.2 | x | | | x | |
| Progeny: 0096 | 80.2 | | x | | | |
| Progeny: 0093 | 79.7 | x | | | x | |
| Progeny: 0063 | 79.7 | | | x | x | |
| Progeny: 0093 | 79.3 | | x | x | | x |
| Progeny: 0096 | 78.9 | x | | x | | |
| Progeny: 0012 | 78.9 | x | | | x | x |
| Progeny: 0085 | 78.4 | x | | x | x | |
| Progeny: 0096 | 78.0 | x | | | | |
| Progeny: 0107 | 77.6 | x | | x | | |
| Progeny: 0063 | 74.6 | | x | x | x | |
| Progeny: 0063 | 74.1 | x | | x | | |
| Progeny: 0012 | 61.2 | x | x | x | | |
| Progeny: 0036 | 61.2 | x | x | x | | |
| Progeny: 0012 | 61.2 | x | x | | | |
| Progeny: 0093 | 61.2 | x | | x | x | x |
| Progeny: 0012 | 61.2 | x | | x | | x |
| Progeny: 0050 | 61.2 | x | | x | | |
| Progeny: 0036 | 61.2 | x | | x | | |
| Progeny: 0063 | 61.2 | x | | | x | x |
| Progeny: 0050 | 61.2 | x | | | x | |
| Progeny: 0012 | 61.2 | x | | | x | |
| Progeny: 0107 | 61.2 | x | | | | |
| Progeny: 0012 | 61.2 | x | | | | |
| Progeny: 0012 | 60.8 | x | | x | x | |
| Progeny: 0012 | 60.8 | x | | x | x | |
| Progeny: 0012 | 60.8 | x | | x | x | |
| Progeny: 0050 | 60.8 | x | | x | | |
| Progeny: 0012 | 60.8 | x | | | x | |
| Progeny: 0036 | 60.8 | x | | | x | |
| Progeny: 0012 | 60.8 | x | | | | |
| Progeny: 0012 | 60.8 | x | | | | |
| Progeny: 0036 | 60.8 | | x | x | x | |
| Progeny: 0012 | 60.8 | | | x | x | |
| Progeny: 0012 | 60.3 | x | x | | | |
| Progeny: 0093 | 59.9 | x | x | x | x | |
| Progeny: 0096 | 59.9 | x | | x | x | |
| Progeny: 0012 | 59.9 | x | | x | | |
| Progeny: 0050 | 59.9 | | x | x | | x |
| Progeny: 0085 | 59.9 | | x | x | | x |
| Progeny: 0050 | 59.5 | x | x | | | |
| Progeny: 0096 | 59.5 | x | x | | x | |
| Progeny: 0036 | 59.5 | x | x | | x | |
| Progeny: 0096 | 59.5 | x | | x | x | x |
| Progeny: 0063 | 59.5 | x | | x | | |
| Progeny: 0036 | 59.5 | x | | x | | |
| Progeny: 0096 | 59.5 | | x | | | x |
| Progeny: 0093 | 58.6 | x | x | | x | |
| Progeny: 0050 | 58.6 | x | | | | x |
| Progeny: 0050 | 58.6 | x | | | | |
| Progeny: 0093 | 58.6 | x | | x | x | |
| Progeny: 0093 | 58.2 | x | x | | | |
| Progeny: 0012 | 58.2 | x | x | | x | |
| Progeny: 0012 | 58.2 | x | | | x | x |
| Progeny: 0050 | 58.2 | x | | | x | |
| Progeny: 0012 | 58.2 | x | | | x | |

TABLE 13-continued

Summary of heterozygousity for maturity genomic regions with the F2 generation of MG III.5 parent/(MG III.5 parent * 2/MG 000 parent). Individuals within the population are selected for a geographic maturity group region with SNP markers associated maturity genomic regions.

| Plant | Similarity to MGIII.5 parent (%) | Heterozygous for genomic maturity region: | | | | |
|---|---|---|---|---|---|---|
| | | 1 | 2 | 3 | 4 | 5 |
| Progeny: 0012 | 58.2 | x | | x | | |
| Progeny: 0143 | 58.2 | x | | x | | |
| Progeny: 0096 | 58.2 | x | | | x | |
| Progeny: 0050 | 58.2 | x | | | x | |
| Progeny: 0012 | 57.8 | x | x | | x | |
| Progeny: 0050 | 57.8 | x | x | | x | |
| Progeny: 0012 | 57.8 | x | | x | | |
| Progeny: 0093 | 57.8 | x | | | x | |
| Progeny: 0093 | 57.8 | x | | | | |
| Progeny: 0012 | 57.8 | | x | | x | x |
| Progeny: 0012 | 57.8 | | | x | x | |
| Progeny: 0012 | 57.8 | | | x | x | |
| Progeny: 0096 | 57.3 | x | | x | x | |
| Progeny: 0050 | 56.9 | x | x | | x | |
| Progeny: 0093 | 56.9 | x | | x | x | |
| Progeny: 0050 | 56.9 | x | | x | x | |
| Progeny: 0050 | 56.9 | x | | x | | |
| Progeny: 0050 | 56.9 | | | x | | x |
| Progeny: 0096 | 55.6 | x | x | | x | x |

Example 7

Estimating Effect of Genomic Regions Associated with Maturity

Each allele of each individual maturity genomic region is associated with a value that can either increase or decrease the relative maturity of a given line. The relative maturity of a given line are predicted by using an additive or epistatic model. The example in Table 14 demonstrates predicting relative maturity based on the allelic combination of the maturity genomic regions. The maturity group of a soybean seed is predicted by the composition of maturity genomic region alleles.

TABLE 14

An example of predicting relative maturity based on additive model

| Maturity genomic | Δ Days | Direction |
|---|---|---|
| 1 | 10 | 10 |
| 2 | 5 | −5 |
| 3 | 3 | −3 |
| 4 | 2 | 2 |
| 5 | 6 | 6 |
| 6 | 4 | 4 |
| 7 | 5 | −5 |
| Sum | | 9 |
| Constant | | 3 |
| Maturity Days | | 12 |
| Maturity Group | | 1.2 |

Example 8

Utilization of Molecular Markers Associated with Plant Maturity to Facilitate Crosses with Exotic Germplasm The genetic base of cultivated soybean is narrow compared to other field crops. Eighty to ninety percent of cultivated soybean gene pool are traced to 12 plant introductions in northern United State and seven plant introductions in southern United States. Due to the narrow genetic base, soybean is more likely to be impacted by disease and insect attacks. Exotic germplasm helps expand the genetic base of soybean. In addition, exotic germplasm possesses such key traits as disease resistance, insect resistance, nematode resistance, and tolerance to environmental stress. At present, many exotic species are inaccessible in part due to limitations with crossing soybean plants from extremely different maturity groups. Traditionally, breeders must produce and maintain large numbers of progeny plants from crosses between exotic and cultivated germplasm, in order for breeders to select for a small number soybean plants of the desired maturity group. It is often cost prohibitive to maintain the large number of plants required.

Molecular markers associated with plant maturity facilitate the used of exotic germplasm. Breeders create crosses between exotic and cultivated germplasm. The progeny seed is assayed for plant maturity without expending the resources required to plant and grow large numbers of progeny.

Example 9

Utilization of Molecular Markers Associated with Plant Maturity to Facilitate Introgression of a Transgene After a transgene is introduced into a variety, it may readily be transferred to other varieties by crossing. Most soybean variety development crosses are made between parents within 10 maturity days of each other. When parents differ in plant maturity greater than 10 days, the progeny of the cross segregate widely for plant maturity. In order for breeders to obtain and select for soybean plants of the desire maturity group, they must produce and maintain a large number of progeny plants, the practice of which is cost prohibitive. If a transgene is present in a maturity group III variety needs to be transferred to maturity group 0, a direct cross between a maturity group III variety and a maturity group 0 variety is not typically performed. Instead, the transgene is transferred through a series of intermediate crosses between varieties close in plant maturity. Molecular markers associated with plant maturity genomic regions allows breeders to cross parents that differ in maturity greater than 10 days, then select seed of the cross based on the presence of the transgene and the plant maturity phenotype.

Example 10

Utilization of Molecular Markers Associated with Plant Maturity to Facilitate Introgression of a Trait If a variety possesses a desirable trait, it may readily be transferred to other varieties by crossing. Most soybean variety development crosses are made between parents within 10 maturity days of each other. When the parents differ in plant maturity greater than 10 days, the progeny of the cross segregate widely for plant maturity. In order for breeders to obtain and select for soybean plants of the desire maturity group, they must produce and maintain a large number of progeny plants, the practice of which is cost prohibitive. If a trait is present in a maturity group III variety needs to be transferred to maturity group 0, a direct cross between a maturity group III variety and a maturity group 0 variety is typically not performed. Instead, the trait is transferred through a series of intermediate crosses between varieties close in plant maturity. Molecular markers associated with plant maturity genomic regions allow breeders to cross with parents that differ in maturity by greater than 10 days and to select seed of the cross based on the presence of the trait and the plant maturity phenotype.

Example 11

Utilization of Molecular Markers Associated with Plant Maturity to Select Environments to Optimize Expression of Traits Soybeans cultivated in different environments often perform differently. For instance, a soybean variety may produce seeds with a particular fatty acid profile in one environment and a different fatty acid profile in another environment. A number of environmental factors can influence the expression of traits, including soil type, soil conditions, temperature, photoperiod, geography and cultural practices. Variation in performance of genotypes across different environments is often referred to genotype×environment interactions.

Soybean seed oil levels are highly impacted by environment. Oil concentration increases with decreasing latitude, therefore, soybeans in maturity groups 00-I generally have lower oil levels than later maturing soybeans (FIG. 1). Molecular markers associated with plant maturity assist breeders in selecting soybean genotypes and produce plants that are better adapted to a maturity group region to produce higher oil.

Figure 2:
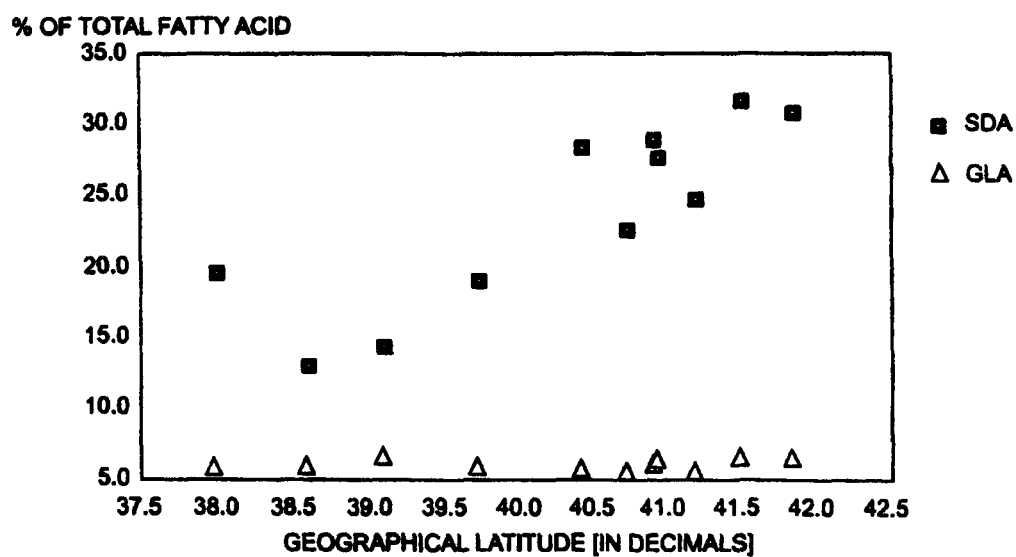
FIG. 2: Correlation of stearidonic acid (SDA) levels and GLA (gamma-linolenic acid) and latitude for mature soybean seeds. The soybean plants are transgenic and engineered to produce SDA and GLA.
Figure 3:
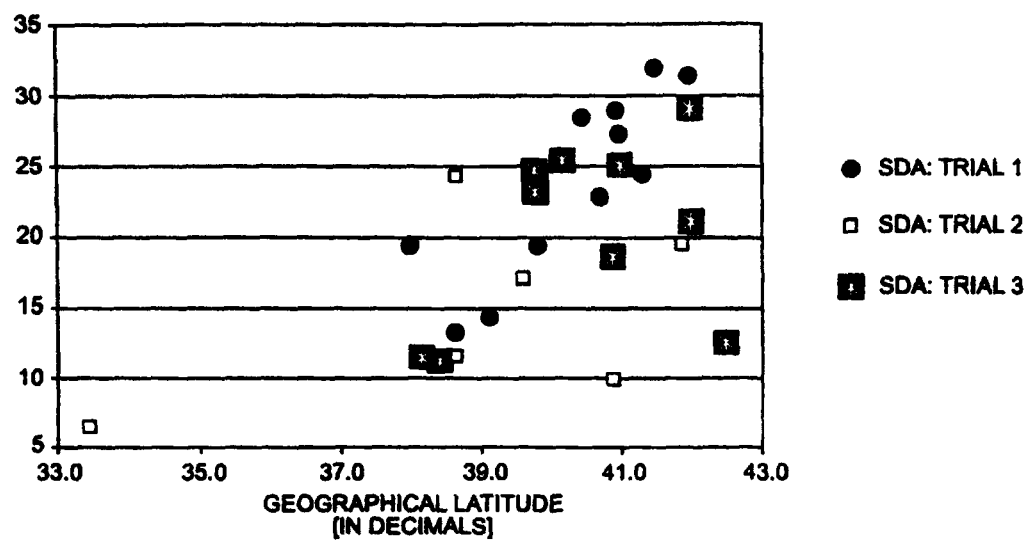
FIG. 3: Correlation of stearidonic acid (SDA) levels and latitude for mature soybean seeds over three trials. The soybean plants are transgenic and engineered to produce SDA.

Soybean seed fatty acid composition is highly impacted by the latitude of cultivation. The present invention provides molecular markers associated with plant maturity which are useful for assisting plant breeders to select favorable soybean maturity genotypes to optimize the expression of particular traits in specific geographies, such as fatty acid synthesis, wherein the trait is conventional or transgenic. As used herein, conventional traits include those obtained by mutagenesis. For example, the profile of fatty transgenic soybean plants engineered to produce stearidonic acid (SDA) have a positive correlation with latitude for SDA production and have a negative correlation with latitude for oleic acid, stearic acid, palmitic acid and α-linolenic acid production (Table 15). The percent of SDA increases with increasing latitude (FIGS. 2-3).

TABLE 15

Correlation of longitude and latitude on fatty acids for mature soybean seed

| Fatty Acid | Latitude | | | Longitude | | |
| --- | --- | --- | --- | --- | --- | --- |
| | R | P value | N | R | P value | N |
| stearidonic acid | 0.6625* | 3.12E−10 | 71 | −0.3748 | 0.001281263 | 71 |
| γ-linolenic acid | 0.1097 | 0.362504877 | 71 | −0.0798 | 0.508051934 | 71 |
| oleic acid | −0.4081* | 0.000411819 | 71 | 0.167 | 0.16389379 | 71 |
| linoleic acid | −0.1581 | 0.187769857 | 71 | 0.0837 | 0.48752276 | 71 |
| α-linolenic acid | −0.2403* | 0.043495686 | 71 | 0.1901 | 0.112261464 | 71 |
| palmitic acid | −0.7305* | 4.82E−13 | 71 | 0.4592 | 5.62E−05 | 71 |
| stearic acid | −0.258* | 0.029810388 | 71 | −0.1498 | 0.212583113 | 71 |

*significant at 0.05 level

Latitude is closely related with maturity groups and growing regions. Soybeans are classified into 13 maturity groups (000, 00, 0, I-X) according to the range in latitude in which the plants are adapted and most productive. Group 000 are the earliest maturing and cultivated at the higher latitudes and Group X are the latest maturing and cultivated in lower latitudes. Molecular markers associated with plant maturity will assist breeders in selecting soybean genotypes that are adapted to latitudes known to be associated with preferred SDA production in the plants. As a result, the soybean breeders more efficiently produce plants that are better adapted to the environment and produce higher levels of SDA or other similar traits.

It is within the scope of this invention to utilize the methods and compositions for preferred trait integration for any trait, conventional or transgenic, affected or influenced by latitude. It is contemplated by the inventors that the present invention will be useful for trait integration of one or more phenotypic traits that are influenced by latitude such that the methods and compositions provided herein will facilitate deployment of one or more traits into preferred germplasm based on maturity, wherein the traits can be conventional or transgenic.

Having illustrated and described the principles of the present invention, it should be apparent to persons skilled in the art that the invention can be modified in arrangement and detail without departing from such principles. We claim all modifications that are within the spirit, scope and concept of the appended claims.

What is claimed is:

1. A method of establishing where a soybean plant or soybean seed should be grown by determining an allelic combination of a soybean plant or soybean seed, comprising:
   a. obtaining DNA from said soybean plant or soybean seed;
   b. determining the genotype of said soybean plant or soybean seed by
      i. determining if alleles at a locus within maturity genomic region 1 are homozygous or heterozygous by detecting via an assay a first maturity marker genetically linked to said maturity genomic region 1, and said first maturity marker is located within 20 centiMorgans (cM) of SEQ ID NO: 149;
      ii. determining if alleles at a locus within maturity genomic region 2 are homozygous or heterozygous by detecting via an assay a second maturity marker genetically linked to said maturity genomic region 2, and said second maturity marker is located within 20 cM of SEQ ID NO: 158;
      iii. determining if alleles at a locus within maturity genomic region 3 are homozygous or heterozygous by detecting via an assay a third maturity marker genetically linked to said maturity genomic region 3, and said third maturity marker is located within 20 cM of SEQ ID NO: 169;
   c. determining said allelic combination of said alleles within maturity genomic regions 1, 2, and 3; and
   d. assigning a maturity group value to said soybean plant or soybean seed based on said allelic combination.

2. The method of claim 1, further comprising selecting multiple soybean seeds.

3. The method of claim 2, wherein said multiple soybean seeds are capable of growing into soybean plants having indeterminate soybean plant habit.

4. The method of claim 1, wherein said first maturity marker is located within 10 cM of said SEQ ID NO: 149.

5. A method of establishing where a soybean plant or soybean seed should be grown by determining an allelic combination of said soybean plant or soybean seed, comprising:
   a. obtaining DNA from said soybean plant or soybean seed;
   b. determining the genotype of said soybean plant or soybean seed by i. determining if alleles at a locus within maturity genomic region 1 is homozygous or heterozygous by detecting via an assay a first maturity marker genetically linked to said maturity genomic region 1, and said first maturity marker is located within 20 cM of SEQ ID NO: 149;

ii. determining if alleles at a locus within maturity genomic region 2 is homozygous or heterozygous by detecting via an assay a second maturity marker genetically linked to said maturity genomic region 2, and said second maturity marker is located within 20 cM of SEQ ID NO: 158;

c. determining said allelic combination of said alleles within maturity genomic regions 1 and 2; and d. assigning a maturity growth value to said soybean plant or soybean seed based on said allelic combination.

6. The method of claim 5, wherein said determining if alleles at said locus within said maturity genomic region 1 or 2 are homozygous or heterozygous comprises detecting via an assay at least one polymorphism within 10 cM of said SEQ ID NO: 149.

7. The method of claim 5, wherein said soybean plant or soybean seed is obtained from a cross of an early maturity group parent soybean plant and a mid maturity parent soybean plant.

8. The method of claim 7, wherein said early maturity group parent soybean plant is between 00.0-I.0 and said mid maturity parent soybean plant is between III.0-IV.9.

9. A method of soybean plant breeding, comprising:
a. crossing a parent soybean plant comprising a desired trait with a second parent soybean plant, wherein said first and second parent soybean plants differ in plant maturity by over 10 days;
b. obtaining progeny soybean seeds from said cross;
c. screening a progeny soybean seed for said desired trait; and
d. selecting a screened progeny soybean plant from step c containing said desired trait and a desired soybean plant maturity by
determining if alleles at a locus within maturity genomic region 1 are homozygous or heterozygous by detecting via an assay a first maturity marker genetically linked to said maturity genomic region 1, and said first maturity marker is located within 20 cM of SEQ ID NO: 149,
determining if alleles at a locus within maturity genomic region 2 are homozygous or heterozygous by detecting via an assay a second maturity marker genetically linked to said maturity genomic region 2, and said second maturity marker is located within 20 cM of SEQ ID NO: 158,
determining an allelic combination of said alleles within maturity genomic regions 1 and 2, and
assigning a maturity growth value to said screened progeny soybean seed based on said allelic combination.

10. The method of claim 9, where said desired trait is transgenic.

11. A method of distributing a soybean plant or seed based on maturity group, comprising:
a. obtaining DNA from said soybean plant or seed;
b. determining the genotype of said soybean plant or seed by
i. determining if an allele within maturity genomic region 1 is homozygous or heterozygous by detecting via an assay a first maturity marker genetically linked to said maturity genomic region 1, and said first maturity marker is located within 20 cM of SEQ ID NO: 149;

ii. determining if an allele within maturity genomic region 2 is homozygous or heterozygous by detecting via an assay a second maturity marker genetically linked to said maturity genomic region 2, and said second maturity marker is located within 20 cM of SEQ ID NO: 158;

iii. determining if an allele within maturity genomic region 3 is homozygous or heterozygous by detecting via an assay a third maturity marker genetically linked to said maturity genomic region 3, and said third maturity marker is located within 20 cM of SEQ ID NO: 169;

c. assigning a maturity growth value to said soybean plant based on an allelic combination of said alleles within maturity genomic regions 1, 2, and 3; and d. shipping said soybean plant to a preferred geographic region.

12. A method to isolate indeterminate-early maturity soybean seeds, comprising:
a. obtaining DNA from a soybean seed using a non-destructive method;
b. determining the genotype of said soybean seed by
i. determining if an allele within maturity genomic region 1 is homozygous or heterozygous by detecting via an assay a first maturity marker genetically linked to said maturity genomic region 1, and said first maturity marker is located within 20 cM of SEQ ID NO: 149; and ii. determining if an allele within maturity genomic region 2 is homozygous or heterozygous by detecting via an assay a second maturity marker genetically linked to said maturity genomic region 2, and said second maturity marker is located within 20 cM of SEQ ID NO: 158.

13. A method to determine if a soybean seed has a maturity group of 0.0-III.9, comprising:
a. obtaining DNA from said soybean seed using a non-destructive method;
b. determining the genotype of said soybean seed by
i. determining if an allele within maturity genomic region 1 is homozygous or heterozygous by detecting via an assay a first maturity marker genetically linked to said maturity genomic region 1, and said first maturity marker is located within 20 cM of SEQ ID NO: 149;

ii. determining if an allele within maturity genomic region 2 is homozygous or heterozygous by detecting via an assay a second maturity marker genetically linked to said maturity genomic region 2, and said second maturity marker is located within 20 cM of SEQ ID NO: 158; and c. assigning a maturity group value for said soybean seed between 0.0-III.9 based on an allelic combination of said alleles within maturity genomic regions 1 and 2.

14. The method of claim 13, wherein a soybean plant grown from said soybean seed reaches maturity at least 5 days before a soybean plant that is homozygous dominant within maturity genomic regions 1 and 2 and is grown under the same environmental conditions.

15. A method to determine if the maturity of a soybean plant is in a 00.0-III.0 maturity group, comprising:
a. obtaining DNA from said soybean plant
b. determining the genotype of said soybean plant by
i. determining if an allele within maturity genomic region 1 is homozygous or heterozygous by detecting via an assay a first maturity marker genetically linked to said maturity genomic region 1, and said first maturity marker is located within 20 cM of SEQ ID NO: 149;

ii. determining if an allele within maturity genomic region 2 is homozygous or heterozygous by detecting via an assay a second maturity marker genetically linked to said maturity genomic region 2, and said second maturity marker is located within 20 cM of SEQ ID NO: 158; and c. assigning a maturity group value for said soybean plant between 00.0-III.0 based on an allelic combination of said alleles within maturity genomic regions 1 and 2; wherein said first and second maturity markers are molecular markers.

16. The method of claim 15, further comprising selecting a soybean seed that is homozygous recessive at maturity genomic region 1 and homozygous recessive at maturity genomic region 2 and has a maturity group between 0.5-II.0.

17. The method of claim 15, further comprising selecting a soybean seed that is homozygous recessive at maturity genomic region 1 and heterozygous dominant at maturity genomic region 2 and has a maturity group between I.5-II.9.

18. The method of claim 9, further comprising determining if alleles at a locus within maturity genomic region 3 are homozygous or heterozygous by detecting via an assay a third maturity marker genetically linked to said maturity genomic region 3, and said third maturity marker is located within 20 cM of SEQ ID NO: 169.

19. The method of claim 1, wherein said first maturity marker is located within 10 cM of said SEQ ID NO: 149; wherein said second maturity marker is located within 10 cM of said SEQ ID NO: 158; and said third maturity marker is located within 10 cM of said SEQ ID NO: 169.

20. The method of claim 19, wherein said first maturity marker is located within 5 cM of SEQ ID NO: 149; wherein said second maturity marker is located within 5 cM of said SEQ ID NO: 158; and said third maturity marker is located within 5 cM of said SEQ ID NO: 169.

21. The method of claim 20, wherein said first maturity marker is located within 1 cM of said SEQ ID NO: 149; wherein said second maturity marker is located within 1 cM of said SEQ ID NO: 158; and said third maturity marker is located within 1 cM of said SEQ ID NO: 169.

22. The method of claim 21, wherein said first maturity marker comprises SEQ ID NO: 149; wherein said second maturity marker comprises SEQ ID NO: 158; and said third maturity marker comprises SEQ ID NO: 169.

23. The method of claim 9, wherein said first maturity marker is located within 10 cM of SEQ ID NO: 149; and wherein said second maturity marker is located within 10 cM of said SEQ ID NO: 158.

24. The method of claim 23, wherein said first maturity marker is located within 5 cM of SEQ ID NO: 149; and wherein said second maturity marker is located within 5 cM of said SEQ ID NO: 158.

25. The method of claim 24, wherein said first maturity marker is located within 1 cM of SEQ ID NO: 149; and wherein said second maturity marker is located within 1 cM of said SEQ ID NO: 158.

26. The method of claim 25, wherein said first maturity marker comprises SEQ ID NO: 149; and wherein said second maturity marker comprises SEQ ID NO: 158.

27. The method of claim 11, wherein said first maturity marker is located within 10 cM of SEQ ID NO: 149; wherein said second maturity marker is located within 10 cM of said SEQ ID NO: 158; and said third maturity marker is located within 10 cM of said SEQ ID NO: 169.

28. The method of claim 27, wherein said first maturity marker is located within 5 cM of SEQ ID NO: 149; wherein said second maturity marker is located within 5 cM of said SEQ ID NO: 158; and said third maturity marker is located within 5 cM of said SEQ ID NO: 169.

29. The method of claim 28, wherein said first maturity marker is located within 1 cM of SEQ ID NO: 149; wherein said second maturity marker is located within 1 cM of said SEQ ID NO: 158; and said third maturity marker is located within 1 cM of said SEQ ID NO: 169.

30. The method of claim 29, wherein said first maturity marker comprises SEQ ID NO: 149; wherein said second maturity marker comprises SEQ ID NO: 158; and said third maturity marker is comprises SEQ ID NO: 169.

31. The method of claim 1, wherein said determining the genotype of said soybean plant or soybean seed further comprises determining if alleles at a locus within maturity genomic region 4, 5, 6, 7, or 8 are homozygous or heterozygous.

32. The method of claim 9, wherein said determination of an allelic combination further comprises determining if alleles at a locus within maturity genomic region 3, 4, 5, 6, 7, or 8 are homozygous or heterozygous.

33. The method of claim 11, wherein said determining the genotype of said soybean plant or soybean seed further comprises determining if alleles at a locus within maturity genomic region 4, 5, 6, 7, or 8 are homozygous or heterozygous.

* * * * *

UNITED STATES PATENT AND TRADEMARK OFFICE
CERTIFICATE OF CORRECTION

PATENT NO. : 8,847,006 B2
APPLICATION NO. : 12/078173
DATED : September 30, 2014
INVENTOR(S) : Jonathan Jenkinson et al.

Page 1 of 1

It is certified that error appears in the above-identified patent and that said Letters Patent is hereby corrected as shown below:

On the title page item (74), please change "Lawrence Levin, Jr." to --Lawrence Lavin, Jr.--.

In the Claims,

In Claim 30 (column 212, line 34), please change "marker is comprises" to --marker comprises--.

Signed and Sealed this
Twentieth Day of January, 2015

Michelle K. Lee
*Deputy Director of the United States Patent and Trademark Office*

SEQUENCE LISTING

<160> NUMBER OF SEQ ID NOS: 356

<210> SEQ ID NO 1
<211> LENGTH: 18
<212> TYPE: DNA
<213> ORGANISM: Artificial sequence
<220> FEATURE:
<223> OTHER INFORMATION: Synthetic Primer

<400> SEQUENCE: 1
tgggtgaccc cgaagttg

<210> SEQ ID NO 2
<211> LENGTH: 24
<212> TYPE: DNA
<213> ORGANISM: Artificial sequence
<220> FEATURE:
<223> OTHER INFORMATION: Synthetic Primer

<400> SEQUENCE: 2
ggcagattcg atactctcgt acgt                                           24

<210> SEQ ID NO 3
<211> LENGTH: 19
<212> TYPE: DNA
<213> ORGANISM: Artificial sequence
<220> FEATURE:
<223> OTHER INFORMATION: Synthetic Primer

<400> SEQUENCE: 3
cgcctgggag caacaagat                                                 19

<210> SEQ ID NO 4
<211> LENGTH: 21
<212> TYPE: DNA
<213> ORGANISM: Artificial sequence
<220> FEATURE:
<223> OTHER INFORMATION: Synthetic Primer

<400> SEQUENCE: 4
ttcgaagaat gggagcagaa a                                              21

<210> SEQ ID NO 5
<211> LENGTH: 27
<212> TYPE: DNA
<213> ORGANISM: Artificial sequence
<220> FEATURE:
<223> OTHER INFORMATION: Synthetic Primer

<400> SEQUENCE: 5
cataagacgc gttaaacgtc agtactt                                        27

<210> SEQ ID NO 6
<211> LENGTH: 26
<212> TYPE: DNA
<213> ORGANISM: Artificial sequence
<220> FEATURE:
<223> OTHER INFORMATION: Synthetic Primer

<400> SEQUENCE: 6
ccaacgatct tgctaattag cacata                                         26

<210> SEQ ID NO 7
<211> LENGTH: 22
<212> TYPE: DNA
<213> ORGANISM: Artificial sequence
<220> FEATURE:
<223> OTHER INFORMATION: Synthetic Primer

<400> SEQUENCE: 7
atgggcaaca gttgtcatat gg                                             22

<210> SEQ ID NO 8
<211> LENGTH: 24
<212> TYPE: DNA
<213> ORGANISM: Artificial sequence
<220> FEATURE:

```
<223> OTHER INFORMATION: Synthetic Primer

<400> SEQUENCE: 8
tgatgatggc atggaattat tacc                                      24

<210> SEQ ID NO 9
<211> LENGTH: 26
<212> TYPE: DNA
<213> ORGANISM: Artificial sequence
<220> FEATURE:
<223> OTHER INFORMATION: Synthetic Primer

<400> SEQUENCE: 9
atttttggta cctctctttc cttcaa                                    26

<210> SEQ ID NO 10
<211> LENGTH: 26
<212> TYPE: DNA
<213> ORGANISM: Artificial sequence
<220> FEATURE:
<223> OTHER INFORMATION: Synthetic Primer

<400> SEQUENCE: 10
ttattaccaa catccaaaca cacaca                                    26

<210> SEQ ID NO 11
<211> LENGTH: 20
<212> TYPE: DNA
<213> ORGANISM: Artificial sequence
<220> FEATURE:
<223> OTHER INFORMATION: Synthetic Primer

<400> SEQUENCE: 11
cgaggttgtt agccgttgga                                           20

<210> SEQ ID NO 12
<211> LENGTH: 26
<212> TYPE: DNA
<213> ORGANISM: Artificial sequence
<220> FEATURE:
<223> OTHER INFORMATION: Synthetic Primer

<400> SEQUENCE: 12
accaatcaac ctttctttat cgtttt                                    26

<210> SEQ ID NO 13
<211> LENGTH: 23
<212> TYPE: DNA
<213> ORGANISM: Artificial sequence
<220> FEATURE:
<223> OTHER INFORMATION: Synthetic Primer

<400> SEQUENCE: 13
catttcttca acatccgaac caa                                       23

<210> SEQ ID NO 14
<211> LENGTH: 24
<212> TYPE: DNA
<213> ORGANISM: Artificial sequence
<220> FEATURE:
<223> OTHER INFORMATION: Synthetic Primer

<400> SEQUENCE: 14
ggaggaaggg tatgcaactt ttac                                      24
```

```
<210> SEQ ID NO 15
<211> LENGTH: 30
<212> TYPE: DNA
<213> ORGANISM: Artificial sequence
<220> FEATURE:
<223> OTHER INFORMATION: Synthetic Primer

<400> SEQUENCE: 15
cctcgagtta ttggtatgag atattttatg                                    30

<210> SEQ ID NO 16
<211> LENGTH: 27
<212> TYPE: DNA
<213> ORGANISM: Artificial sequence
<220> FEATURE:
<223> OTHER INFORMATION: Synthetic Primer

<400> SEQUENCE: 16
aaaacggtat atttaacatc caaagca                                       27

<210> SEQ ID NO 17
<211> LENGTH: 23
<212> TYPE: DNA
<213> ORGANISM: Artificial sequence
<220> FEATURE:
<223> OTHER INFORMATION: Synthetic Primer

<400> SEQUENCE: 17
tggaagcaat gtcaatcaat tca                                           23

<210> SEQ ID NO 18
<211> LENGTH: 22
<212> TYPE: DNA
<213> ORGANISM: Artificial sequence
<220> FEATURE:
<223> OTHER INFORMATION: Synthetic Primer

<400> SEQUENCE: 18
tccatggcat ccttaagggt aa                                            22

<210> SEQ ID NO 19
<211> LENGTH: 25
<212> TYPE: DNA
<213> ORGANISM: Artificial sequence
<220> FEATURE:
<223> OTHER INFORMATION: Synthetic Primer

<400> SEQUENCE: 19
caattttatt cttggcacct tcatt                                         25

<210> SEQ ID NO 20
<211> LENGTH: 24
<212> TYPE: DNA
<213> ORGANISM: Artificial sequence
<220> FEATURE:
<223> OTHER INFORMATION: Synthetic Primer

<400> SEQUENCE: 20
gtgaagtgta ttccagtggt gtga                                          24

<210> SEQ ID NO 21
<211> LENGTH: 30
<212> TYPE: DNA
<213> ORGANISM: Artificial sequence
<220> FEATURE:
<223> OTHER INFORMATION: Synthetic Primer
```

<400> SEQUENCE: 21
acttctggaa ttgaggattt atttaaagac                                    30

<210> SEQ ID NO 22
<211> LENGTH: 27
<212> TYPE: DNA
<213> ORGANISM: Artificial sequence
<220> FEATURE:
<223> OTHER INFORMATION: Synthetic Primer

<400> SEQUENCE: 22 cttttgtgg tttttctgga gttaaac                                        27

<210> SEQ ID NO 23
<211> LENGTH: 23
<212> TYPE: DNA
<213> ORGANISM: Artificial sequence
<220> FEATURE:
<223> OTHER INFORMATION: Synthetic Primer

<400> SEQUENCE: 23
ccttcccgta aactgaatga tca                                           23

<210> SEQ ID NO 24
<211> LENGTH: 27
<212> TYPE: DNA
<213> ORGANISM: Artificial sequence
<220> FEATURE:
<223> OTHER INFORMATION: Synthetic Primer

<400> SEQUENCE: 24
tgtgggcagt tttgaataat tagtttc                                       27

<210> SEQ ID NO 25
<211> LENGTH: 22
<212> TYPE: DNA
<213> ORGANISM: Artificial sequence
<220> FEATURE:
<223> OTHER INFORMATION: Synthetic Primer

<400> SEQUENCE: 25
accgtgtcct taaagctttc ca                                            22

<210> SEQ ID NO 26
<211> LENGTH: 27
<212> TYPE: DNA
<213> ORGANISM: Artificial sequence
<220> FEATURE:
<223> OTHER INFORMATION: Synthetic Primer

<400> SEQUENCE: 26
aaggttatat aaatcaaggg gaatgct                                       27

<210> SEQ ID NO 27
<211> LENGTH: 25
<212> TYPE: DNA
<213> ORGANISM: Artificial sequence
<220> FEATURE:
<223> OTHER INFORMATION: Synthetic Primer

<400> SEQUENCE: 27
aaccatctgg atatttcaac caaaa                                         25

<210> SEQ ID NO 28
<211> LENGTH: 25

```
<212> TYPE: DNA
<213> ORGANISM: Artificial sequence
<220> FEATURE:
<223> OTHER INFORMATION: Synthetic Primer

<400> SEQUENCE: 28
ctcacttttg cctttgttag agcat                                           25

<210> SEQ ID NO 29
<211> LENGTH: 27
<212> TYPE: DNA
<213> ORGANISM: Artificial sequence
<220> FEATURE:
<223> OTHER INFORMATION: Synthetic Primer

<400> SEQUENCE: 29
cgaagcatta cactattttc tgtcaaa                                         27

<210> SEQ ID NO 30
<211> LENGTH: 29
<212> TYPE: DNA
<213> ORGANISM: Artificial sequence
<220> FEATURE:
<223> OTHER INFORMATION: Synthetic Primer

<400> SEQUENCE: 30
aaaaaatcac atgatacgag aaaagatct                                       29

<210> SEQ ID NO 31
<211> LENGTH: 25
<212> TYPE: DNA
<213> ORGANISM: Artificial sequence
<220> FEATURE:
<223> OTHER INFORMATION: Synthetic Primer

<400> SEQUENCE: 31
cctttcaaaa cctttaaggc atgta                                           25

<210> SEQ ID NO 32
<211> LENGTH: 25
<212> TYPE: DNA
<213> ORGANISM: Artificial sequence
<220> FEATURE:
<223> OTHER INFORMATION: Synthetic Primer

<400> SEQUENCE: 32
gttcctagcc aacaatgagt ttctc                                           25

<210> SEQ ID NO 33
<211> LENGTH: 30
<212> TYPE: DNA
<213> ORGANISM: Artificial sequence
<220> FEATURE:
<223> OTHER INFORMATION: Synthetic Primer

<400> SEQUENCE: 33
cttagtgagc tatgtctaac ttcaatgctt                                      30

<210> SEQ ID NO 34
<211> LENGTH: 29
<212> TYPE: DNA
<213> ORGANISM: Artificial sequence
<220> FEATURE:
<223> OTHER INFORMATION: Synthetic Primer

<400> SEQUENCE: 34
```

```
actgtaaaca atttagcaat caatttgtg                              29

<210> SEQ ID NO 35
<211> LENGTH: 21
<212> TYPE: DNA
<213> ORGANISM: Artificial sequence
<220> FEATURE:
<223> OTHER INFORMATION: Synthetic Primer

<400> SEQUENCE: 35
tggtctcggc tgtgaattca g                                      21

<210> SEQ ID NO 36
<211> LENGTH: 29
<212> TYPE: DNA
<213> ORGANISM: Artificial sequence
<220> FEATURE:
<223> OTHER INFORMATION: Synthetic Primer

<400> SEQUENCE: 36
aatattccat ttatatactt gcacttgca                              29

<210> SEQ ID NO 37
<211> LENGTH: 23
<212> TYPE: DNA
<213> ORGANISM: Artificial sequence
<220> FEATURE:
<223> OTHER INFORMATION: Synthetic Primer

<400> SEQUENCE: 37
ggagtgttta gagggatgca ttg                                    23

<210> SEQ ID NO 38
<211> LENGTH: 23
<212> TYPE: DNA
<213> ORGANISM: Artificial sequence
<220> FEATURE:
<223> OTHER INFORMATION: Synthetic Primer

<400> SEQUENCE: 38
gcgcctatgt cacttaagct gat                                    23

<210> SEQ ID NO 39
<211> LENGTH: 29
<212> TYPE: DNA
<213> ORGANISM: Artificial sequence
<220> FEATURE:
<223> OTHER INFORMATION: Synthetic Primer

<400> SEQUENCE: 39
ggattagaac tgtttgttgg aagtgatag                              29

<210> SEQ ID NO 40
<211> LENGTH: 30
<212> TYPE: DNA
<213> ORGANISM: Artificial sequence
<220> FEATURE:
<223> OTHER INFORMATION: Synthetic Primer

<400> SEQUENCE: 40
ttatgcaaaa attcatttta agactcattt                             30

<210> SEQ ID NO 41
<211> LENGTH: 23
<212> TYPE: DNA
<213> ORGANISM: Artificial sequence
```

<220> FEATURE:
<223> OTHER INFORMATION: Synthetic Primer

<400> SEQUENCE: 41
acagcaaagg gacacaattc aat        23

<210> SEQ ID NO 42
<211> LENGTH: 27
<212> TYPE: DNA
<213> ORGANISM: Artificial sequence
<220> FEATURE:
<223> OTHER INFORMATION: Synthetic Primer

<400> SEQUENCE: 42
ctctccatat tcaatttgtc aaacttg        27

<210> SEQ ID NO 43
<211> LENGTH: 19
<212> TYPE: DNA
<213> ORGANISM: Artificial sequence
<220> FEATURE:
<223> OTHER INFORMATION: Synthetic Primer

<400> SEQUENCE: 43
tttgggttcc caggtttgc        19

<210> SEQ ID NO 44
<211> LENGTH: 21
<212> TYPE: DNA
<213> ORGANISM: Artificial sequence
<220> FEATURE:
<223> OTHER INFORMATION: Synthetic Primer

<400> SEQUENCE: 44
tgcctcgcca ttaacattag c        21

<210> SEQ ID NO 45
<211> LENGTH: 29
<212> TYPE: DNA
<213> ORGANISM: Artificial sequence
<220> FEATURE:
<223> OTHER INFORMATION: Synthetic Primer

<400> SEQUENCE: 45
agaatttaca gcttgcaggt atttaattt        29

<210> SEQ ID NO 46
<211> LENGTH: 30
<212> TYPE: DNA
<213> ORGANISM: Artificial sequence
<220> FEATURE:
<223> OTHER INFORMATION: Synthetic Primer

<400> SEQUENCE: 46
gcaatagttt gagaagctct actacaattt        30

<210> SEQ ID NO 47
<211> LENGTH: 26
<212> TYPE: DNA
<213> ORGANISM: Artificial sequence
<220> FEATURE:
<223> OTHER INFORMATION: Synthetic Primer

<400> SEQUENCE: 47
ttcccttgta tattgttttg aaatgc        26

<210> SEQ ID NO 48
<211> LENGTH: 26
<212> TYPE: DNA
<213> ORGANISM: Artificial sequence
<220> FEATURE:
<223> OTHER INFORMATION: Synthetic Primer

<400> SEQUENCE: 48
tgcagaaaaa cagaaaaaac tgaagt                                      26

<210> SEQ ID NO 49
<211> LENGTH: 21
<212> TYPE: DNA
<213> ORGANISM: Artificial sequence
<220> FEATURE:
<223> OTHER INFORMATION: Synthetic Primer

<400> SEQUENCE: 49
acaagcatgt tggaccagct t                                           21

<210> SEQ ID NO 50
<211> LENGTH: 25
<212> TYPE: DNA
<213> ORGANISM: Artificial sequence
<220> FEATURE:
<223> OTHER INFORMATION: Synthetic Primer

<400> SEQUENCE: 50
tgcaagggta tgtcatagtg gaatt                                       25

<210> SEQ ID NO 51
<211> LENGTH: 29
<212> TYPE: DNA
<213> ORGANISM: Artificial sequence
<220> FEATURE:
<223> OTHER INFORMATION: Synthetic Primer

<400> SEQUENCE: 51 tagacccttatattttatgtt aatttgcgt                                   29

<210> SEQ ID NO 52
<211> LENGTH: 30
<212> TYPE: DNA
<213> ORGANISM: Artificial sequence
<220> FEATURE:
<223> OTHER INFORMATION: Synthetic Primer

<400> SEQUENCE: 52
atcagtaaaa tggagacaaa tgagtaaaaa                                  30

<210> SEQ ID NO 53
<211> LENGTH: 31
<212> TYPE: DNA
<213> ORGANISM: Artificial sequence
<220> FEATURE:
<223> OTHER INFORMATION: Synthetic Primer

<400> SEQUENCE: 53
gaactgagta tcttttccta gacttgtttc t                                31

<210> SEQ ID NO 54
<211> LENGTH: 26
<212> TYPE: DNA
<213> ORGANISM: Artificial sequence
<220> FEATURE:
<223> OTHER INFORMATION: Synthetic Primer

<400> SEQUENCE: 54
cctaatgttg tagagctcca ggaaag 26

<210> SEQ ID NO 55
<211> LENGTH: 33
<212> TYPE: DNA
<213> ORGANISM: Artificial sequence
<220> FEATURE:
<223> OTHER INFORMATION: Synthetic Primer

<400> SEQUENCE: 55
cataacttcc ttttacatac aatttctata cca 33

<210> SEQ ID NO 56
<211> LENGTH: 30
<212> TYPE: DNA
<213> ORGANISM: Artificial sequence
<220> FEATURE:
<223> OTHER INFORMATION: Synthetic Primer

<400> SEQUENCE: 56
ttattacacc acttgttctt tttaaggaaa 30

<210> SEQ ID NO 57
<211> LENGTH: 26
<212> TYPE: DNA
<213> ORGANISM: Artificial sequence
<220> FEATURE:
<223> OTHER INFORMATION: Synthetic Primer

<400> SEQUENCE: 57
tgtggtccgt tcaaaaatta taatga 26

<210> SEQ ID NO 58
<211> LENGTH: 26
<212> TYPE: DNA
<213> ORGANISM: Artificial sequence
<220> FEATURE:
<223> OTHER INFORMATION: Synthetic Primer

<400> SEQUENCE: 58
caagagaaat ccattaagaa attgca 26

<210> SEQ ID NO 59
<211> LENGTH: 25
<212> TYPE: DNA
<213> ORGANISM: Artificial sequence
<220> FEATURE:
<223> OTHER INFORMATION: Synthetic Primer

<400> SEQUENCE: 59
aaattggtct ttgaaggaaa atgaa 25

<210> SEQ ID NO 60
<211> LENGTH: 21
<212> TYPE: DNA
<213> ORGANISM: Artificial sequence
<220> FEATURE:
<223> OTHER INFORMATION: Synthetic Primer

<400> SEQUENCE: 60
tcctccaaag gttggtgctt t 21

<210> SEQ ID NO 61

```
<210> SEQ ID NO 61
<211> LENGTH: 30
<212> TYPE: DNA
<213> ORGANISM: Artificial sequence
<220> FEATURE:
<223> OTHER INFORMATION: Synthetic Primer

<400> SEQUENCE: 61
tctggcagtt ctatacttct gaaatttaaa                              30

<210> SEQ ID NO 62
<211> LENGTH: 29
<212> TYPE: DNA
<213> ORGANISM: Artificial sequence
<220> FEATURE:
<223> OTHER INFORMATION: Synthetic Primer

<400> SEQUENCE: 62
ctcttaaata gcttatgggt gtatgtcaa                               29

<210> SEQ ID NO 63
<211> LENGTH: 23
<212> TYPE: DNA
<213> ORGANISM: Artificial sequence
<220> FEATURE:
<223> OTHER INFORMATION: Synthetic Primer

<400> SEQUENCE: 63
aaattttgga cccatttctt tgc                                     23

<210> SEQ ID NO 64
<211> LENGTH: 23
<212> TYPE: DNA
<213> ORGANISM: Artificial sequence
<220> FEATURE:
<223> OTHER INFORMATION: Synthetic Primer

<400> SEQUENCE: 64
aattatttgc atttgctctt ggc                                     23

<210> SEQ ID NO 65
<211> LENGTH: 26
<212> TYPE: DNA
<213> ORGANISM: Artificial sequence
<220> FEATURE:
<223> OTHER INFORMATION: Synthetic Primer

<400> SEQUENCE: 65
tgtctgctgg ttgaagtaac ttatgg                                  26

<210> SEQ ID NO 66
<211> LENGTH: 26
<212> TYPE: DNA
<213> ORGANISM: Artificial sequence
<220> FEATURE:
<223> OTHER INFORMATION: Synthetic Primer

<400> SEQUENCE: 66
gctgatagtt tttgcatatt cttcca                                  26

<210> SEQ ID NO 67
<211> LENGTH: 26
<212> TYPE: DNA
<213> ORGANISM: Artificial sequence
<220> FEATURE:
<223> OTHER INFORMATION: Synthetic Primer

<400> SEQUENCE: 67
```

-continued

```
cttgcttaca aattcctcca actaaa                                          26

<210> SEQ ID NO 68
<211> LENGTH: 24
<212> TYPE: DNA
<213> ORGANISM: Artificial sequence
<220> FEATURE:
<223> OTHER INFORMATION: Synthetic Primer

<400> SEQUENCE: 68
gcttaagaac aaccgagagc tttt                                            24

<210> SEQ ID NO 69
<211> LENGTH: 28
<212> TYPE: DNA
<213> ORGANISM: Artificial sequence
<220> FEATURE:
<223> OTHER INFORMATION: Synthetic Primer

<400> SEQUENCE: 69
catgaactgt gattacatat tcttttgc                                        28

<210> SEQ ID NO 70
<211> LENGTH: 20
<212> TYPE: DNA
<213> ORGANISM: Artificial sequence
<220> FEATURE:
<223> OTHER INFORMATION: Synthetic Primer

<400> SEQUENCE: 70
gctgccgaac atgatggtta                                                 20

<210> SEQ ID NO 71
<211> LENGTH: 27
<212> TYPE: DNA
<213> ORGANISM: Artificial sequence
<220> FEATURE:
<223> OTHER INFORMATION: Synthetic Primer

<400> SEQUENCE: 71
cagaagaaag attctatgac tccaaca                                         27

<210> SEQ ID NO 72
<211> LENGTH: 30
<212> TYPE: DNA
<213> ORGANISM: Artificial sequence
<220> FEATURE:
<223> OTHER INFORMATION: Synthetic Primer

<400> SEQUENCE: 72
actgcataaa ataccgtaat attctcttga                                      30

<210> SEQ ID NO 73
<211> LENGTH: 26
<212> TYPE: DNA
<213> ORGANISM: Artificial sequence
<220> FEATURE:
<223> OTHER INFORMATION: Synthetic Primer

<400> SEQUENCE: 73
agaatcatgt gattctgatt gtacga                                          26

<210> SEQ ID NO 74
<211> LENGTH: 26
<212> TYPE: DNA
```

```
<213> ORGANISM: Artificial sequence
<220> FEATURE:
<223> OTHER INFORMATION: Synthetic Primer

<400> SEQUENCE: 74
ggaaccaaaa tccctataac tgttgt                                              26

<210> SEQ ID NO 75
<211> LENGTH: 23
<212> TYPE: DNA
<213> ORGANISM: Artificial sequence
<220> FEATURE:
<223> OTHER INFORMATION: Synthetic Primer

<400> SEQUENCE: 75
attttgggag gacaagtgga ctt                                                 23

<210> SEQ ID NO 76
<211> LENGTH: 28
<212> TYPE: DNA
<213> ORGANISM: Artificial sequence
<220> FEATURE:
<223> OTHER INFORMATION: Synthetic Primer

<400> SEQUENCE: 76
gcaagaaata agatatagcc ttgggtat                                            28

<210> SEQ ID NO 77
<211> LENGTH: 23
<212> TYPE: DNA
<213> ORGANISM: Artificial sequence
<220> FEATURE:
<223> OTHER INFORMATION: Synthetic Primer

<400> SEQUENCE: 77
tggcatcctc ttatcaacaa agc                                                 23

<210> SEQ ID NO 78
<211> LENGTH: 22
<212> TYPE: DNA
<213> ORGANISM: Artificial sequence
<220> FEATURE:
<223> OTHER INFORMATION: Synthetic Primer

<400> SEQUENCE: 78
cctatcagtg ttggtggaag ca                                                  22

<210> SEQ ID NO 79
<211> LENGTH: 22
<212> TYPE: DNA
<213> ORGANISM: Artificial sequence
<220> FEATURE:
<223> OTHER INFORMATION: Synthetic Primer

<400> SEQUENCE: 79
ggtgagccaa ggaaagaaac ac                                                  22

<210> SEQ ID NO 80
<211> LENGTH: 24
<212> TYPE: DNA
<213> ORGANISM: Artificial sequence
<220> FEATURE:
<223> OTHER INFORMATION: Synthetic Primer

<400> SEQUENCE: 80
cgacgatatg aatcagggaa tagg                                                24
```

<210> SEQ ID NO 81
<211> LENGTH: 23
<212> TYPE: DNA
<213> ORGANISM: Artificial sequence
<220> FEATURE:
<223> OTHER INFORMATION: Synthetic Primer

<400> SEQUENCE: 81
tggcatcctc ttatcaacaa agc                                             23

<210> SEQ ID NO 82
<211> LENGTH: 22
<212> TYPE: DNA
<213> ORGANISM: Artificial sequence
<220> FEATURE:
<223> OTHER INFORMATION: Synthetic Primer

<400> SEQUENCE: 82
cctatcagtg ttggtggaag ca                                              22

<210> SEQ ID NO 83
<211> LENGTH: 25
<212> TYPE: DNA
<213> ORGANISM: Artificial sequence
<220> FEATURE:
<223> OTHER INFORMATION: Synthetic Primer

<400> SEQUENCE: 83
gagaaggatg cttttgaaga gctta                                           25

<210> SEQ ID NO 84
<211> LENGTH: 24
<212> TYPE: DNA
<213> ORGANISM: Artificial sequence
<220> FEATURE:
<223> OTHER INFORMATION: Synthetic Primer

<400> SEQUENCE: 84
acctgactcg gtttctcatt caat                                            24

<210> SEQ ID NO 85
<211> LENGTH: 30
<212> TYPE: DNA
<213> ORGANISM: Artificial sequence
<220> FEATURE:
<223> OTHER INFORMATION: Synthetic Primer

<400> SEQUENCE: 85
ggtaaacatt gtcttaccat tattgacatt                                      30

<210> SEQ ID NO 86
<211> LENGTH: 30
<212> TYPE: DNA
<213> ORGANISM: Artificial sequence
<220> FEATURE:
<223> OTHER INFORMATION: Synthetic Primer

<400> SEQUENCE: 86
catcaacttg cattacataa agtctgatta                                      30

<210> SEQ ID NO 87
<211> LENGTH: 32
<212> TYPE: DNA
<213> ORGANISM: Artificial sequence
<220> FEATURE:

<223> OTHER INFORMATION: Synthetic Primer

<400> SEQUENCE: 87
ttatgtttgt aatctaatca ggctatgttt tt                                    32

<210> SEQ ID NO 88
<211> LENGTH: 28
<212> TYPE: DNA
<213> ORGANISM: Artificial sequence
<220> FEATURE:
<223> OTHER INFORMATION: Synthetic Primer

<400> SEQUENCE: 88
aaaaggaaga aagaagaac aaattttg                                          28

<210> SEQ ID NO 89
<211> LENGTH: 26
<212> TYPE: DNA
<213> ORGANISM: Artificial sequence
<220> FEATURE:
<223> OTHER INFORMATION: Synthetic Primer

<400> SEQUENCE: 89
agcagaatcc tcacttcaaa gtacag                                           26

<210> SEQ ID NO 90
<211> LENGTH: 25
<212> TYPE: DNA
<213> ORGANISM: Artificial sequence
<220> FEATURE:
<223> OTHER INFORMATION: Synthetic Primer

<400> SEQUENCE: 90
accaagagga gaaatctgc ttagg                                             25

<210> SEQ ID NO 91
<211> LENGTH: 21
<212> TYPE: DNA
<213> ORGANISM: Artificial sequence
<220> FEATURE:
<223> OTHER INFORMATION: Synthetic Primer

<400> SEQUENCE: 91
ccaacaaggg tgcagaaatg a                                                21

<210> SEQ ID NO 92
<211> LENGTH: 24
<212> TYPE: DNA
<213> ORGANISM: Artificial sequence
<220> FEATURE:
<223> OTHER INFORMATION: Synthetic Primer

<400> SEQUENCE: 92
gggttgcctt gatagttgaa tctg                                             24

<210> SEQ ID NO 93
<211> LENGTH: 26
<212> TYPE: DNA
<213> ORGANISM: Artificial sequence
<220> FEATURE:
<223> OTHER INFORMATION: Synthetic Primer

<400> SEQUENCE: 93
cacttcatct tcaggcatat actcca                                           26

```
<210> SEQ ID NO 94
<211> LENGTH: 21
<212> TYPE: DNA
<213> ORGANISM: Artificial sequence
<220> FEATURE:
<223> OTHER INFORMATION: Synthetic Primer

<400> SEQUENCE: 94
tcttcaaggc tggttggatg a                                              21

<210> SEQ ID NO 95
<211> LENGTH: 24
<212> TYPE: DNA
<213> ORGANISM: Artificial sequence
<220> FEATURE:
<223> OTHER INFORMATION: Synthetic Primer

<400> SEQUENCE: 95
tgatggtgaa tatgaagggt ctca                                           24

<210> SEQ ID NO 96
<211> LENGTH: 27
<212> TYPE: DNA
<213> ORGANISM: Artificial sequence
<220> FEATURE:
<223> OTHER INFORMATION: Synthetic Primer

<400> SEQUENCE: 96
aatggaactg ggatttctta ctacaaa                                        27

<210> SEQ ID NO 97
<211> LENGTH: 23
<212> TYPE: DNA
<213> ORGANISM: Artificial sequence
<220> FEATURE:
<223> OTHER INFORMATION: Synthetic Primer

<400> SEQUENCE: 97
tggcaaaagc tagagagcat gat                                            23

<210> SEQ ID NO 98
<211> LENGTH: 25
<212> TYPE: DNA
<213> ORGANISM: Artificial sequence
<220> FEATURE:
<223> OTHER INFORMATION: Synthetic Primer

<400> SEQUENCE: 98
aaccctaacc ttttcttctg ctctt                                          25

<210> SEQ ID NO 99
<211> LENGTH: 28
<212> TYPE: DNA
<213> ORGANISM: Artificial sequence
<220> FEATURE:
<223> OTHER INFORMATION: Synthetic Primer

<400> SEQUENCE: 99
aactgaaaat tttacattcc tgtcaatg                                       28

<210> SEQ ID NO 100
<211> LENGTH: 33
<212> TYPE: DNA
<213> ORGANISM: Artificial sequence
<220> FEATURE:
<223> OTHER INFORMATION: Synthetic Primer
```

```
<400> SEQUENCE: 100
ttctaactga tgacttcaca ctagttttct tat                            33

<210> SEQ ID NO 101
<211> LENGTH: 26
<212> TYPE: DNA
<213> ORGANISM: Artificial sequence
<220> FEATURE:
<223> OTHER INFORMATION: Synthetic Primer

<400> SEQUENCE: 101
ctcatgtcat catcttacac aaagca                                    26

<210> SEQ ID NO 102
<211> LENGTH: 28
<212> TYPE: DNA
<213> ORGANISM: Artificial sequence
<220> FEATURE:
<223> OTHER INFORMATION: Synthetic Primer

<400> SEQUENCE: 102
cttgtggaga ataagaaaaa ggttcttc                                  28

<210> SEQ ID NO 103
<211> LENGTH: 31
<212> TYPE: DNA
<213> ORGANISM: Artificial sequence
<220> FEATURE:
<223> OTHER INFORMATION: Synthetic Primer

<400> SEQUENCE: 103
tctatatcca aagtctttat atggacacct t                              31

<210> SEQ ID NO 104
<211> LENGTH: 28
<212> TYPE: DNA
<213> ORGANISM: Artificial sequence
<220> FEATURE:
<223> OTHER INFORMATION: Synthetic Primer

<400> SEQUENCE: 104
ttaaaatcat tacacagtca ctccacaa                                  28

<210> SEQ ID NO 105
<211> LENGTH: 28
<212> TYPE: DNA
<213> ORGANISM: Artificial sequence
<220> FEATURE:
<223> OTHER INFORMATION: Synthetic Primer

<400> SEQUENCE: 105
gtcacaaagc aattccaatt ataacact                                  28

<210> SEQ ID NO 106
<211> LENGTH: 24
<212> TYPE: DNA
<213> ORGANISM: Artificial sequence
<220> FEATURE:
<223> OTHER INFORMATION: Synthetic Primer

<400> SEQUENCE: 106
aaccttggta aggcaaaaat gcta                                      24

<210> SEQ ID NO 107
<211> LENGTH: 24
```

```
<212> TYPE: DNA
<213> ORGANISM: Artificial sequence
<220> FEATURE:
<223> OTHER INFORMATION: Synthetic Primer

<400> SEQUENCE: 107
gggtgctgat tttcataaag ttga                                               24

<210> SEQ ID NO 108
<211> LENGTH: 24
<212> TYPE: DNA
<213> ORGANISM: Artificial sequence
<220> FEATURE:
<223> OTHER INFORMATION: Synthetic Primer

<400> SEQUENCE: 108
gccattctaa ttttgtgga caga                                                24

<210> SEQ ID NO 109
<211> LENGTH: 22
<212> TYPE: DNA
<213> ORGANISM: Artificial sequence
<220> FEATURE:
<223> OTHER INFORMATION: Synthetic Primer

<400> SEQUENCE: 109
taacctctcc tcccccaaac tt                                                 22

<210> SEQ ID NO 110
<211> LENGTH: 24
<212> TYPE: DNA
<213> ORGANISM: Artificial sequence
<220> FEATURE:
<223> OTHER INFORMATION: Synthetic Primer

<400> SEQUENCE: 110
gggttgtcct agaactcctg aaga                                               24

<210> SEQ ID NO 111
<211> LENGTH: 27
<212> TYPE: DNA
<213> ORGANISM: Artificial sequence
<220> FEATURE:
<223> OTHER INFORMATION: Synthetic Primer

<400> SEQUENCE: 111
tgttcttgta atcatcaacc agcttaa                                            27

<210> SEQ ID NO 112
<211> LENGTH: 20
<212> TYPE: DNA
<213> ORGANISM: Artificial sequence
<220> FEATURE:
<223> OTHER INFORMATION: Synthetic Primer

<400> SEQUENCE: 112
gccttctccg ttgcatacca                                                    20

<210> SEQ ID NO 113
<211> LENGTH: 23
<212> TYPE: DNA
<213> ORGANISM: Artificial sequence
<220> FEATURE:
<223> OTHER INFORMATION: Synthetic Primer

<400> SEQUENCE: 113
```
tcacatgcat tagggaattg ctt                                             23

<210> SEQ ID NO 114
<211> LENGTH: 25
<212> TYPE: DNA
<213> ORGANISM: Artificial sequence
<220> FEATURE:
<223> OTHER INFORMATION: Synthetic Primer

<400> SEQUENCE: 114
agcattgtcc caactaagat cttgt                                           25

<210> SEQ ID NO 115
<211> LENGTH: 26
<212> TYPE: DNA
<213> ORGANISM: Artificial sequence
<220> FEATURE:
<223> OTHER INFORMATION: Synthetic Primer

<400> SEQUENCE: 115
atgtattcat tttgaatggg ctacaa                                          26

<210> SEQ ID NO 116
<211> LENGTH: 26
<212> TYPE: DNA
<213> ORGANISM: Artificial sequence
<220> FEATURE:
<223> OTHER INFORMATION: Synthetic Primer

<400> SEQUENCE: 116
gttaaaaatt acaacgccac gaataa                                          26

<210> SEQ ID NO 117
<211> LENGTH: 29
<212> TYPE: DNA
<213> ORGANISM: Artificial sequence
<220> FEATURE:
<223> OTHER INFORMATION: Synthetic Primer

<400> SEQUENCE: 117
ttgcaatttt ttatatcttg atttcacat                                       29

<210> SEQ ID NO 118
<211> LENGTH: 23
<212> TYPE: DNA
<213> ORGANISM: Artificial sequence
<220> FEATURE:
<223> OTHER INFORMATION: Synthetic Primer

<400> SEQUENCE: 118
gcgaagaatc aaaactggtc aaa                                             23

<210> SEQ ID NO 119
<211> LENGTH: 27
<212> TYPE: DNA
<213> ORGANISM: Artificial sequence
<220> FEATURE:
<223> OTHER INFORMATION: Synthetic Primer

<400> SEQUENCE: 119
acaaggacaa ggctatgaga agtaaga                                         27

<210> SEQ ID NO 120
<211> LENGTH: 20
<212> TYPE: DNA
<213> ORGANISM: Artificial sequence
<220> FEATURE:
<223> OTHER INFORMATION: Synthetic Primer

<400> SEQUENCE: 120
ggccatgaat caagccactt                                                    20

<210> SEQ ID NO 121
<211> LENGTH: 23
<212> TYPE: DNA
<213> ORGANISM: Artificial sequence
<220> FEATURE:
<223> OTHER INFORMATION: Synthetic Primer

<400> SEQUENCE: 121
gagttagatt tatccggcaa cga                                                23

<210> SEQ ID NO 122
<211> LENGTH: 24
<212> TYPE: DNA
<213> ORGANISM: Artificial sequence
<220> FEATURE:
<223> OTHER INFORMATION: Synthetic Primer

<400> SEQUENCE: 122
cccgaagaga tgtcatgtta acaa                                               24

<210> SEQ ID NO 123
<211> LENGTH: 22
<212> TYPE: DNA
<213> ORGANISM: Artificial sequence
<220> FEATURE:
<223> OTHER INFORMATION: Synthetic Primer

<400> SEQUENCE: 123
gcgaaaaaca aatttccatt gc                                                 22

<210> SEQ ID NO 124
<211> LENGTH: 20
<212> TYPE: DNA
<213> ORGANISM: Artificial sequence
<220> FEATURE:
<223> OTHER INFORMATION: Synthetic Primer

<400> SEQUENCE: 124
agtggtgatg gcatggttga                                                    20

<210> SEQ ID NO 125
<211> LENGTH: 25
<212> TYPE: DNA
<213> ORGANISM: Artificial sequence
<220> FEATURE:
<223> OTHER INFORMATION: Synthetic Primer

<400> SEQUENCE: 125
tcactaagat ctggaattcc aaacc                                              25

<210> SEQ ID NO 126
<211> LENGTH: 30
<212> TYPE: DNA
<213> ORGANISM: Artificial sequence
<220> FEATURE:
<223> OTHER INFORMATION: Synthetic Primer

<400> SEQUENCE: 126
tggaggaaga taagttaaca attaatagca                                         30

```
<210> SEQ ID NO 127
<211> LENGTH: 26
<212> TYPE: DNA
<213> ORGANISM: Artificial sequence
<220> FEATURE:
<223> OTHER INFORMATION: Synthetic Primer

<400> SEQUENCE: 127
cctgaaaaag ccaatcataa tctaca                                       26

<210> SEQ ID NO 128
<211> LENGTH: 23
<212> TYPE: DNA
<213> ORGANISM: Artificial sequence
<220> FEATURE:
<223> OTHER INFORMATION: Synthetic Primer

<400> SEQUENCE: 128
caggtaggga tgcttcagtg ttg                                          23

<210> SEQ ID NO 129
<211> LENGTH: 28
<212> TYPE: DNA
<213> ORGANISM: Artificial sequence
<220> FEATURE:
<223> OTHER INFORMATION: Synthetic Primer

<400> SEQUENCE: 129
tggaaaagga aagatgatat agcaattt                                     28

<210> SEQ ID NO 130
<211> LENGTH: 23
<212> TYPE: DNA
<213> ORGANISM: Artificial sequence
<220> FEATURE:
<223> OTHER INFORMATION: Synthetic Primer

<400> SEQUENCE: 130
aaccaggaca accacatcaa tct                                          23

<210> SEQ ID NO 131
<211> LENGTH: 25
<212> TYPE: DNA
<213> ORGANISM: Artificial sequence
<220> FEATURE:
<223> OTHER INFORMATION: Synthetic Primer

<400> SEQUENCE: 131
tgatcggatt tgactctttt gtcat                                        25

<210> SEQ ID NO 132
<211> LENGTH: 27
<212> TYPE: DNA
<213> ORGANISM: Artificial sequence
<220> FEATURE:
<223> OTHER INFORMATION: Synthetic Primer

<400> SEQUENCE: 132
ttgcagtttt tgagtatacc actacca                                      27

<210> SEQ ID NO 133
<211> LENGTH: 28
<212> TYPE: DNA
<213> ORGANISM: Artificial sequence
<220> FEATURE:
<223> OTHER INFORMATION: Synthetic Primer
```

```
<400> SEQUENCE: 133
atggaagtgg atggaagtag tataatga                                        28

<210> SEQ ID NO 134
<211> LENGTH: 24
<212> TYPE: DNA
<213> ORGANISM: Artificial sequence
<220> FEATURE:
<223> OTHER INFORMATION: Synthetic Primer

<400> SEQUENCE: 134
tttccacatt ttccaatagc ttga                                            24

<210> SEQ ID NO 135
<211> LENGTH: 25
<212> TYPE: DNA
<213> ORGANISM: Artificial sequence
<220> FEATURE:
<223> OTHER INFORMATION: Synthetic Primer

<400> SEQUENCE: 135
tggagctcta ccgaaagttt acaaa                                           25

<210> SEQ ID NO 136
<211> LENGTH: 24
<212> TYPE: DNA
<213> ORGANISM: Artificial sequence
<220> FEATURE:
<223> OTHER INFORMATION: Synthetic Primer

<400> SEQUENCE: 136
caagaactac ctcaaagcca atcc                                            24

<210> SEQ ID NO 137
<211> LENGTH: 25
<212> TYPE: DNA
<213> ORGANISM: Artificial sequence
<220> FEATURE:
<223> OTHER INFORMATION: Synthetic Primer

<400> SEQUENCE: 137
cttttaaatg gacccagttt gttca                                           25

<210> SEQ ID NO 138
<211> LENGTH: 23
<212> TYPE: DNA
<213> ORGANISM: Artificial sequence
<220> FEATURE:
<223> OTHER INFORMATION: Synthetic Primer

<400> SEQUENCE: 138
tgggttgaag tgaaatggtc aga                                             23

<210> SEQ ID NO 139
<211> LENGTH: 27
<212> TYPE: DNA
<213> ORGANISM: Artificial sequence
<220> FEATURE:
<223> OTHER INFORMATION: Synthetic Primer

<400> SEQUENCE: 139
agcaacaatg actatttcaa ccatttt                                         27

<210> SEQ ID NO 140
```

<211> LENGTH: 19
<212> TYPE: DNA
<213> ORGANISM: Artificial sequence
<220> FEATURE:
<223> OTHER INFORMATION: Synthetic Primer

<400> SEQUENCE: 140
ccacacctcc ccttggttt                                                    19

<210> SEQ ID NO 141
<211> LENGTH: 22
<212> TYPE: DNA
<213> ORGANISM: Artificial sequence
<220> FEATURE:
<223> OTHER INFORMATION: Synthetic Primer

<400> SEQUENCE: 141
cagcaaaatg aatgcaattg gt                                                22

<210> SEQ ID NO 142
<211> LENGTH: 23
<212> TYPE: DNA
<213> ORGANISM: Artificial sequence
<220> FEATURE:
<223> OTHER INFORMATION: Synthetic Primer

<400> SEQUENCE: 142
acattgcaag aactggatgg ttt                                               23

<210> SEQ ID NO 143
<211> LENGTH: 1040
<212> TYPE: DNA
<213> ORGANISM: Glycine max

<400> SEQUENCE: 143
agaaagagag aagagtgaag agtgttattt ttttgtttga ctctgaaaaa aaattaagat        60
acaacacatg gcatgattgg agccgtttat atgatcctac gcatgaaaat gtttcaacta      120
cacatccggt tcccgtcaag aatgggagag gatccgtatg cgatgaactg aacttgaatt      180
gattcattta atatagtgag agagaaaaaa gttaaaccaa tcaaaatggt tgattgcttt      240
agttttatat ttccttttta caaattaacc ctattgttaa cagattaatt tggttaatga      300
atattttatt tctttttttat tctctttaat ttcaatcaaa caattttatt ttttactttt      360
tttctattct gtctcattta tttttcattt ctcacgatca aacagaggat tagtctaaaa      420
aaatattaaa taatgcttga ttttattgga actaattctt aatttcatga ccggaatatt      480
cacatgaatt aattgaaaaa tgtgtaagat tggttagatt ggattaattt acttgactttt      540
cttaattgtc tttttatgaa tttgactaac ctaattcttt atttattttg cgaagaaaga      600
agtattattg tatccgtgtg tgtatatata aaataaagtc attcaatcgg tcctaaatta      660
cacaagatac atgtcaaata tgcaaatgaa gtaactcttt gatctgaaaa aaaaaaaaa       720
aaaaacaat ccagttttcc cttgtgaaaa aagagctcca aatagcttca ggttgaagca       780
aaataaaaa attgaagaaa aggttgaagc taaacataaa cctcaaaaac tggtgtacgt       840
cattaacatg ggtgacccccg aagttgccac gtactccaag cgtgtgcggt taacaacgta     900
cgagagtatc gaatctgcct ctgctttctt tcaatttcaa cagaacccat cacacacaca     960
cagaccccat caaccaaaaa caagaacaa tgattctgag atttgcagca gctgcaggtc     1020
gactctagga aagacccggg                                                 1040

<210> SEQ ID NO 144
<211> LENGTH: 821
<212> TYPE: DNA
<213> ORGANISM: Glycine max
<220> FEATURE:
<221> NAME/KEY: unsure
<222> LOCATION: (1)..(821)
<223> OTHER INFORMATION: unsure at all n locations; n = a, t, c, or g

<400> SEQUENCE: 144

| | | | | | |
|---|---|---|---|---|---|
| attccataac | ggtttgcaac | tcttgaagat | cgtgactctg | gtcgtgtcac | tcctgcgtat | 60 |
| cgcgcctggg | agcaacaaga | ttagttgttc | ctctcatggc | ttcaatccac | cgtttctgct | 120 |
| cccattcttc | gaaatttcat | cggctgcact | agtttgtggc | ttctctagga | caaaatccac | 180 |
| aactattttc | atgctcatac | aaatgcaaag | gcacggccac | ttcgtacaga | gctgcatcaa | 240 |
| ctcactcttg | aaggtcgtac | tatttctgat | tatttgactg | agattcagaa | tcttgttgat | 300 |
| tcttttactg | ctattggtga | tccaatttct | atttgcgaac | atgttgacat | tattattgaa | 360 |
| gaatgtgtac | cagaaaacta | tgagtcctct | gtttcgcaca | tcaataatag | atctgaacct | 420 |
| ctcactattg | atgaaatcaa | aactgttctt | ctcggtcatg | aggctcagat | tgacaaattc | 480 |
| aggaagaagg | cagtggtttc | ggttaatgtt | gcttccacat | ccactgtgtc | ttctgtgact | 540 |
| aatccatctc | atgctaattt | tggaggtttc | agaatcagaa | tcagagtcag | tataaaaaca | 600 |
| gaggacgtag | cagtattcag | tgttacatct | gtcagaagtt | tggtcatgat | gttgccaact | 660 |
| gctggcacag | gccctcaact | tcctatgctc | tgctccttat | cctatgttgg | cacaatttcc | 720 |
| caccatgcct | cagctttatt | ccaatttctt | tggagctgct | ctgcatttcc | ctcttatctg | 780 |
| tttatgcagg | ctcctgtntc | tcaacaatgc | cagcagccac | t | | 821 |

<210> SEQ ID NO 145
<211> LENGTH: 855
<212> TYPE: DNA
<213> ORGANISM: Glycine max

<400> SEQUENCE: 145

| | | | | | |
|---|---|---|---|---|---|
| tagaattaca | ggtctggaga | agtatctgaa | gactgtagat | tcggtgcggg | attggattct | 60 |
| gtttcatata | tactttttta | acaacataag | ttaattttc | atatagtttt | ttatttaatt | 120 |
| ttataaatat | tttgaataaa | accaaaaata | tatgtaagtc | gttcgtacat | aagacgcgtt | 180 |
| aaacgtcagt | acttaataat | aataatatag | tgtaagaaac | tcaactgggg | aagtgcataa | 240 |
| aaaaataaaa | gtataaatac | aagaaaaatg | aactaagaaa | gtgtgtactt | atgtgctaat | 300 |
| tagcaagatc | gttggaacaa | aaagccaaat | tgactggtac | tttctcgtta | atttcttcaa | 360 |
| ttttcattgt | ttcgttaaat | actagtggca | tgtccgtcaa | aagtcaaaag | ccacatattg | 420 |
| atgaaattgt | gttgttagaa | taattaatta | attacttgca | gagcaaatct | cctccacaat | 480 |
| ttttcttttt | ttctctaccc | aagagacttc | ctttcaactc | agatactctt | tgattctctt | 540 |
| caggaaaaca | tcaactaatt | aaaatctaat | tttgtctttg | atactctttg | tccgcggaat | 600 |
| tcaccacccc | caccttctca | atttgtttgc | tttctgcttt | cttacctctt | ttttctcaga | 660 |
| tttcatttgg | ttgatccttt | cttcaattct | tcttctgggt | ttgtagttgt | tttttatct | 720 |
| gacttgtgtt | tctaaaatcc | atgaaccgta | tgtgatttcc | agtgtctttt | tcttttcca | 780 |
| gattcccaga | gagaaaaaag | aaaaaatcct | tttgtttgtg | tgagactgta | aggatcaatt | 840 |
| ggttgagttc | tccta | | | | | 855 |

<210> SEQ ID NO 146

```
<211> LENGTH: 1395
<212> TYPE: DNA
<213> ORGANISM: Glycine max

<400> SEQUENCE: 146
acttgcctga gagtgttgtt gcttctgaac aggctgcatg ttcatcacat ttgaaagaaa      60
ctgttggaaa acctactctt gatgcatctc aacccagccc aactgctact cccagagata    120
ttgaggcttt tggccgatct ctaagaccaa acattgtttt gaatcataat ttctccttgt    180
tggatcaagt tcaatctgca agaaacatgg agactgatcc tagtaatcgg gatgtcaaga    240
gattgaaagt ttctgataat atggtggtgg acaaacagct ggtagattcc aaccatgggc    300
aacagttgtc atatgggtat gataatgtgg tcaaagatgg gtggtcaggt aataattcca    360
tgccatcatc agatcctaat atgctaagct tttcaacaaa gccacttgat ggacagtaca    420
caaatgcatc ttctcaagag gaggttggtt atggtaaaaa aattgctctt aatgttgctg    480
acagtaacaa agcagcctct gttaaaagtg attattctct ggtaaatcct caaatggcac    540
catcatggtt tgagcgatat ggaactttta aaaatggtaa gatgttgcca atgtacaatg    600
cacagaaaat gactgctgct aagataatgg accagccttt cattgtagca aaccaattca    660
gatagtttgc gctttcataa ttcagtagag caaattcaga gtgtcagtga tgctcagcta    720
agtaatgcta gtgaaagtcc aatgcctgct ttagctgcaa ataagcatgc agactctcag    780
ttatcgacac ctgctgttga acctgactta cttattatga gaccgaagaa gcgaaaaagt    840
gccacatctg aactcatacc atggcataaa gaactgttac agggttctga aaggcttcga    900
gatatcaggt ggttgccaaa actaagtgat ttaatgtgct tattttttcgg tgttgctatt    960 gttggtgtag taaaagatcc catgtctcca gttgatattg tgttgtttca attgttttga   1020
aagaaaacgg tgtgtttcca tagtgtcagt atgactattt taatattgtt ttatgtttat   1080
caatatatca agtatttgtt ttcctataac ttaaaatttc ttactatgtg gcagtgtggc   1140
agaattagac tgggctcaaa gtgcaagcag attgattgaa aaggtttgtt tataataaaa   1200
tcagtctacg catgaatcta taattctata atttatgagt tcactttact ctgtataatt   1260
ataattatag gttgaagaca gtgtggaggt agttgaagat ttgccagcag tggtgaagtc   1320
aaaaagaaga cttgtcttgt actactcagc ttatgcagca acaacttagt cctcctccag   1380
ctgcaggcag gcgag                                                    1395

<210> SEQ ID NO 147
<211> LENGTH: 618
<212> TYPE: DNA
<213> ORGANISM: Glycine max

<400> SEQUENCE: 147
atttcttata ctcaaatttt tggtacctct ctttccttca ataaaatttc ttcttttata     60
catgtgtgtg tgtgtgtttg gatgttggta ataaatttct gccagaggat ttgaagatga    120
agagtccata agtttgttga ttacttgata caatctaata gagtatttta accggcccat    180 ttttttttctt gggctaaagt gatgtaacat ctaacaagtg ttgaggagat aaaacatttt    240
caaggagttt gattgttgga tatctagagc aattgtaggg ttttattgta ttcatgatgc    300
ttcttaatca ttcaaattgt ttgtgccttt tcatgttata gctttgtgaa gaggagttac    360
tcaaggaaga agcgcttttta gtaaaaaaac aacttattte ctttagtttt attaatgact    420
tgtatgcaga ttggacaaca ctttagggat ggctacttgc ataaagaaga atttaagata    480
gtttatgttg ctccaatgaa ggtatgttga tgcttttgtt tttctttaca tttctctatt    540
```

| | |
|---|---|
| cagatttgct ttttgttccc tgcatttgtg tgccattact catttctaag tatagattct | 600 |
| tgtcctttcc aggctttg | 618 |

<210> SEQ ID NO 148
<211> LENGTH: 1066
<212> TYPE: DNA
<213> ORGANISM: Glycine max

<400> SEQUENCE: 148

| | |
|---|---|
| gtatgggcg attcaggagg tggaatctgc aatacaagag cttgaaggga caatgaggg | 60 |
| gaatgtaatg ttgacagaaa ctgttggacc tgaacacata gccgaggttg ttagccgttg | 120 |
| gactggtata cctgtgacaa ggcttggcca aaacgataaa gaaaggttga ttggtcttgc | 180 |
| tgacagattg caccgagag ttgtggggca agaccaagca gttaatgctg ttgctgaagc | 240 |
| tgtgctgaga tcaagagctg ggcttggaag acctcagcaa ccaactggtt ccttcttgtt | 300 |
| cttgggtcca actggtgttg gcaagactga gctttcaaag gcacttgctg agcaactctt | 360 |
| cgatgacgaa atcaattgg tgagaattga catgtctgaa tacatggaac aacactctgt | 420 |
| ttcgcggttg attggtgcac caccagggtg tgtggattga cattttcaca tttcagttta | 480 |
| ttgttagttt tctgtatgaa ctacagataa ctgactcatt gtttcgactt tcaggtatgt | 540 |
| tggacatgaa gaaggaggtc aactaactga agctataagg cggaggcctt atagtgtggt | 600 |
| actctttgat gaagtggaaa aggcacacac atctgtgttt aacactctcc ttcaagtctt | 660 |
| ggatgatggg aggttaactg atggccaagg ccgtactgtg gacttccgaa acactgtcat | 720 |
| tatcatgacc tccaaccttg gtgcagagca tctcctcact ggactttcag gaaaatcttc | 780 |
| aatgcaagta gcccgtgata gagtgatgca agaggtatgt ctcttgacac catttgttta | 840 |
| atatgtatga caaaggtctt tgtgctgtgt tttgacttgt gaccttgtct gttgaatttg | 900 |
| ttgtaacagg tgaggaggca ttttaggcca gagttgttga accggctcga tgaaattgtt | 960 |
| gtatttgatc ctctttcaca cgagcaacta aggaaggtca caaggttaca aatgaaggac | 1020 |
| gttgctagtc gtcttgctga gagaggaata gccattggca gtgacc | 1066 |

<210> SEQ ID NO 149
<211> LENGTH: 1052
<212> TYPE: DNA
<213> ORGANISM: Glycine max

<400> SEQUENCE: 149

| | |
|---|---|
| aagttcactc ttaactaatg ttttttcact gtattcccta gctatatttc agactggtgt | 60 |
| gtgacagtct ttttttgttc atagatattg cggaagcttg aagaacgtgg ggctgaccta | 120 |
| gaccgcttgt atgagatgga ggaaaaagac attgggcat taattcgtta tgcgcctgga | 180 |
| ggaagggtat gcaactttta ctagaatgat tttcgaagat ttccatcaga ggttggttcg | 240 |
| gatgttgaag aaatgctgat taatgttttc ttatcccttc ccttttttag ttggtcaagc | 300 |
| aacacctagg gtattttcca tcacttcagt tatcagcaac tgtgagtcca attaccagaa | 360 |
| ctgtgttgaa ggtatttcat gatgaagatt tttttttcca gactgctcag ttgacatttt | 420 |
| ttcattgatt tcatcacatc aaaaagccct gataccaat tctgcatcac cactcattat | 480 |
| tttcaggttg atctggtcat tacgcctgtt tcatttgga aagatcgttt tcatggtact | 540 |
| gctcaacgtt ggtggatttt ggtagaggtg aataaatttt catgtgatga ttggtcacat | 600 |
| tgtaaattcc ttggttttg ttaaaaactc tgatctcttg ttataaaagg agaaatttat | 660 |

```
caagatgaag agaaagactt tcaaagagaa aggaggatga ggaatcctcc taaacaaagg    720
aacaaaacag aaaacaacta ggaagaaaga gataatcaga gaaacaaatc ttcccagttg    780
ctcgatataa ctttcagtga aaatgctaaa gaaaccccct ttaaagcaaa tagatactga    840
gcacctgatc ttataccaaa tcatgtgacg tgctaaagaa acctccttta aaaatactag    900
aacagcttgt agcatatgta gcagatttat acaaaaaatt agcttcttta cttctgtcaa    960
aaccttgaaa accaatcatc gataattgtt tttgagactt aggacacacc caacattaac   1020
tgaaaatgct gaataagtaa tgccagggag gg                                 1052

<210> SEQ ID NO 150
<211> LENGTH: 742
<212> TYPE: DNA
<213> ORGANISM: Glycine max

<400> SEQUENCE: 150
tgaaccaggg tattgtgagc attcatgcta tagatgtgta gtttgctgga atcaaattcc     60
tcgagttatt ggtatgagat attttatgat taagaaattt gaagggtttt agcttattgc    120
tttggatgtt aaatataccg ttttttagttt tcaatgatg aaaataagat aattgatgat    180
taataggttt tactttttgg agcatagttt atatttcta tattagtgca tagtacttag    240
tagcctacca caacaatatg aggcttcaaa tatggtgatt tgcctgatcc cacaatgaaa    300
tagaatgtaa cttttatt tttttaaaac atagctatag aaagtaactt tttttatg       360 aagtatgaac aaaccattgg ttaacaatgc atatattatt atcaactaaa agtgcacaaa    420
tttgtacggg aagtcagtgt cagccatgct tttgaggtaa tgtaactact gagcccaaat    480
gcaaattttg aggtaatgta cagtacacgc cattatagta caatgttaaa tttgctaata    540
ctgtatttaa ttgcatacat atgtaaaagt atgtcgatga atctttttgt accacttgta    600
ccatccgcgc cttgtattg ttgaccactc attgatgatt tacctgcatt tttaattatt    660
aggtgttttc agacctaaat aatttgttct tttctttgta ggttggatta taatcctata    720
gtcaaggtgt cttgtatccc tt                                            742

<210> SEQ ID NO 151
<211> LENGTH: 681
<212> TYPE: DNA
<213> ORGANISM: Glycine max

<400> SEQUENCE: 151
agaaaacttc tctccgttca tcttcttttct actcaatggc atcctcttat caacaaagcc     60
cttccatgaa gcaacaagat gcttccacca acactgatag gagcacccaa atcccagcat    120
ctacagtgac gactgttacg aacagaggac aaagctagct atgctaaact acactaatgg    180
ttaccttcgt aattcttcct tccttcttat ttcattactg ccatatttat aatgatttca    240 acaaagata atatatggca ttccaaatgg ccataacaga aaggaaaata tcctaataac    300
agagtgagat gaagtttgtt ataacagaaa ggtattttgg ggcaataaca gaattagtgg    360
agtgagtggt ggaatatcct gaagttggtg cccatgctgt ttatcctaca cttgagtcat    420
agcagcgttg ctatcaacga cgcagagaga aaggggcttt gaattaatac ttattcctgg    480
tcatgaagag gaacgcaaaa agtatgcgaa acacaggtac taattccagc ttctcttaac    540
aataaaaaca tatgttttga atgtccttat tgtccacagg tggatttaga gtccattaaa    600
agttggttcc caacacatga tgggagaaca ccctataatt cataaagata ctaccattag    660
ggagtgattt ttgaaagaaa a                                              681
```

<210> SEQ ID NO 152
<211> LENGTH: 993
<212> TYPE: DNA
<213> ORGANISM: Glycine max

<400> SEQUENCE: 152

| | | | | | |
|---|---|---|---|---|---|
| atcattttca | aagagtgtat | attttttttt | tttaaatcgc | tgagttccta | aatataatcc | 60 |
| aaacactgaa | ttgaggagtc | aagtgctgtg | tgtgtaagac | attgcaaaat | aagttaccac | 120 |
| aaattcaccg | aagtttcata | gatattgtct | tattgttatt | tgatcctgaa | acatgctagc | 180 |
| aggattaata | aaaagaataa | aaatgttacc | agctgcacta | gtatagtttt | gatcctgtca | 240 |
| tcctttctag | caatggttcc | attccttgaa | tacacttcat | ctgaatgacc | aattttattc | 300 |
| ttggcacctt | cattcttttc | aatggaatca | atgttggtgg | agctcacacc | actgaaatac | 360 |
| acttcacccg | aatgaccaat | tttattcttg | gaaccttcat | tcttttcaat | ggaatcaatg | 420 |
| ttggtggagc | tcacaacact | tgaatacact | tcacccaaat | gaccaatttt | attcttggca | 480 |
| ccttcatttt | tttcaatgca | atcaatgttg | atagagctca | caacacttga | agtcagctcc | 540 |
| atgatctgct | cagactttgt | tcctttgtca | tcaattgcat | cctcagtagt | tgtctctggc | 600 |
| atatcttcat | aagtagagag | tttgacagaa | tcgctgaaag | aaactctttt | aattttggc | 660 |
| gttattgggc | tttctaactt | agaaacatct | gattcaacca | ttgacataga | aaatctttgt | 720 |
| atcggaccag | gttggataaa | aaaatttcta | cccctttgacc | aaattttgtt | agagtagtct | 780 |
| ttggttgtcc | tccatctctt | cagtttcgtg | ctgccactgc | tactttggct | actggaagag | 840 |
| ccttaaagg | tattaagttt | caattcatcc | gtttcgctcg | atgtggaatt | tggagagacc | 900 |
| ctctcaagct | ccagaacaga | atttggagcc | tgccttttc | ccccaagatc | cttgggtgga | 960 |
| tgttgccccc | aaagctatct | cttactgaag | gaa | | | 993 |

<210> SEQ ID NO 153
<211> LENGTH: 435
<212> TYPE: DNA
<213> ORGANISM: Glycine max

<400> SEQUENCE: 153

| | | | | | |
|---|---|---|---|---|---|
| aggcatcgga | agatgagaag | actgatgccc | caaaagcaat | tgagagtaca | ccccagtcga | 60 |
| caccccagtc | tacttctgga | attgaggatt | tatttaaaga | ctcaccttta | gttacaccaa | 120 |
| gtttaactcc | agaaaaacca | caaaagatc | taaaaaatga | tatcatgagc | ctctttgaga | 180 |
| aggtatgtgc | cagtgcttca | ataggtttgt | ttaaggctga | gttacttctt | tgagtttata | 240 |
| tatatatata | tggttagaaa | tgcttttaa | aatatacaca | ttctatattg | ttgacatttc | 300 |
| ctccttgccc | gatgtgagtt | attatccaag | acaccaaaac | aagtgaattt | agttgtcgat | 360 |
| cgatctctat | ccttagatgg | gtttttatgt | tttggtatgt | gaataagatt | ttacctgacc | 420 |
| cagtaaattg | gacat | | | | | 435 |

<210> SEQ ID NO 154
<211> LENGTH: 362
<212> TYPE: DNA
<213> ORGANISM: Glycine max

<400> SEQUENCE: 154

| | | | | | |
|---|---|---|---|---|---|
| aatacaatta | ttcaatgaca | atatgctcta | tttataaaag | aaattgagcc | actacactag | 60 |
| ccactaactc | ctaggtgcct | aggaaaacaa | tatccagcaa | taacataatt | tattcaaata | 120 |

```
ccccacatca cctaataaca atatcaataa cagaaactta aaaccaatta aatgacccac      180
gtcacctaac attccttccc gtaaactgaa tgatcaatat tcagttttaaa caacataagc     240 agtagaatat tatctctgaa actaattatt caaaactgcc cacaccaagc aattttttgta    300 gcttctgaaa tacaggtgct ttgagaggtt tagtaagtat atcagcaact tgatctttac    360
tt                                                                     362
```

<210> SEQ ID NO 155
<211> LENGTH: 652
<212> TYPE: DNA
<213> ORGANISM: Glycine max

<400> SEQUENCE: 155

```
attgtgattt tcactggttt gtgagagtgc aaaagaattg ttcagttgaa tgtgcaaaat      60
tgcttggatc agttgaaatg cacctatgaa tttgtatttt tctttttttat gacaaagggc    120 atgtagaata tgattatatt tgtttgaat agtgtggggg agcattactg tttttttttt      180
tttggaaaaa aaaatctgat gtggtagtgg tgtctgattc acatgtggaa aattcttatg    240
gattgggaaa gaatattgat tgtttcctttt tctcacagtg ctggtggtga aagcagtgga    300
ttccttgcat tcagagttca gggctgtgga taatttggtt gtgtgcaata ccaaccgtgt    360
ccttaaagct ttccagaatg ctcgagttgg atcccatgta agcattcccc ttgatttata    420
taacctttat gcaaatgtac atttaatatg atgctcaatg ctcaagggtt caaggctaat    480
aaacttgtta actgttttga ttgtaattgg tagagatgtc ctttaagcca ttgggctgat    540
cttgatgcct ttatgtattt tgacattttt accaaaaaca taactaatat aggaacccaa    600
aaacttagga ttcgattagg gagaacctaa ggctgcccat taaaacttga gc             652
```

<210> SEQ ID NO 156
<211> LENGTH: 1180
<212> TYPE: DNA
<213> ORGANISM: Glycine max

<400> SEQUENCE: 156

```
aaaataaaat cggagtggct aaccccagaa ttatggttgc cagtttgagt ggctttggta     60
gcctggctgg ggttagtgtt gcttcaaaaa aaccatctgg atatttcaac caaaatttag    120
tagcatgaca caaaagatgc tctaacaaag gcaaaagtga ggtagtgata gttacatgca    180
aatgccggag aaactaacca aacaagagcc aagtaagaag agccaatttt aaaatagttt    240
cccaaaatga gaagtataag ccattgaaag gatccagctt tatagagcca tctttcagcc    300
tccattttga caacagctgc tttaataatg ggggtcaact gccttccctt tgatagtgta    360
ttcgaaagat atttttgaag tagaagaaaa ccaaaatgtt gaccagtcaa tgctccgaga    420
aaagctggtg caccaaataa tccaaccacc aacattgggc ttgaaacata tggtactgga    480
gatgaagata tcaaaggtag gagaaatgaa acaggaagg agaaacttaa ggcaaagacc     540
cacatgagga gaacactcaa acacgacaag gccaatgaag ctgcagtgac tcaaggacaa    600
aaacattatg ttaggtgctt gacaaacact tcaatgcagt tcaactaatc ataatataat    660
atcaataatc aatgaagagg ggttatatct ttttctcaat aactcaatcc atcaatatat    720
aatgatcttt ctaaaccact gttcatcaac tcccatatca tcagcgcgtc accaaatcat    780
atgataagaa aaggttttac tgctgtcaac cattcatatg ataagaaaag gttttactg    840 ctgccaacca tactgttggt tgcggttacc acccatcatg tttgatccac gcccagctgc    900
cgatccacca taaggagcac cttgaggata atttggagct ccaactccat agccgcttcc    960
```

| | | | |
|---|---|---|---|
| accccccacca cgaggaccac cactgggccc accgggcata ccacttgacc cataaggtgc | | | 1020 |
| accccgccct tgaggaggat atggcccact tccataacca cttcctcctc cttgacctgc | | | 1080 |
| acgattcggg tgattgtatc ccccaccaga gttcccacca gaaggatatc ttcctggccc | | | 1140 |
| accagaagga cctcgaggct ttccataatg atggctaggt | | | 1180 |

<210> SEQ ID NO 157
<211> LENGTH: 628
<212> TYPE: DNA
<213> ORGANISM: Glycine max

<400> SEQUENCE: 157

| | | | |
|---|---|---|---|
| atgcctgcag ttaaccacac attaaagacc acgggagttt cgatggttgt atttgtatat | | | 60 |
| acgggtggga attttctga ttgtcttaat ttaagattaa atacaaaaa tacaaatgct | | | 120 |
| gaattctctt gaaaaaaaaa tacaaatact gaattgtagc aaatcaaact ttttttttcta | | | 180 |
| cataaaaaaa aacattttttt ttcctaaaaa tgccttttgt ggttgaagat ggttaacaac | | | 240 |
| cattttattt tcagttatgt attcaaatag taaatagtaa tattcattta acctaatatt | | | 300 |
| attcatataa tcaaaacttt acacaagata ctagattaaa atctagtgtg atcattgtac | | | 360 |
| ataaaaagaa taatcgaagc attacactat tttctgtcaa aaagaaaac aattgaaccg | | | 420 |
| tttcgagcaa atcaaatcat caacatcata tcaagtttat aatcaaagta gatcttttct | | | 480 |
| cgtatcatgt gattttttta tgtgtaaaaa tatgtcaaat taagacaatt ttttttaaga | | | 540 |
| ccctaaatca ataaaaaaaa ttatcgaatc gtgttgggtc aaatttatt attaggaaaa | | | 600 |
| aattcaattt aacttaaatt acccaaat | | | 628 |

<210> SEQ ID NO 158
<211> LENGTH: 774
<212> TYPE: DNA
<213> ORGANISM: Glycine max

<400> SEQUENCE: 158

| | | | |
|---|---|---|---|
| ggaaaaactt tgagacaaaa actaaaacac ttatgaaatt agacaaaaga atgcaatatt | | | 60 |
| aacagaatgc tacaacattt caagaggacc caaacgtaga ttataaggag aataatgaat | | | 120 |
| cctcctattt aaaacagaaa gaaactccta tcctatctaa aacagaaaga acccaatgag | | | 180 |
| ccaaagtggc tcaaaatgc aataaagtat tccaatattt tcgcatacaa atgattgatt | | | 240 |
| ctttgaagca gccattaacc aagaaccatc atagagacaa tcctatccta tgacgactgt | | | 300 |
| aaagggaaag aggtgctctt gaaaatacac gcatttcatt acaaccaaat gcactactag | | | 360 |
| ataactacat atactgcaca atgcgataaa atttaacact cttgttcct ttcaaaacct | | | 420 |
| ttaaggcatg taaagagaaa agctccaacc tatgattgga gaaactcatt gttggctagg | | | 480 |
| aaccccaaaa caattcagca ggtgtaccac aaaagtggcc tacctatagt attatcagct | | | 540 |
| tattttagca tgtttatacc tagatgtctc tattctttta tgaacttcaa tagttcaact | | | 600 |
| accatttgat gaatgtgtcc atgatcatat cataacttat atcacgcaaa cttcagaggt | | | 660 |
| tattatcttt tttgtttctc attgtattct acaccaatga ggtaaaacaa gcgagcccca | | | 720 |
| aacgcatgat gaaacataat catccattgt tgctacttgt cagatcacct cttg | | | 774 |

<210> SEQ ID NO 159
<211> LENGTH: 637
<212> TYPE: DNA
<213> ORGANISM: Glycine max

<400> SEQUENCE: 159

```
acaaagtgct tgcttgaact ttatggacta aaggtaaaat ttattctgga atcttcaatt      60
cttagtgagc tatgtctaac ttcaatgctt atattgcaag cctcgtctaa ctttcacaaa     120
ttgattgcta aattgtttac agtataagta tgacaaaatt gctttctgtt tatgagatac     180
gtcccccccc ccccccccct actcattatt ataatgaagg gaacagctga aaataattta     240
tagtaaggaa attagttgat tttttttttt acatttgttt gttgtcgact gcaaccgaga     300
aatgacaata attgtgtcct tgttggcaag gacttcttt ctggcagctg gcagagttgc      360
agatgaaggt tcggtctgat gtgagttctg aatactggct caatgctaag tgtgcatatc     420
ctgacaggca attgtttgat tggggcatga tgaggttgcg ccgtccattg tatggtgttg     480
gagatccatt tgccatggat gctgatgatc aattaaagaa gaaacgggag ctgaggtaa      540
cttctttt ttcttcagta atatgtattc cccctctccc cttttgtggg tttgaacttg       600
gtttccatat catggatatc atagactata gttacat                              637
```

<210> SEQ ID NO 160
<211> LENGTH: 1040
<212> TYPE: DNA
<213> ORGANISM: Glycine max
<220> FEATURE:
<221> NAME/KEY: unsure
<222> LOCATION: (1)..(1040)
<223> OTHER INFORMATION: unsure at all n locations; n = a, t, c, or g

<400> SEQUENCE: 160

```
aacctccatc accatctggc tctttctcat agtgtagatt tgctgtagca aaagccacat      60
cctcaatcct ctttgcattc tcttcagcct tttcctggtc caaagttcca tacttctgtg     120
tgaaaatcga tttagtagtc agattgttgg tcatcctctc cacaagggtc tgcctagtgt     180
tctgactagg aggccataat ttgattgaaa atggtctcgg ctgtgaattc agctccatgg     240
caatgaaacc tacaagaact gcaagtgcaa gtatataaat ggaatatttt aggatacata     300
acaagagtaa aaaatagttc aagcagactt gttagagaaa acaattgtaa ggcaatgtca     360
ttcatagatg catgtcctca atatggtatc agcccttgtc agacagaata aaacatttta     420
caagccctta acacaaattt gagttttgaa tggataaaaa aaaatgtttt acaaaacagg     480
ttagttaata ggagcagaag taaagaaat cccatccaag aaataattgc tataacatat      540
aaacatatat atacacccag gcccnnnnnc ncaanncanc acacacacac acacacacac     600
acacatatat atatatacac acacacgtaa agtggattgc aataataaag tagggggcatg    660
ttcctttcca tttcaatcat atcatgttaa tgaaactaat aaaaacttca aagcatgatg     720
aaaaaatgaa aagggttagg gagtttataa aggaaacttt gcaaaacata ccatgaatgt     780
acgtacgagg ttgtttcctc tgaagagaag agaacactca caaaccgtc gacagtaata      840
aataaccgac aatcaactta gtttggttca cccacaaatc aaacccatcc taataaaaat     900
cttagcttta agctcgaatg caacagatcc gagactgcgc aaagatacaa actttaaaca     960
cgaatttgaa aatctttgga gaaaggggaa ggaactggga acagggtaga ctgaaataaa    1020
gagagacaag tttgacaacc                                                1040
```

<210> SEQ ID NO 161
<211> LENGTH: 845
<212> TYPE: DNA
<213> ORGANISM: Glycine max

<400> SEQUENCE: 161

```
tgcatgcctg cagcttgctg ccaaactttg ctacatttgg tatgattcag acagaagaga    60
atcatgttag cttctgtact atgtagaatt gtatggttat tagtgggttt tgtcaagagt   120
taacagtgaa ctgcaaaatg gagtgtttag agggatgcat tgtatataat atttacgtaa   180
caagtgtggc ttcccagttt tcagccatca tgatatcagc ttaagtgaca taggcgcaaa   240
acaatactga tttcatgcta atgatcagat tttcctcgtg cagtggacaa tgctaaaaag   300
actgatccca aagctcaggc cttgaagact gctatggctg tgattgtgaa atcaggatgc   360
caagtgttta agaaaaaaac taaatggacc aggacattac tgtgacatcg attacatttg   420
gcaggccaaa gacattgctg taaatttgaa actgtttggg atattgctgt aaattttgga   480
ctgatattga acgtttgatt ctgaaactgt tttggacaga tattgctgta aatttcggcc   540
tttgaggaaa aatgttttgt tgctgcaact gttttttgat tctgaaatat tgttgatatt   600
gctgtaaatt cttaaactgt gttgtggctt gtttacgttg tgtattgatc aggtttgaga   660
aaaaaacata tgaatcaaa gaaatttgtc aatacatgcc aaaaacattt gcgaatgcag   720
taagtctggg taaatcatgg tttcataacc accacgttag taactgtgta aatggcaggg   780
actagaacac actaaatttg ttttgtacaa ggattaaaaa cttacaaggg gtcaaaaatt   840
ctaaa                                                               845

<210> SEQ ID NO 162
<211> LENGTH: 631
<212> TYPE: DNA
<213> ORGANISM: Glycine max

<400> SEQUENCE: 162
ttgcctgcag ttctgcacat tgtaagcttc tggattagaa ctgtttgttg gaagtgatag    60
ttgtttatta agggtaatga gagttcgaga tgttagtgtt attgttgttg ttaaaatgag   120
ttttttataa cttaaaatga gtcttaaaat gaattttttgc ataagttaaa aatcttttaa   180
aaatctatga gagttttttat aaattatttt atttagctta tcttcattta attttttttc   240
tcttaaaagt gttttagaat aaaattcattc aaataagtaa ttattattgt tgtcgatatt   300
gttattgtta ttatcatatt ttgttttttt tttgggaag ttgaatatca taaactgatt   360
taaaaagaga ggccttggtt gtaaaaaacc ataaacttac gtcataggtg tgcgaatatg   420
ataactaaaa aactttcgag gagtgacttt tgacggtgaa attgggaaag aaaacaacat   480
actagagaaa ttcatcaaca tactttatct tatttataat ttcactttgt tacaatacat   540
tggggttttt ttataatttt taatttttt ttatcgaatc tttcaatttt atgtgcccttt   600 tactgtttac cataaaaat atccccctac t                                    631

<210> SEQ ID NO 163
<211> LENGTH: 439
<212> TYPE: DNA
<213> ORGANISM: Glycine max

<400> SEQUENCE: 163
aaccaaactc cttttgtgt tttacttagg cagccaaatg cttgggatat cttagattga    60
aaagaagagg aatttgtaac ataattacag tcaacaaaaa taccaatggg tgctatctaa   120
tcactaggta aaaaaattta gaaaaaaaaa ctgataaaaa cagcaagggg acacaattca   180
attgaaatat ggaaactgta acacattatt taagttcata cttaattagc aagtttgaca   240
aattgaatat ggagagctag catagaaatg atatcattca ttaaaataga aataaataaa   300
```

| | |
|---|---|
| taaatagcaa ggacaagttg atcttaaatt tttaaacagt acaacaataa gcactaagta | 360 |
| gaccaagaca ccatgatagc gataatatca ccagttcaga attagagtat cagtcattga | 420 |
| atatgaaaaa tgaatgtca | 439 |

<210> SEQ ID NO 164
<211> LENGTH: 543
<212> TYPE: DNA
<213> ORGANISM: Glycine max

<400> SEQUENCE: 164

| | |
|---|---|
| acgaagaggc aaagaagaaa gctcgacttg ctaggtttgc acctgcttcc aaagttgatc | 60 |
| ctcaagaaga agataagagg aaagcaaggg cacttaggtg ggttcatcat tcctctcata | 120 |
| atttgtttct cccaattcat attgtttaca agaatcaagc atgcatggtg tcttattagt | 180 |
| tattaggtct ttctgttttg ggttcccagg tttgcgaatc cgtcgtcaac ttctatagct | 240 |
| aatgttaatg gcgaggcaaa gattgagccg gtaagaccct tttggtcact ttcaatgctt | 300 |
| tgcgtcatac aaagatgaaa aaaaaatgta tttttgtgtt gactgttgtt ctgttgtgtt | 360 |
| tcaaactaga aggctgctat tgcaggcaat gctggaggag ggacctgaat gacaggtcgc | 420 |
| gtctttaatt tgtaggaatt tttcttgtaa gtcaattatc ttttgctctt gcttattacc | 480 |
| ctttgctttg catattgcat atctgatttg tgatgttatt ctcttttttt ccctcaact | 540 |
| ttt | 543 |

<210> SEQ ID NO 165
<211> LENGTH: 369
<212> TYPE: DNA
<213> ORGANISM: Glycine max

<400> SEQUENCE: 165

| | |
|---|---|
| ggcttattga cttgatcagc tgaaagatga actttgcaag gagaatttac agcttgcagg | 60 |
| tatttaattt cttttattta atggtcggcc tataattaaa ttgtagtaga gcttctcaaa | 120 |
| ctattgcctt tactacagag gaaaatcttc aaaaggaacc tcgtatcatg gaacttagga | 180 |
| atcaagtaag aatacaatcc tatgattagt atgctttttt cttttcaatt tattgctgac | 240 |
| tactgacttt ttcttcttcc tcccatggaa acagtgtaga ataattcgga caactgagtt | 300 |
| agctgctgct aaggagaaac taaatgagct tgagaagcag aaagaagaca tgttgaaatt | 360 |
| gaattccgc | 369 |

<210> SEQ ID NO 166
<211> LENGTH: 821
<212> TYPE: DNA
<213> ORGANISM: Glycine max
<220> FEATURE:
<221> NAME/KEY: unsure
<222> LOCATION: (1)..(821)
<223> OTHER INFORMATION: unsure at all n locations; n = a, t, c, or g

<400> SEQUENCE: 166

| | |
|---|---|
| acatgaaacg catttaaccg agtatgttac cagtattcat tcattctgtc cttatacgac | 60 |
| tgctgcgaa tcctttgttc ctttataaaa tgaatcgtca tttaattgaa atattggggc | 120 |
| ctaatgctaa attttaggg ttttataatc cacattcttc gggttcgggc aagaagagag | 180 |
| agaagacgca attttgaccc tcaatttcac agacctttaa tcattcacgc gattcttctt | 240 |
| ggtaactccg ccttcctcaa tccataatct gcttttataa tttatttatt tagttttat | 300 |
| tttgattttg gcttgctgca agctaattta cgctcttcag ttcaatattc cccgttcatt | 360 |

```
tgttgcagaa atctggtttt ggggcaatct ccgtatttcg atattctggg tatgtatcaa    420
aactgcacct ttttcccttg tatattgttt tgaaatgctt cttagttttta atgactatac    480 tgagctttta cttcagtttt ttctgttttt ctgcacgcct tttatgttat ttttcacctt    540
tgaggtctct ttgaaattta tgtttatgtc gatttgtgca atgattattg gcaaaaaatc    600
aaaaacaaaa atgacttcaa ttcctcatgt ttcagcctgt gcttattaga gagagtagga    660
aaggtgaaga ggggctgaaa atggaatgca tggaatgaat tttcattgag atggagtatg    720
gaacanagca ttatgctttc ctcttacttg ggaggaatga acattatttt tgggaaactc    780
atattagaat aacctgcccc taatttacac ttttttggga g                        821
```

<210> SEQ ID NO 167
<211> LENGTH: 848
<212> TYPE: DNA
<213> ORGANISM: Glycine max

<400> SEQUENCE: 167

```
gttgtgatat tttcttcact ttttcttggt tttcgatatt tagatcaaag taaatttttta    60 tactgtccat ttggtttgtg gcatctaggc atctggctct tctgctgtta atgttagtcc    120
tgtcaactgt aaagtagaaa ggagctcacc agtcaggcct tctccaattc ttgtatgaat    180
ttgtccctgc aaactctgta tgcctgatta tgatattagc atgatgacta tgatatacta    240
gtcatagctt aacaattaga aattaatatt taagtattat aactaatgct tcatttcttt    300
taatatttac acaagcatgt tggaccagct tgttatttc ctaatttctc ctggtatcct    360
taattccact atgacatacc cttgcatacc gtggaggact taacatcttt tggacatctt    420
tattatttga tgtctgtatt tctttgtgaa attatttggt ttaattaatt ttttgaagtt    480
actttatagt catgaattta tactgcatct taatacttgt tcacaactca ttgattggtt    540
atgccgtttt caacgaagaa tggagttgat cccatgggtc gaaatgtgga gaaacctaga    600
actgtggaag atgaataga taaagctaaa ccatggcagc tgtctgaaat tgtggatgct    660
gtccaatgtc ggttagttac aacgcctgac agtacagatt cttccagcaa ggttgttga    720 ttttatgaaa ttgagattgc cattttctat tgtaaactgt gtactgtgaa ctgctttaac    780
tctaaagtca tacatagggt tgttcgactt ttatatacaa actctggtgc tggtctttg    840 gcacttgg                                                              848
```

<210> SEQ ID NO 168
<211> LENGTH: 825
<212> TYPE: DNA
<213> ORGANISM: Glycine max

<400> SEQUENCE: 168

```
ttccgacttg caagaaggtt tgtcatgat gattgacgat ggaagaggca tgttacgaaa    60
tttaaatttg aatcgcaatt ttgaaaggta atgctgagca aacaaagaa ataccttat     120 ttctccattt ttccaatttt aattattttg catattcaat accttatgtt atttttctg    180 agttttctc acaaatattg actgcaagtg ttttgtagtt tggttgggaa tattttttt     240 tcattgacct agttttgttt ggtgcagaga gattggtcta atattgaatt tttttttattg    300 gtaattttgt attgttatta aactattcag agatttatt gtgtaaaatt gtatgttgtt    360
cttatcattt ggttgaagtt tacttattag tagtttctta tgttataaac tacaggttct    420
gtaaatggag gaaattacaa agaattggca gcatgaccag caaatagatc atcattggta    480
```

| | |
|---|---|
| attaatcatg ttgatgggta ctatatatga actttttgg gactcaccaa attttgtct | 540 |
| acaggtaaat tgatctatca taaaaagat ttgcaggtaa gagtctacgc atcttccgtt | 600 |
| tggtccttga gagagacatg gtttcatcct ccttgaaata tatttagacc cttaatttta | 660 |
| tgttaatttg cgtttttttg tatgctacct attttactc atttgtctcc attttactga | 720 |
| ttaactaata atttttttt cttattcaag gtacactttt attattttat gatagattag | 780 |
| acaatttaaa ctagtctaat gcctaacatt ggctgcaggt cgact | 825 |

<210> SEQ ID NO 169
<211> LENGTH: 953
<212> TYPE: DNA
<213> ORGANISM: Glycine max

<400> SEQUENCE: 169

| | |
|---|---|
| ataatgaaaa gaaagaaccc ggctggtggt tagttgcatg cacactcttc agtttaatca | 60 |
| ttttcagttt cattgtcttt gtcaaaaaat aagtttagc ttcttgagtg ttggtttgat | 120 |
| taaatttcga gcatccttaa tcctatgat tctattttt actttggcag gttcagtggg | 180 |
| gatttaggac aactgagatg tactaaaatg gataaacaat tatttggaca ctaatgaaat | 240 |
| cagtatttca acacgtgtct taggagatgg tggactagtt catacgaaga aactcttatc | 300 |
| atacaatatg gtttgaaaat ttctcttttag aaaaaaaatt gcagggactg tctgtactgc | 360 |
| taaatacata ttcttatatg ggaacaaatt ctaagaactg agtatctttt cctagacttg | 420 |
| tttctttgtt tgttatgaaa ttaatacttt cctggagctc tacaacatta ggaagttgat | 480 |
| cctcgttaat gtataataat atgattgatg aaatattttg aatgttgaag ttcaggaata | 540 |
| gaaaaacaaa atcaggaaaa tatatttaaa ttttcaatgg atttaatatt caagacaact | 600 |
| agatatttta aatttaaaat taattaaaat atagatgtaa ctttgttttc ggcctaactc | 660 |
| aaccgtaata aggcaaaaaa aattggtcgt attttggcac caaaccact tggacccgcc | 720 |
| tgattcaacc cataatctgc aacaaccgac ccgctgaaat tgacggtcaa ttctgtcata | 780 |
| aatgggccta aaaataaaaa ggatgtggat tggtatatca agagcttggg ctcggagatg | 840 |
| gaaaatattg gttacaacat gagagcctat gctatttgta gcttccaata accctgggg | 900 |
| aactgcttgg gcacccagca gttttccaaa ataacatatt agcttttttc ttt | 953 |

<210> SEQ ID NO 170
<211> LENGTH: 598
<212> TYPE: DNA
<213> ORGANISM: Glycine max

<400> SEQUENCE: 170

| | |
|---|---|
| ggacgtaatg tgaatagtta cgaacaaatt acattaagag taattacact aacttaccaa | 60 |
| acataatgtt ttgtaactat catacttaag agttttggat tcgaattatg aggtattcca | 120 |
| caagtttaga ttccttaaa tcagttgaaa ctaatttagt ttgaaattta atcttacata | 180 |
| aaaaaaatta tcctatccaa gacataatta aattatatta aaatgagtta tttatgacac | 240 |
| atagacattg gttaatgaat taaaatgac tttcttaag gaaaataat tttttttat | 300 |
| tattattata aagtaccaca aatttatttc cttcgtaatt tttaaagtat cttattgtat | 360 |
| tttttaataa aataaaatat ttattacttc cttgacatag aactctaatg gctgattagc | 420 |
| atgacccatg gttattaca cttcaagtct tatttttatt taaacataac ttccttttac | 480 |
| atacaatttc tataccatta tttattgaaa ataacaaaga taaataaatg tcctttcctt | 540 |
| aaaaagaaca agtggtgtaa taaatcctaa cgctttgttt ggctgagatg acagtcta | 598 |

<210> SEQ ID NO 171
<211> LENGTH: 724
<212> TYPE: DNA
<213> ORGANISM: Glycine max

<400> SEQUENCE: 171

| | | | | | |
|---|---|---|---|---|---|
| ttgacagctt | gctatgcctg | cagtgcttac | atatgcagtc | acaagagtgg | gaaggcaata | 60 |
| ccccctcccc | cgttttttct | atttagtgtg | gtttattct | cttgtacatt | cttcagtgta | 120 |
| ctagcctaca | acattttagt | tttgaaattt | aagttcaact | tgcaaatttt | tgtggtccgt | 180 |
| tcaaaaatta | taatgaattt | tgctgattta | tgttttattag | actggtgcaa | tttcttaatg | 240 |
| gatttctctt | gtctactgtt | tcagctatga | agcttgggtc | atttataatt | ttctgtcact | 300 |
| gtgtctggca | tgggttggtg | gtcctggagc | agttgtaata | agtttgagtg | gtcgagttct | 360 |
| gaagccatca | ttttgtctga | tgacttgttg | ctttcctcct | ataccgctgg | atgggtgggt | 420 |
| ttgtatctga | ttcatatttt | tggatgtgcc | tgaagatagt | tatgtattcc | ttgaaaacta | 480 |
| tccctgatt | tttctctatg | gaggtttttt | ttaattacct | aactttttgt | tagttgaaag | 540 |
| tactaggatg | atacatttgc | cacacaatat | ggagatttat | ttttatggat | tattggaaaa | 600 |
| cgacctagac | atcctggaga | tgcaatggat | tttagtagac | ttctaacatg | gtggcatgac | 660 |
| attatatcat | aacttatatt | cttctctcat | ttctagaact | tctatttcag | gcgtttcata | 720 |
| cgta | | | | | | 724 |

<210> SEQ ID NO 172
<211> LENGTH: 698
<212> TYPE: DNA
<213> ORGANISM: Glycine max

<400> SEQUENCE: 172

| | | | | | |
|---|---|---|---|---|---|
| ataccataaa | ggatgtcaac | ttagcagcaa | cacacactga | ccaacaggat | aatacataag | 60 |
| tttggcattg | ggcaatcaaa | aaatgaaaa | taaagctatt | aataacagca | gtgtgtggtc | 120 |
| ttatttccag | agttaataaa | aacccaatgc | atttcattaa | atgtgtcatt | gaagaaacaa | 180 |
| cttctggaac | tcctccattt | ataaatacat | caaagcagtt | acacgacatc | aaattggtct | 240 |
| ttgaaggaaa | atgaatgcca | caattatca | tcaaagcacc | aacctttgga | ggaccaatct | 300 |
| aaccttgcaa | atatctttaa | ggatcaaaat | ggatgatatt | ttatagatga | taatgaaata | 360 |
| tataacatcg | tggagatttg | atgttgtaag | ggatgagcta | gcagatgaat | tgcaatcgac | 420 |
| caaaatgaat | tcatgaaaac | attagttgga | accttcagta | gttcaaggga | aaaaatcagt | 480 |
| gacacctgtg | ctcagttaat | tgattttatt | atgcattcta | aattcatatg | cacattaaga | 540 |
| aacatagcca | cttaaccaat | gaactagcta | tcctagttcg | gaagtattta | tacttcaatg | 600 |
| gcaaccaact | ccttcacatc | acataactaa | aaaataatac | tcatgtaacc | aaaaaatagt | 660 |
| tgcaaatcag | gaataaaaaa | tgtctcaaag | gcaataac | | | 698 |

<210> SEQ ID NO 173
<211> LENGTH: 673
<212> TYPE: DNA
<213> ORGANISM: Glycine max

<400> SEQUENCE: 173

| | | | | | |
|---|---|---|---|---|---|
| agagtcgacc | tgccaggcat | atagaaaagg | aactcattca | caaccttact | cattttttgtt | 60 |
| tttttttttt | tgtcaaaaat | gaaaaggaat | ttctgtgcgc | ttataatgta | ctgtaactct | 120 |

```
aaagaaatgg tattgttgaa acgtatggag aatgggggaa aaaatagcat tcaacacttt    180 cttttgttt ggatgagaga gaaagagaaa aaaattaatt tttcttttct agacttatct    240
ttcctcccta cttttatttt cattatctct tcaacaatta agagaaattc ccaatttta    300 agatgttctt ccgtaactat tttctttctc ccgatccaaa aatagggcta agaagtacg    360 aagaagagca attcatataa aaaagcattt gatatagcaa acagaatatc ttccttgata   420
cctggtaata tgcacattag aagtagtaaa tacactctac ataccttctg acggctctgg   480
tttatatctg gcagttctat acttctgaaa tttaaaaata atgtgaaaag cattagatta   540
aataaattga catacaccca taagctattt aagaggatga taaatcacag atgtacctgc   600
aagtggcttt ttacatgata gatagtaagg ccctcaactt tcattagatt caacacaccc   660
tttggagtag cct                                                      673
```

<210> SEQ ID NO 174
<211> LENGTH: 868
<212> TYPE: DNA
<213> ORGANISM: Glycine max

<400> SEQUENCE: 174

```
aaacgctagt gttcttgcat tcttacacta cgagaacaat cctcccatac ttcaccataa    60
ccttaaatct gcctgcatct tcctagatga tgactattct gtcaagattg caggatttgg   120
tctgatcaac tccaatttt actatggttc tcacttacac aagaactatg aagcatttga   180
catctgcaaa aatgatgttt acgatatggg tgtgttgctt cttgagatta tctcaggctc   240
aaatcagttg gattcaccaa ctttggcttt acagcatgta agggctggaa aatttgaaga   300
aattttggac ccatttcttt gctatgatga acaaccacat taccgccaag agcaaatgca   360
aataattgca gatctagcta caaggtgcct gttatttggg gtagatggaa ggctaggaat   420
gatagatgtt gtgagggagt tagtacacat gactaaagaa agtcttgatg gaggaattat   480
gaaaggacct gcactggagg agacattctc aaattcaagc cttcttcaga tgatatcaat   540
gtctcctgat tctatgagtg tcccttgaat ctttatgtcc cagtcagttt agtttgtcag   600
tcccttcaaa agatgataaa caaccacaat tgtatgtgtg cactataagt ccccagccac   660
tgtacattgg ggaatgcatc caatattctg gttctgacat acttcactaa ggtacaaagc   720
aagtgtattt ggtagctact tcttaataaa tttaatcaac tgctattgtt aatgtgtggg   780
aatcattttc aatacagagg ttttttatg ggtatatata tagttgatga aaatcttcgc   840
gaaaattgta atgtttaatt tattgcat                                      868
```

<210> SEQ ID NO 175
<211> LENGTH: 564
<212> TYPE: DNA
<213> ORGANISM: Glycine max

<400> SEQUENCE: 175

```
aaaaaataat tatacttgac tgatccatat caagccaacc atcaaataag ctcacaagaa    60
aaatcaacca gcaacctcaa ccagacataa agtaatgcc tgaatcacaa gcaaaagtac   120
tcaagatcaa cctgatactc agcaaattca actgccagtt ccttgaacgc tttgtctgct   180
ggttgaagta acttatgggc ttcctgaaat tcgacaagaa tgggatttca tggaagaata   240
tgcaaaaact atcagcacca agtagaacaa ataaaacaat attagatgaa tcatccacaa   300
catattatgc agatgaatat tttacatatt tgctaatata aatcaaatgt caaatattac   360
atctatgaaa gttggtatcc tttccatttt catcactaga tacaatggga cttgcaaata   420
```

```
tttggaatga atctcatccc atgtcaccat ctatcaaggt tgagcttata acaaggaaat      480
gacataaata acaattgata tattttctat taaaaagaaa agaatcaaca attcaacaac      540
caaattgaga caaataccct ttca                                            564
```

<210> SEQ ID NO 176
<211> LENGTH: 780
<212> TYPE: DNA
<213> ORGANISM: Glycine max

<400> SEQUENCE: 176

```
agaacatttg ctgctgcttc tctcagttta tccatcttct ccacagcttg cttacaaatt       60
cctccaacta aattggtagc aagattttca ttgaataaaa aaagctctcg gttgttctta      120
agcatgctat caatcgaagg atatgcaata ggttcaattt catttccatc tgatcttcca      180
gacaaacaaa ctgacttgtc tatcttacag agcatgtatg tacattttc taggccatcc       240 aatgcagcct cacgaaccca agaacctaca tcacctctat tatcaacaga taatcatca       300 agagctttaa ataaacttat catcaccctca ttctttatca gaataaacag ggaaaaatca     360
tcctcaacaa aagaggtagc agtatcttct cttccattaa ttaatgtttc acacactaat      420
gtgagccctt tgacagcatt tactcgtgct tcagcatctc tgtcttcagg gttttcctgc      480
acatgggaaa acattgtgta acacaatcat gaacctaag attgtataat atatagcatt       540
tgcaatgtgg agcacctcaa ttttacaaga gccacaaagc ttcaaaagca catttctcca     600
ttgactggct aataactcat atggcaaaac acctattgcc aatgcagatc ctctccttac      660
agctacattt ggatcagtca acatactgga agtaccttg cttgtcacca tcactttatt      720
acctttatta ttcttgaaag ccatggccaa taattgccac ccggattaaa agtggttttc     780
```

<210> SEQ ID NO 177
<211> LENGTH: 1536
<212> TYPE: DNA
<213> ORGANISM: Glycine max

<400> SEQUENCE: 177

```
ttcggactcg tacccgggca tctctaaatc gacctgcagt gcaaacaatg aaggttatct       60
gttggaaaat tcttcctgtt tcatacatct gtttggatca tgtgaaaagt ttgtgtggaa      120
ctacataatg aagcactagt agcatcctga gatattcttt ggatatagta attagaaata      180
taataataag aaatgctagc tacacacttt cagaaatgct cttttcaagt cacactcttt      240
actattgggt gcattgtttt gtgggtactg ctcccttct agtgggtcat gcataaattt       300
cacccaataa caaaaggtgt gttgctactt gctagccgtt ctcatacata atatatggcc      360
ataaattatg atttcctcat tcacacaact tgtgctactt atatttgatt tcatgaacat      420
tttggattcg acacagtgca acatgcaatt aacaagtatc tgtaattgca ttttctttat     480
tgacagggtt tgttttacc ttcagtcatt tctctagttg ttcctctggt tctgatctcc       540
ttgactaggt agagactctt cttcctacac tgcaaaagtc agctgcaaaa gctgatttga     600
atagtaagat ttagcttaac atataatgtt aggaacttgg caatttctct attgaagtat     660
cctaaaaaat agaagaaaa gaggaaagat ttgaaatat gatgaaagtg ttattactga       720
ataggaggta caataagcct tccgaggaca atttagatga tgctagttct ttacttttt     780 cagtggagtt aatgggaagg aacaaaaggt ctctggatgt ctttgcctct gaaccgattg     840
ctcctcgagg gcaacttgtt ttctcagtga gtttaggagc tttgatttt gtcccagtgt     900
```

| | |
|---|---|
| tcaggtccct cacaggttta cctccgtaca tcggaatgct gctcggactt ggcatgcttt | 960 |
| ggattttcgt tgatgctatc cattatggtg aatctgaaag gcagaagcta aaagtgccac | 1020 |
| atgctctgtc aaggatagac actcaaggag cactattttt cttgggaatt ctattatccg | 1080 |
| ttagcaggta gtgcggaaat atattttaat ttttatgctg tgataagttt tggacaataa | 1140 |
| ccatgtatta atgcattaaa aacaattata aaatacatca agtcatcgac aaaagtgtca | 1200 |
| ttgtcccttt gagtagtagg gcatttgcta tgacttaata ggtctgatat ccacaaagtc | 1260 |
| taacattctg gaaagatgat atattacctt gttttacct ttttcctata ttatgagatg | 1320 |
| catatattgt tcttttgcat gaactgtgat tacatattct tttgctgaca tatctttaaa | 1380 |
| taacctagtt acttatgtta gccggttgta tttgatcaat tttaaccatc atgttcggca | 1440 |
| gcctggaggt agcagggatt cttcgggaaa tagcaaatta ctttgatgca catgtcccaa | 1500 |
| gatgtgaact gattgcaagt gctattggac taatat | 1536 |

<210> SEQ ID NO 178
<211> LENGTH: 727
<212> TYPE: DNA
<213> ORGANISM: Glycine max

<400> SEQUENCE: 178

| | |
|---|---|
| tctacatgtg ggctttacct cagacagggg agccaattca attaatgttc actggtacac | 60 |
| aaggaaacaa atcttcacc atgtgagtct aattctcagc ttcattcact actactctat | 120 |
| tatctattca ctatctactc tgctgaccaa ttttatgcca cgcaggtttg ggatgttaac | 180 |
| ataattgaga cagcagaaga aagattctat gactccaaca tagacgagtt caccaatgcc | 240 |
| attcaagaga atattacggt atttatgca gtagcttct attatcccca atccatggaa | 300 |
| ttacttcaaa gttagagatg cttactccaa attttctgaa acagaaaaca tggtccgatc | 360 |
| aagtactagg atgggaaacc tgcgattcta aggagactgc atgccctgat atgtatgtcc | 420 |
| ctttagttct ttatttatgc aaaagtttat tccttcatca ctgaaatata tgctgttgaa | 480 |
| atattggaac ctgattcatt agttgattta catatgttgt tgaaatataa ttgtttaaca | 540 |
| aacttgggat ttttttcaga tacgcgtctg aaggagttca agcagcctgt caatgggcat | 600 |
| ataaaggtgc tcccgaaggt tcagtgctag aaggtaagat aaaatgattc tgagaagtta | 660 |
| aagagtttca gtcacttttc agattttctg acaatatcat gaaataatac tctgcaggca | 720 |
| tgcaaga | 727 |

<210> SEQ ID NO 179
<211> LENGTH: 535
<212> TYPE: DNA
<213> ORGANISM: Glycine max

<400> SEQUENCE: 179

| | |
|---|---|
| aatattgcat cagatttccc aatgccaata agatcaattg tgactgtaaa agggtgctgt | 60 |
| gctgtagctt gcctctactt ttacaaattt gttgtcttca actttgtcag atctttacaa | 120 |
| aatcatcctg tcgattattc tattgtacta atttgaaaat tccaactctt gttaactgac | 180 |
| ttttatttc cattctattg atgtttcatt gaaaaattg ggaagtccca tgcattaatt | 240 |
| ctaaattaag tgaagttact tattgtagat gattgcgaaa attaggcaga atcatgtgat | 300 |
| tctgattgta cgactataat taggatatgc tattatttcc tttcttagtt acaacagtta | 360 |
| tagggatttt ggttcctgat ttttagctct aaattagtgt acaaaatcag tcttgtaacc | 420 |
| ctatttatac acaccattgc acctttttca aacaatagaa aaatacagtt cattttttcta | 480 | tatggtatca gagctcgatc tgatacttcc ctgaacccag tgccgggcct acaat      535

<210> SEQ ID NO 180
<211> LENGTH: 1201
<212> TYPE: DNA
<213> ORGANISM: Glycine max

<400> SEQUENCE: 180
aagacttgtg ggtagctgca ctttctcatg agttgctgct gaggcaaaaa tccagggcta      60
ggtggattaa aggagatatc atcaagaagt tttggcccac aattaagtct gatatcctgc     120
gcttcttgga cgaattttt gttaatggac attttccaaa aggaagcaat gcctctttta     180
ttgcattgat tcctaaggtg tctgatccgc aatcccttca tgactataga cctatttccc     240
taataggttg tgtctacaag atagtgagca agctattggc caatcgattg aagaaagtta     300
tgcctaccat tttagatgaa cggcaatcag cctttataag cggtaggcac ctgctgcaca     360
gagtcattat tgcaaatgaa gtggtagagg aggctaagag aagtaaaaag tcatgcctag     420
tgttcaaagt cgattatgag aaggcttacg actcagtatc atgggaattt ctgaaataca     480
tgatgaggag gatgaatttc tgccccaaat ggacacaatg gattgcagga tgtttgtctt     540
ctgcatcagt ttcggtcttg gtgaacggga gcccctccgc tgaattcaaa ccccaaagag     600
acctcagaca aggcgatcca ttagcgccac ttctttttaa tatagttgct gagggtctga     660
atggcctaat gagacaagct gtggagaaaa atctattcag agggtactca gtgggaagcc     720
ataatgtgaa cattagcttg ttacaatacc ttgcattgtt gggcaaatgg aaattgagct     780
tattccaaaa ccataaagag ctatgggcta aagtgctgga atcaaagtac ggaggttgga     840
ggagtttaga tgaagcatct cgaggttcta atgattcttc ttggtggagg gatctgaaat     900
tggcactcca tcatccgcaa caagagtttg cttttcacaa tggcttggag tggaagttgg     960
gttgcggtga tcgaataaaa ttttgggagg acaagtggac ttgtggtggg acaactttgg    1020
cagccaaata cccaaggcta tatcttattt cttgccaaca gaatcacctt attcagcaaa    1080
tgggagatca caaagccact ggttgggaat gggatttcca atggaggcga cacttatttg    1140
attgtgaggt atctatggct gacaacttca taaatgaggt ggcagcagtg agggtccagc    1200
t                                                                    1201

<210> SEQ ID NO 181
<211> LENGTH: 681
<212> TYPE: DNA
<213> ORGANISM: Glycine max

<400> SEQUENCE: 181
agaaaacttc tctccgttca tcttctttct actcaatggc atcctcttat caacaaagcc      60
cttccatgaa gcaacaagat gcttccacca acactgatag gagcacccaa atcccagcat     120
ctacagtgac gactgttacg aacagaggac aaagctagct atgctaaact acactaatgg     180
ttaccttcgt aattcttcct tccttcttat ttcattactg ccatatttat aatgatttca     240
acaaaagata atatatggca ttccaaatgg ccataacaga aaggaaaata tcctaataac     300
agagtgagat gaagtttgtt ataacagaaa ggtattttgg ggcaataaca gaattagtgg     360
agtgagtggt ggaatatcct gaagttggtg cccatgctgt ttatcctaca cttgagtcat     420
agcagcgttg ctatcaacga cgcagagaga aaggggcttt gaattaatac ttattcctgg     480
tcatgaagag gaacgcaaaa agtatgcgaa acacaggtac taattccagc ttctcttaac     540

```
aataaaaaca tatgttttga atgtccttat tgtccacagg tggatttaga gtccattaaa    600
agttggttcc caacacatga tgggagaaca ccctataatt cataaagata ctaccattag    660
ggagtgattt tgaaagaaa a                                               681

<210> SEQ ID NO 182
<211> LENGTH: 802
<212> TYPE: DNA
<213> ORGANISM: Glycine max

<400> SEQUENCE: 182
ccaaaagaat atccatacat ctcactgatc catcctttcc catagatgtc accagttatg     60
tttgtcgccc agtgagccct atcttcccgt acttcttcgg tttttgaaag ccacaagggg    120
gcaaaaactc gcaggtcatc tatatgaaag gccaaaagcc caccaacttt gtcacatagt    180
tctgggtgtt tcgtgtgcaa tttagccaaa ctgttgtcac aacctattaa gtacctggag    240
aaataatata gaatatatag caagtttcaa tggtgagcca aggaaagaaa cactaatatg    300
aaatacaaga tataagtact cctttaagag atttaatcaa gtttcataac ttcaagaaaa    360
gctctctagc ttgtgcatta aaaaaaacct attccctgat tcatatcgtc gagtgaatgc    420
attatgacca atgtaaatgt agaaaaaggg ctaaggcatc cagaatttcc atattgttat    480
aaattgttaa tagctaaatg taagctgtat tagtccatta gcctccttcc aaaatatctg    540
aaatggaagt gatgggtaaa tgtctagcgg cttacactac atcactaaaa gaaaggtgt    600 gaaaagaaa caagtaaaaa attagtgaat acccataata tgctgcaaca ggtcttcctt    660
tctctgcacc aagttcccaa agtataattg gccctcggat tatcatgtct gcatccagaa    720
tgacaaccca atcaacattt tttgccttct tactatgttt aagcccagtg tacaacccca    780
gcagggtttg tttattggca gg                                             802

<210> SEQ ID NO 183
<211> LENGTH: 744
<212> TYPE: DNA
<213> ORGANISM: Glycine max

<400> SEQUENCE: 183
agaaaacttc tctccgttca tcttctttct actcaatggc atcctcttat caacaaagcc     60
cttccatgaa gcaacaagat gcttccacca acactgatag gagcacccaa atcccagcat    120
ctacagtgac gactgttacg aacagaggac aaagctagct atgctaaact acactaatgg    180
ttaccttcgt aattcttcct tccttcttat ttcattactg ccatatttat aatgatttca    240
acaaaagata atatatggca ttccaaatgg ccataacaga aaggaaaata tcctaataac    300
agagtgagat gaagtttgtt ataacagaaa ggtattttgg ggcaataaca gaattagtgg    360
agtgagtggt ggaatatcct gaagttggtg cccatgctgt ttatcctaca cttgagtcat    420
agcagcgttg ctatcaacga cgcaaagaga aaggggcttt gaattaatac ttattcctgg    480
tcatgaagag gaacgcaaaa agtatgcgaa acacaggtac taattccagc ttctcttaac    540
aataaaaaca tatgttttga atgtccttat tgtccacagg tggatttaga gtccattaaa    600
agttggttcc caacacatga tgagaacac cctataattc ataaagatac taccattagg    660 agtgatttt tgaaagaaaa agtgggatt ttagaactct tcccccaaaa agaaagaat    720 ggtaaaactt tggaacccaa aaag                                          744

<210> SEQ ID NO 184
<211> LENGTH: 905
```

```
<212> TYPE: DNA
<213> ORGANISM: Glycine max

<400> SEQUENCE: 184
gatcgacctg caggtatgag tggtgggatt gcttatgttc ttgatgtgga tggaaaattc      60
caatctcgat gcaacttgga acttgtagat ctagataagg ttgaagagga agaggacatt     120
cttacactta gaatgttgat tcagcagcat caacgtcaca caaatagtct gctcgccaaa     180
gaagtgcttg atgattttga gaatcttctt cctaaattta tcaaggtgtt ccctagggag     240
tataaacgtg ttcttgcaag tatgaagtct gaggaaacct ccaaagatgc agtggtgcat     300
gctgctaaac atgagcaaga tgatgaagca caagcagtgg agaaggatgc ttttgaagag     360
cttaagaaac tggcgactgc atcattgaat gagaaaccga gtcaggttag ttttttaaat     420
ttttattata ttcttttat ggtacttgta cctttgatgt tcaaaaaaag cgatttttt      480
aaaaacctgt agattgggca ttcacacttc cttaaagtag ttattgagct attgcttttt     540
caaatgaaat tcaatgggcg tgttagatt gaattgaggt gagtttgaaa atggagatct     600
tggttaatta cagggaagaa tgcctagaaa ttctactttg agaccgtttc tcctttatgt     660
gaagatggaa agatcttttt agtaaggaaa gttttttact tcctcttttgc tgtaggtatc     720
ctataaatgt tttaaattaa cctagtagat actgtgctgc atttaatgga tgtttaacga     780
tatcttttgg tggggtgcaa gaatagtata gtttgtttat tgcataaatg tgaataacat     840
acaggggaaa taagcaccta gagaaatttt ttcacagttt atctttgttg atgtctttcg     900
aatat                                                                  905

<210> SEQ ID NO 185
<211> LENGTH: 863
<212> TYPE: DNA
<213> ORGANISM: Glycine max

<400> SEQUENCE: 185
tagcaaagag gaagcctttt ttgattccag gcctggttag actcagattg tgaagatgat      60
ttctatagtg tcaatggtgg taagcatttc cttcaactct ctctcctttt gtactttttt     120
tcttcttctg gtagagcatt taaatttgtt tacttgacca ttttgttata atatagttat     180
gacatggatg atattggtta gaggtgaggc tttgtggctg ataatatgtg atggtaaaca     240
ttgtcttacc attattgaca ttatttataa tatgacaatt tagtttgtca tggacaaatg     300
gatattgtat cataatcaga ctttatgtaa tgcaagttga tgaagaagga ataactcatt     360
ttagaaattt tggatatatt gttttacctt tcttatgtag tttctctttc aactattttc     420
attactctcc ccaaccacct tcagctgtat tgtctacttc attttatgca gactttacac     480
catctagagg gaccacacca gttcaccaca cttttgggac cccttctagg aatagaattc     540
atggctctat ggctgaaaca tccccagaaa agaaaaagaa attgttagag cttttttcgcg     600
aaagtgtcaa agatgaccaa ggtgatgttc atggacacaa agaagtcaag ccaactatac     660
aagatgttat tatgcctaaa tctgcacatt gcactcctta tctctcagag gctaactctg     720
cctgtagtag tgaaaggacc atgagcatga gcgaggatcg ttcatccatt agagagaaat     780
cagtcaagtc tttgcagtgg tgcattccaa gcttgtcttc atgccgaagc tttcgcgaga     840
ggaggccaaa gacgagtcct gca                                              863

<210> SEQ ID NO 186
<211> LENGTH: 593
<212> TYPE: DNA
```

<213> ORGANISM: Glycine max

<400> SEQUENCE: 186

| | | | | | |
|---|---|---|---|---|---|
| tcgacctcgc | ggatttgctt | aacaattgat | attttccca | gtgctagata | tgaaactatt | 60 |
| aagttgcaca | gtgttttgga | gtcttgttat | gtttgtaatc | taatcaggct | atgttttac | 120 |
| tagatatact | acactaatac | tggagcttga | ttattattac | tataataaaa | gcacttggtt | 180 |
| aatttagaat | attttacaaa | atttgttctt | cttttcttcc | tttttccctt | taatttctac | 240 |
| aaaacaactt | cactgaacct | gcccaattgg | agggtgctgc | taatagtaag | tagattatga | 300 |
| attgcttgta | aaaaggcatg | gatgtaacca | tcaaacttgc | tctactttat | tgcagtatgg | 360 |
| ttggtgaagg | aagtgaatgc | ggtttcaatt | tgaactttt | ttggctgtag | actggatcct | 420 |
| tctttcttca | ttctgttta | tgtgactagt | atttgttttc | ctattgcatt | tgtcaaaaaa | 480 |
| atcagtttt | ctatgtttac | cattattatg | caggtgctat | tgtcatgcag | gagatattga | 540 |
| gcgtggtctt | ccgagttttg | agaaccacct | aaggcaggac | aggtctgttc | ccc | 593 |

<210> SEQ ID NO 187
<211> LENGTH: 791
<212> TYPE: DNA
<213> ORGANISM: Glycine max

<400> SEQUENCE: 187

| | | | | | |
|---|---|---|---|---|---|
| tcccattcat | atacctaggg | atgcctatag | gtgttaaccc | tagaaggaag | gtggtgtggg | 60 |
| agcctataat | cagaaaattt | gaagccaaat | tgaacaaatg | gaaccacaga | agcatctcta | 120 |
| tggctggcag | aattaccta | atcaatgctg | tcttgacagc | tttgcccttg | tttatatgt | 180 |
| ctttttcag | ggccccttca | gcagtcatca | agaggctcac | tactatccaa | agacaatttc | 240 |
| tttggggtgg | aaacttggaa | ggaaaaaaga | tagcttggat | ctcatggcag | caagtgtgtg | 300 |
| ctcctagaga | aaagggaggg | ttgggaatca | agatatcaa | ggcttttaat | agagctcttc | 360 |
| tcatcaagtg | gaaatggttg | atgttccagc | aaccagatca | tctatggagc | agaatcctca | 420 |
| cttcaaagta | caggggttgg | agaggtttcg | aagagggtcc | tcctaagcag | attttctcct | 480 |
| cttggtggtc | tgacttaaga | tcaattattc | aacatagtag | catggctgct | gttaataagc | 540 |
| agtttctttg | gaaactgggc | aggggtgatc | aaattttatt | ttgggaagac | tcatgggtgg | 600 |
| gagatggaac | tattcttaga | gacaaatact | cagaattata | tcaaatatca | tctcaaaaac | 660 |
| tacagacagt | ggcaagcatg | gggattttg | gagaaactgg | ctgggagtgg | aaattctcct | 720 |
| ggagaagata | tctctttgac | aatgaattgg | ggggagcctc | agcttttatt | gacaagactg | 780 |
| caggcatgca | g | | | | | 791 |

<210> SEQ ID NO 188
<211> LENGTH: 907
<212> TYPE: DNA
<213> ORGANISM: Glycine max

<400> SEQUENCE: 188

| | | | | | |
|---|---|---|---|---|---|
| aattgcatct | attgccaaat | atgggcatat | agcatcagca | ccaaaaccaa | caagggtgca | 60 |
| gaaatgatgc | actttgcgtg | gctcagcaga | ttcaactatc | aaggcaaccc | tagtgcgctc | 120 |
| aagagtttta | actagatgct | gatgaacagc | accaacagcc | aggagggagc | tcacagagat | 180 |
| gcgtttcttt | gagaaggcta | tcacagatac | aaataaatta | gatggatgtt | cactgtaaaa | 240 |
| agtaactta | accaatacaa | gcaaaacata | gtgcaatacc | tctatcagac | agcacaagag | 300 |
| tggtgtagcc | ttcattaatt | gcatcatgtg | cctctgcaca | catcctgtcc | aaggcttcgt | 360 |

```
ccaaccctct cttaccacat tcctttgaat aagttatgtc tataactttg ctgcgccatc    420
ccctataatt catttttta atggcttcca tttcttcagt ggataaaagg ggacctttta    480
gtgaaaggcg gtgacattgc tcctcagtga tttctgtaag atcaccttct ggaccaacca    540
tacattgcat agaagtgact attttctctc taataggatc aataggaggg tttgtcactt    600
gagcaaacat ttgcttgaaa tactcaaaag tgagttttc tcttttagac atgacagcca    660
atggagtatc atttcccatt gacccaaggg cttctacacc atccttggcc ataggaagta    720
atagcatttc caatgattca actgtatatc tgcatgaata aagcataata taaaatatt    780 tccttcataa atgcagcaga taaaattgag gaaatattaa tgatggtcat tgcatacca    840 aaagctttca gtggaactaa taaaccatga attcccatat tttccatatc tgcatcatca    900
ttggata                                                              907

<210> SEQ ID NO 189
<211> LENGTH: 568
<212> TYPE: DNA
<213> ORGANISM: Glycine max

<400> SEQUENCE: 189
actttcactt catcttcagg catatactcc acaccgccat cagtaaggtc atccaaccag     60
ccttgaagat ctgatccaat ctccttggta atagatggat cggatgctcg aaccacaaac    120
ttgcacagca tggttgtagt ctcatcaccc aagtccacat ttctactcac ttcacttgca    180
ccaaatatca tcatgcccaa gaagccacca tgccaagttt tagcagcata acacatctag    240
tccggtaaag gggggagaaa agtaaagaa ttagtaaatt cattctatgc aactagatgc    300
atataacccc tattgtagtc cttgcttttt agtttttatc ctattttaca atggctaagt    360
ttatcgttct ttaggtacaa atttactgct tctgtccaag tagaaacagt caggtaaatg    420
catacaaggg acagattgaa tagtaccacc actagatttt aataaaacaa ggggattccg    480
ggaatgaaac ataacaactt agtgcatgtt tggattgcca gtagcggcag tccaacttac    540
gttttcaaaa gcatcaactt tgatactt                                       568

<210> SEQ ID NO 190
<211> LENGTH: 826
<212> TYPE: DNA
<213> ORGANISM: Glycine max
<220> FEATURE:
<221> NAME/KEY: unsure
<222> LOCATION: (1)..(826)
<223> OTHER INFORMATION: unsure at all n locations; n = a, t, c, or g

<400> SEQUENCE: 190
aaatgaagtt gatggtgaat atgaagggtc tcactcaact ggttaaggag aaatgtagtt     60
tagcttagaa aactttgtag taagaaatcc cagttccatt cttccttgtt ttgtaataat    120
tttcagctaa catgttttg taggtgtaaa ttgtcattat tcttttatct ttgtaagggg    180
tatcatagca aaatacagaa tacatagtgc tgcttgcttc ttcttctact tttgatgagt    240
tcctgcttgc tggtactggc attattaaca taaatctagt gtttcttttt tttattttat    300
tttataacaa actacagagt aacttgacta tgaattctgc gtaagaagat tatgatgata    360
cataaactaa ctaaaagtct gaaataacaa aaatgaacca gttgccattg gatcatcacc    420
tccaagcaca agaggtaata agaacttgat tcatccaacc aagacacaga gccccatctc    480
tctcctctag agtgtaatgt cctcggtagc ttcgctgaag attttttatt gaacaagtaa    540
```

```
taaacgagtt cagtggatat ggtgcgaatc cagccatagt aaaacgcgat ctccacttct    600
tcagaagctc gtgacgttcc actctttcct gcccttcaca tgctattaag ttgacaactt    660
ctcgagccaa acaatgctgc tccacattaa tcctttcttt gtgctccctc ggcagagcaa    720
catcaattga ttcanaaata gccaagtagt agttcatcgt ctcaacgaaa cggggataa     780 tgggannngt gtggtatgtg attcttgctc aactagtgtc acaatc                   826

<210> SEQ ID NO 191
<211> LENGTH: 969
<212> TYPE: DNA
<213> ORGANISM: Glycine max

<400> SEQUENCE: 191
atctgctgct tatactatgg atgagcatcg gagaattgct tgtgcagaaa ttgagcgttt     60
gaataaagat tctgagaagc agcaagagct gtttacacag aaggtatgcc attgttctgg    120
ttcatttgta atattttttt ggctgatgga aattcatgtg attgtcatta aacttctttc    180
gacaattgac ccttagccat tactatgtat tggtgttact tgcaatgaaa ttatcttgaa    240
tgttcatatt gtcttaaatt gttttttttg tagctgaagg agtctgaaga aaagattggg    300
ggcttaagca aagaaagaga gcaattaatc aggcagagag atgctgctat tcaggaagca    360
aatatgtggc gttctgaact ggcaaaagct agagagcatg atgtgatctt agaagcagct    420
gtagtaagag cagaagaaaa ggttagggtt gcagaagcaa atgctgaaac taggataagg    480
gaggctgttc agagagaatc cgcagcatta aagagaagg aagagcttct tgcatatgtg    540
aatgtactaa aagcccaact tcaaaggtct agcgtcttat tttcttttc ccttgctttt    600 tattttgtta aattagattt gttggctact tctgttttcc cacctaaaca taaagatgga    660
aaaaatatat atcaatacct agtgaaacag ggaaatggaa ggagacttt gatggtttat     720 ttgtcttttt accagtttat tgagtttgaa tatgtatatc agctacgaaa tgtggagctt    780
cataaaacca aagttgacat agcagatatt tttcttttca acaggcaaca cattgataca    840
actcaagttt ttgagaagac agagtcatgc tcagatacaa agcatgttga ccccactgaa    900
gaaaatgtta taaagcatgc ttgagtgttt ctagagccat ccccgtccct gcaggcatgc    960
aagctggcg                                                           969

<210> SEQ ID NO 192
<211> LENGTH: 1269
<212> TYPE: DNA
<213> ORGANISM: Glycine max

<400> SEQUENCE: 192 aaaattttg gagaatatac agagagtaca gcatttgaaa gaccacttac tagtggtgtt      60
gcttatgctt tgaaagttct ccactctgat aggatgcatt tgagaagca gcatgggtgg    120 acaattaaga aaatggaaac tgagaatgag gcattagtcc aagattgtat tcctgaaaaa    180
ttggatccag cacccattca agatgaatat gcaccagtga tatttgctca agaaacagtt    240
tcccatattg tatctattga catgatgtca gggaaggtgt gtcttgctta gcttgctgtc    300
accctagcat gatttacttt ttctaagcaa attgtgggc aatggcttaa actgaaaatt    360
ttacattcct gtcaatgttc ttaccatatt tgttctgcac aagtatgtat aagaaaacta    420
gtgtgaagtc atcagttaga aagacttttt tttctttgta ttttcttat gcaaggttta    480 ggtcatagca ttagatgctt ggagcttttg tatacatgga gtggaatatt agaactggag    540
atcactaaac agtatataat ttactttgaa cagtgaaaat gtgaaagtta aatgtggggt    600
```

```
aaacagaatc aactacatac aagagttta ctcatgaaca tcaataaaat gactctgagc         660
actggttaaa agaaataaga ctaggagtta ctattatcta ttgaattatt tgttaaattt         720
ctcattatct gtctggttaa aagaaaatat tttgttgcat tgttgcacag gaggaccatg         780
agaatatttt gagagcaagg gcatctggaa aggggttct gacatcccct tttaaactac          840
taaagtccaa tcacctgggt gttgtactta catttgctgt ctataacact aatcttcctt         900
tagatgctac accggagcag cgtaccgaag ctactgtggg gtaatcctac atttaactat         960
ctactggtta aaatatgcat tcatttgtg ctctgatcca cctcccctaa gaagaaaaca         1020
attacaaagt gtaatgtgag tgttgttacc tatttattgg caggtatctg ggtgcatctt        1080
atgatgttcc atcactggtg gacaagcttc tgcaccaact tgccagtaaa caaaccattg        1140
ttgtaaatgt ttatgacaca actaatgcat ctgcaccaat cacaatgtat ggtacagatg        1200
ttgctgacac tggcctacta cacataagca gcctagattt tggggatccg ctacgaaaac        1260
atagatgca                                                                1269

<210> SEQ ID NO 193
<211> LENGTH: 1246
<212> TYPE: DNA
<213> ORGANISM: Glycine max

<400> SEQUENCE: 193
aacttcctac acatggaagg ccaatgtggc tccatgagag tgaaggtggg cacactgtcc          60
gttcaaattt tcaaaatcat atgaaatact gtgatgtcgt attcgatcca atgctcaaac         120
tatttgttgg ggtttgattc caataaaaac aatgaggtat ctatttcttc ttttttattt         180
aaaaagacat aaataaaagg aaattatcca acaccaaac ctagtttcaa gggtaaattg          240
ttactgtgcc taggttagga aaatttggta gcatttgaac catttgataa aattttaaat         300
ggaatccagt tgttaaagaa gcttgtgagg aatctgtttt tataatgacc gaaggggggtt        360 aaagaactac ggttaaacaa tgaaactcct ttgtatcctg tgtgtataac atgcataaaa         420
cagtaaggaa atgtttgatt tgattatttt ttattttcat ttttactgaa acgaaaaat          480 ggtgataaaa atgtgtttgg ttgaatttct gaaatatttt tcagtgaaaa taaaaacaga         540
aaataatcag aaaatgataa cagaaacctc atttcggata aaataaaatt acggtaacaa         600
tgaatgtaat tttaaacaaa tctaaaaata caaaagaca agaagttaat atatcataca         660
ttttcagtat ttttatttca tgaaaacaaa aacaagaag ttaaaccaaa catgttttca         720
gaattctttc ttttgaaaat gaaaacaatt ttcaaaaaat aaaaaaaaa tgaaaataca         780 aattaaacac acctaatatt ttcgacattt ttactagtac agtagtacat gtaccagtct         840
gatttatttg tttctatttg gaaaatagtt attgcaggaa atttataaaa taaaataaaa         900
aaatcccgag gaaaggaatg tgtggattga attacaaaga taggactcaa attcggttgt         960
acagtttatt gataactgaa accaatgttt acaaggtttg accagagaaa gctagctcta        1020
tctgtggaag cactaactca tgtcatcatc ttacacaaag caccaccaga gacaactact        1080
tctccactat gaagaacctt tttcttattc tccacaagga acgctccacc tggccaaact        1140
attcacaaga caacattctt ctacaacaac cttgtcatac catactgaac aggtccaacc        1200
tttctatgag cagtggtact aatcccacca tattatgagc cttgac                      1246

<210> SEQ ID NO 194
<211> LENGTH: 671
<212> TYPE: DNA
```

<213> ORGANISM: Glycine max

<400> SEQUENCE: 194

```
atgctttaat attacaacag atggaagttg atgaggttca gaagcctgaa aatgtaactg      60
gaaacatgat atatctttct aagattgaga atcaagaaaa ggaaaaaggc tacgactcta     120
aatcctctat ggtaaatgca cttcaagatg ccaataatag tgaaaaagtg gagcctagaa     180
ctagtggcaa gaaagggatt gtatgcggag ttgaagtagc aatgtctaaa gaaactattg     240
aatgtcagaa ggaagataaa acgaaggtat tcttctaatg ttattgttaa tttttttct      300
tgatgttgta ttattgttct taacttgtga attgtgatca cgttaagctt catttttattt    360
tcattacttt caattttctt agtatgtacc accaatgatg aattaaagat tttgatccaa     420
tgatgatcct tttgatatat ttagtttagt aagttcaaat attttaggct agcattgcaa     480
tgttttacac agttacccac cctttcccgt aaccaataaa aaaaagtgtg atcacattgt     540
tgtacttgtg tatgtctata tccaaagtct ttatatggac accttaatta tgtggggttc     600
catattgtgg agtgactgtg taatgatttt aagactagtt acattggttc ttttgctaaa     660
ttttgatcat c                                                          671
```

<210> SEQ ID NO 195
<211> LENGTH: 1137
<212> TYPE: DNA
<213> ORGANISM: Glycine max

<400> SEQUENCE: 195

```
aactgcttcg gcatgaggaa cgtgacgagg atgttttct ttcttgtctc ccctgagctg       60
tttcagacca tgcttaagtg ccggcaataa agcttccata cactcggcaa cagcattagg     120
gtttccaggc atgttaatga tctgaatttg aacaaatcaa gggccataac ttagccagta     180
agtacaagtc tagaagaaag acagattaga tgtctggatc cagggtgtac tagtagttac     240
agcaataaat gcaagatttt ccttaactac tcatgataca gctccatttt gaagccaagg     300
gcacttgtat accaaatgta aatggatgaa actaaagtaa ctagtaataa acacagatta     360
tcatataaaa aagcttcaga atctagattt gagtttcctg aaaatagtaa ctgtttaact     420
aaaacaacct tactgtaacg gtgaagattg aaaacaatag gtaccttaaa actcaaataa     480
ttaaaatcta acaacagtac aagacatgga cgctttatcc ctcctaatat tcttttaat     540
aaaccagcag ggttttattc atactaactg tgttggtcat ttataatcaa ttttcttatt    600
ttcttataat ttctaaaacg acacttgtta tttcttgtca tcaccctcgt ttaattaatt    660
taagattaaa agggctttct ggctgtttta acaaaccatt ttttctgcat tgaataacag    720
ttaattactt tctcacttgt tactgatagg atattgtaca agtgagagaa taagatattt    780
tcctagaaca gcccataaaa agaaaaagag aaccatgcaa aaccaacaaa gaacatttta    840
aaaataaagt caaccattat tgagatgaaa tattctttta caattaata agtcatttga    900
gagttgagac actaaattca cactcagtaa ttctattttt ttttagataa caagaggaag    960
agaagattga catatttaca ttcttacatg aaatacttac attgttctat aaagaaattt   1020
tctaagatgc ataaaaagct atagtcacaa agcaattcca attataacac taaaatgagt   1080
tttaaagtag atattaatta gcattttgc cttaccaagg ttgatcctct gattcca       1137
```

<210> SEQ ID NO 196
<211> LENGTH: 694
<212> TYPE: DNA
<213> ORGANISM: Glycine max

<400> SEQUENCE: 196

```
aagctccttc tttgggagaa gaaactcttt aacgaagtta aggtatggat cttaaatcac    60
caatctcatt cattccattg cttttcagttt tttccacttt taattttta tctctgtgag   120
gcaatttaat cctgctgcat tcacatcagt tcttgtatat tctattgtaa ccaacctgtg   180
ctgataattt gaaagaaacc aactgatcag aagtctttta tgccataagt aaaacattgt   240
taaccagtgt ttacaggttt ccacattttt tttttccaac gttcatttgt ttgcaggcag   300
aggaaaagat gcgtgttatg catgatagga agtgtcgcaa gctgaagcgt ttggatgata   360
ggggtgctga ttttcataaa gttgattcaa ctcgaacttt ggttaggaat ctgtccacaa   420
aaattagaat ggcaattcag gtggttgata agatttctat gactataaac aagataaggg   480
atgaagaact gtggccacag ctgaaggaat taatccaggg gtatgtgatg ttaaaaacta   540
accattcttg ttatttgttc aagtcctaaa tgtctctctg ttaatgatgg caacactgt    600
atgtaaggat ggatggaaaa ataattccca tatctatgct ccataatcca atccttcaat   660
tcccccaat ccattgaata ttgaattttg aaaa                                694
```

<210> SEQ ID NO 197
<211> LENGTH: 693
<212> TYPE: DNA
<213> ORGANISM: Glycine max

<400> SEQUENCE: 197

```
cgctgcagca gctggaaacc aataaccata taccatactt ggtaagagaa taagtgcgag    60
gtggaaatct agaaaaccaa tgggtgttac tttgagtttt catcatttca tggaaactca   120
ttattcaaaa atagaatcat cgttaatgtg ggttggttga cttggttcaa ttggtagcct   180
taactaaatg gtttccaagt acaaaaccct ggcagaggcc tgtggcatgc attgagcttg   240
cttggaatgg agtaacctct cctcccccaa acttctctca caaaaaaatt aaagaaatta   300
gaatcttcag gagttctagg acaacccttc catcatgcta aaaaactatt ttttgaagta   360
ttgttcaaaa tagtatacca ataccccat gaagctactc aggacagttg taaaagtaat    420
ctaattaaca tgttggaatg cagataaagt cagagaggtg ctgaagcttg atctggagat   480
gaaggatcta gcaaagcagt tgattgctga gcagtctctt cttgtctttg ggagaggata   540
caactatgca acttgctctt gagggagctt tgaaagtaaa ggaagtggct ctaatgcata   600
gtgaagggat acttgctggt gagatgaaac atggtccttt ggcattagtg gatgaaaatc   660
ttccgaatgt tgatctagct acccgtgatg cct                                693
```

<210> SEQ ID NO 198
<211> LENGTH: 738
<212> TYPE: DNA
<213> ORGANISM: Glycine max

<400> SEQUENCE: 198

```
aagaaaacat aaagtatatc ggtttgagca tcacttttt gtagaatgcc cacaataaca     60
gtaaattcag atcaaagtaa aaggctgcac aagactcatc agccagagca aattctgatt   120
tgaattcaac ttttacatga ggagtcagag ccaatgcccg tttatagact gagttgcata   180
cagttacagc acctatgact actttattgt ttaaaatttt agtctcctct agctcaacct   240
aaataatatc ctcaatataa agatgacatt gacagtaaat acaaaagag accaaacaga   300
aaagtcaaga ttgcatacgt gatatactct aaaaaggttg acaacggttc tgtggcttgg   360
```

| | |
|---|---|
| catagcatgt tcttgtaatc atcaaccagc ttaagagtac acttctccac aatcgtggtg | 420 |
| gtatgcaacg gagaaggctc tgcaataggt aacttactca tcagccatca gcatagacca | 480 |
| ataatcttaa ttagatcttg tcaacgagta acaccattg tactaattgt actaatacaa | 540 |
| aagcaacaga aattcttgta aaccttcaat caaattcaat tcaacagaca gagttaaaca | 600 |
| aaacccagac taacaaacaa cagttcactt tcaataatag ttaacattca gacagatata | 660 |
| acatggaaat aaacaagata acacaccact ttttctttg tttcccacaa gtatcatcct | 720 |
| ttggaagaga caatccta | 738 |

<210> SEQ ID NO 199
<211> LENGTH: 610
<212> TYPE: DNA
<213> ORGANISM: Glycine max

<400> SEQUENCE: 199

| | |
|---|---|
| tgcagacata ttgctcatgc catcaaggtt tgagccatgt ggattgaacc aactctatgc | 60 |
| catgaactat ggaacagttc ctgttgtgca tgctgttggt ggactgagag atactgtgca | 120 |
| gccttttgat ccttttaatg agtcaggcct tgggtggaca tttgatagtg cagattaagg | 180 |
| taagttatca catgcattag ggaattgctt aaggacctat agggagtata agaagagcag | 240 |
| ggaagggctt caaggagag gaatgacaca agatcttagt tgggacaatg ctgctcagca | 300 |
| gtatgaggag gtgcttcttg ctgccaaata ccaatggtga acttttggca tttattccat | 360 |
| ctaagaagac ttgtaaaatg gagctgctaa ttcatgttga atacttccag tgtactgatt | 420 |
| gttgtgttag ggaaaagaac tgtgcaagtt gtttaaattt tataggttac agttagagcc | 480 |
| tttttatgg gaagtgggaa ggccaaattt tggtgctgga ttatgtaact gtaatatagt | 540 |
| tgacccttcg tgtcaatgta ttaggatcat accaagtgtt caaccacttc ataatactt | 600 |
| tgccataata | 610 |

<210> SEQ ID NO 200
<211> LENGTH: 915
<212> TYPE: DNA
<213> ORGANISM: Glycine max

<400> SEQUENCE: 200

| | |
|---|---|
| tgattatggt tttcacacag gactgataat ttttctggt ctaaagagga agttacccga | 60 |
| tgactcgagc aaaagtgatg atatggattc caatgacatg atttttttcaa actgtaaaag | 120 |
| aagtcgagct cacgatgcag aggatttgga ggacaatcca ccagggaata cagcatatga | 180 |
| ttgtatggaa accagtagac aaaatagtcc attgtgttca tctatgtccc catgtgcagt | 240 |
| tgaaggttgt ctgtctaagg ggtttgcagg actactcaac ttgttcctat gtgtagtttg | 300 |
| gtagggagag aagggcttcc ttttgatgaa gctcccctct tatagttaaa gaaatacata | 360 |
| gaaggttctt ttgctagttg atatctgttg atgtattcat tttgaatggg ctacaattac | 420 |
| atgatcctag tttctcatta atattattcg tggcgttgta atttttaaca tcatcctggt | 480 |
| gagtgttaaa taactatcca ttgcctttga taaaatgaat agaaatgttg tgttttgctt | 540 |
| ctatgggaaa tttgatccat aattcccatt gtttcaatat gtacttgaa aattgaaaac | 600 |
| taaggacata tggtgaacca gtatattaaa ttttagaact ttgattgaat tttaaaaaaa | 660 |
| attattcccg ggtttacctt atgaaaaaga aaaatggaa aaactgtaaa tggattttat | 720 |
| ttattggtat ttattattt tactgggctc tttctaacaa caacttttag ggacataaat | 780 |
| ctaagtacca aattaccttc ccttattttt ttaaggccct gaacaaccte tgaataaata | 840 |

```
aaagaaattt ttttgccca aattttttga accctcatta aaaaaaaaaa tgtaaatgag      900
actggaaaaa taaaa                                                      915

<210> SEQ ID NO 201
<211> LENGTH: 668
<212> TYPE: DNA
<213> ORGANISM: Glycine max

<400> SEQUENCE: 201
acttttgtac aagctcatca atgtatatca tagtttttga aatcggtaat gaaccaatgc       60
aaaaaatggt ttaaacccgt atttctttag gagatattag gtgaattgga tgattaagga      120
aaaatggaag gaaaaaatat cacaagttta attcctgcta ataaaattaa tatttttaaca     180 actaacattt gctcatataa aaaaccccaa tatttttttaa aatttaatct aaagcatttt     240
taagttaact aaaaacatat ttaataagaa ttaaaatagt tgtaaattat tttattaatt     300
attattaatt actcttataa aacatataat ttaatcatta tatcaatttg caattttta     360 tatcttgatt tcacataatc ttatattaac ttcttgtttt ctttttattt ctagatgtaa     420
acttgttatg aagtgatttt actgggtttt gaccagtttt gattcttcgc caattccttg     480
aacgattttg tagtttattt atatcaaaca ctaaatcaat tcatcagttt tctgggtcaa     540
accaacaaat ttgatctggc atcttataac acaattgttt atggaaaaca catctaatgt     600
gattaaacaa ggacatcacg caacttggca gttaccactt ctttgccttt gctccaatat     660
ttttattt                                                              668

<210> SEQ ID NO 202
<211> LENGTH: 941
<212> TYPE: DNA
<213> ORGANISM: Glycine max

<400> SEQUENCE: 202
caagcttgtt gcctgcagaa aaagcacatg ggatagttgt taatagtttt gaagagttgg       60
aagcagaata tgttgaagag tgtcaaagat ttacggacca tagggtatgg tgtgttgggc      120
ctgtgtcgct gtcaaataag gatgacaagg acaaggctat gagaagtaag agaaactcaa      180
gtgatattga gagtgagtat gtgaagtggc ttgattcatg gcctccgagg tcagtgatt     240 atgtttgcct tggtagccta aaccgtgcaa cgccagagca gttgatagag ctcgggttag      300
gattggaagc gacaaaaagg ccattcattt gggtgcttag aggtgcatat ggaagagagg      360
agatggagaa gtggctgttg gaagatgggt ttgaagagag ggtgaaaggg agagggctt       420 tgatcaaggg ttgggtgcca caagtgttga tcttatcaca tagagcaata ggagcgttca      480
tgacacattg cggatggaat ccacactcg aagggatttg tgctggcgtg ccgttggtaa      540
cttttcctct gtttgctgag cagttcatca atgagaaact tgtacaagtg gtgaagattg      600
gcgtgagtgt gggagctgaa tctgttgttc acttgggtga agaagataag tctcgggttc      660
aggtgaccag agaaaatgtt ctggattcta ttgaaaggta atgggagaat ggccaaaaaa      720 aaaaaaata taggaaaggg ctttaaagta ttccgccatt ggcagggaaa gcaaaaaaa      780 aagtgggttt tttttctcac atggtcctac tcattgggcc atatacctt ggagggttaa     840 ccaagtttaa ccagggttct attttttgtt ttcaacacca attgcttttc tcaagggtca      900
accttaaacc caatttgtct tccgaaagaa ttttttttttt a                        941

<210> SEQ ID NO 203
```

```
<211> LENGTH: 652
<212> TYPE: DNA
<213> ORGANISM: Glycine max

<400> SEQUENCE: 203
taattatatt atttgatttt ttttattcat gacatttatt ttatataatt ttttcttagt    60
ttggtcaaat attatcatcc ttttcattat ctcactaata aggtggattt ttttttgtttg  120
acaaaatttc ttttttcaga ttggtcaaag ctaaagaaga tagaggagtt agatttatcc  180
ggcaacgaat ttaagggacc acttccctcg tcttttgtta acatgacatc tcttcgggag  240
ttggaaattt ctcataatca cttcattgga aatttcgatt ctaacattgc aagccttaca  300
tcacttgaat attttggttt tacagaaaac caatttgaag ttcctgtttc tttctcaaca  360
tttgccaatc attcaaagat caagttgatc gacggtggag gaaacagatt catattggac  420
tcacaacata gtttaccaac ttggattcca aaatttcagt tacaagagct tagtgtgtct  480
tcaacaactg aaactaagtc tcttccactc cccaattttc ttctatacca aaacagttta  540
atcagcctag acttcagtag ttggaagttg aaggagact ttccttattg gttgttggaa   600
aacaacacaa aaatgactga agctctgttt agaaattgct ctttcactgg tg           652

<210> SEQ ID NO 204
<211> LENGTH: 699
<212> TYPE: DNA
<213> ORGANISM: Glycine max

<400> SEQUENCE: 204
tgcatgcctg cagcaatctc agctaaacaa gacaggtttc agcgaaaaac aaatttccat    60
tgctcacaac acacagttcg gcaaaaaagc ttcattaaac tcaaccatgc catcaccact  120
tcattctgtg tagctttgtt ttttcattca tggaaattct cagcatttca accccactc   180
tttgcctccc ccaaaccctc actttaaaat tcccaccaaa ccactccaaa cccacatccc  240
catttctcag aactccattt tcactctacc tatcacgctt cgccgtcata agtttcaaa   300
cttgggcgca ttccgggcga cccagcaacc gccgcaactc cttttggaag aagctcctcc  360
gtgatcgcaa ggtaaactct aatcagattc ccaacgaccc tttctctgtt tcgggcaatg  420
gcgttgaaga gagtggtgtt ggtgatcagg gggttgacaa tgtggttgaa gttgaaaaac  480
caaagtctaa gcttttgcgt gagtctgttt tgtggaataa gttggagaat tgggctgacc  540
agtacaagag ggatgttgag tattggggtg taggatctgg tcctatattc actgtttatg  600
aagattccat tggaggtgtc aagagggtgg ttgtttatgt agaccagatt ctgaaaagaa  660
gcaaggtaaa catggctagg gagatggaga gtgggaata                          699

<210> SEQ ID NO 205
<211> LENGTH: 578
<212> TYPE: DNA
<213> ORGANISM: Glycine max

<400> SEQUENCE: 205
aaacgtgttg aaatgaatat ttgggatctt aacaacttca ctaagatctg gaattccaaa    60
cctgtgagtc tttacttcaa cccttacttt tcatctctgc tattaattgt taacttatct  120
tcctccagtt taccttttgt tggtgcacat tttttagtgc ttgattttac aaatcctttt  180
aacctatgca gccaactaag gataacctcg gtatatttac acctacttgt ttcacatctg  240
ctacatttct tatgaaagat gaccatcgaa aatttgttgc tggcaccaac agccatcagg  300
taaatttaat tggtagattc ttctcattct aaaataagtg aagaaatata attttttatat  360
```

```
ctaataatgc atggaatatt cctctttgat atccttgaaa aaacatgtgc tggagactat    420
tgagaaggat taataagttt ctcttaacct agaattacag agaaatggaa atgatatttt    480
tgagaatttt ttttttgcaaa agaacactca agtacatgtc cttcaagtca catgagatct   540
ttcccatttt attaacaaat ataaaatgag taatatga                            578
```

<210> SEQ ID NO 206
<211> LENGTH: 754
<212> TYPE: DNA
<213> ORGANISM: Glycine max

<400> SEQUENCE: 206

```
gagccagtat aagacatttg tggtgatcgc tctcgaccat gagaagcaga atgcaaagca     60
ttctttgaca aaaattcatc cacaagtgtt tgtaagtaat tgataacatc tttggtccaa    120
acatcagagc gagacagctg aatcttgtca gcagcccag aagaaatacc aacagaacca    180
ggtcgaacct gaaaaagcca atcataatct acaaatatta aaaatataa agcaattcat    240 cataataggt aaatatacca acactgaagc atccctacct gattgaggta agtaaccttg    300
ataaaccagg tggccctaag caatggaaca ttattcctga taagaacctc taaaagtgat    360
gtccttttat aaccatgagg aacatgatca gccaagagc gtaatcgctt gtgctgctga    420
gataaaccct gtaataaaat tttaactgag ttactaaaga tacattgaaa caccaagtaa    480
tgttcaaaaa gtagtattta aggattttac agccacaaca acctgtcagc atcaacaaca    540
aaaaacctaa ggccctattc ggggtggctg agttttctgt tttccgtttt aaaatgctat    600
ttcaaaatgg aaggtgttcg gctaaaatgg ttgcgagttg gattttttatc tgttttaaa    660 acagttgtca ccccatttta taaacaataa aaataggttt tatgttttat tattttaagg    720
ttacttctat ccctacctca acgatctacg ctgc                                754
```

<210> SEQ ID NO 207
<211> LENGTH: 798
<212> TYPE: DNA
<213> ORGANISM: Glycine max
<220> FEATURE:
<221> NAME/KEY: unsure
<222> LOCATION: (1)..(798)
<223> OTHER INFORMATION: unsure at all n locations; n = a, t, c, or g

<400> SEQUENCE: 207

```
tctatctgga gagcagaaaa ttctctccag acatgctcac ctgtggagaa tatattgcat     60
ttggagcccc ttgaggttct ctcaatatat atcattaatt tgattattga tttaagacat    120
ttatggagtg attaactgtg caagaaaata attgtatgtt taactgcctg catacatcgc    180
tatgctaatt ctgtccttca caaatctttt cacaacttgt ttgtgcatga ctctcggaaa    240
agacatgcta acatgcatat ggtgaagata agaaattaaa agaaaattgg aaaaggaaag    300
atgatatagc aatttaaata ttttttaaga tagatgtatg attgctatat cagaaagggg    360
ttagtaaaac tagattgatg tggttgtcct ggttctcttt gatagtaaaa ttttggtatt    420
tcctttgaca catatggtgt atctttgatg gtatgtagta ataccctgga attcagcctt    480
aaattaaagc attttttttat tctctttgga aggtagatat cttccaagga gttacccttc    540
cagatgctcc aagatttgga aaggggggtt ggggggggcgg atgaattgga caggtatgaa    600
ccctactggt ttttccttcc catattaaag cacacctccc ccatgccgag ggggccctt    660 ttatacctac gcttgcgtac gtggcaagtt tattcttgta cgcccctggc cttgtagcac    720
```

```
tgtccaatcc tgggggacat tccagggttg tacagaacga attctcgtcg acgaancgtc    780
ccgtatccgg cctccacc                                                  798
```

<210> SEQ ID NO 208
<211> LENGTH: 1102
<212> TYPE: DNA
<213> ORGANISM: Glycine max

<400> SEQUENCE: 208

```
gtttcgccag cttgcactgc ctgagatgaa gtaattgctg ctgcggtgct gctccggcac     60
cgccttgtgc tggtgcccgg ccaccaggta gagcaaaaga tgtcactcac tctgttcatg    120
aaaaatgggc tcaaggtcaa tgtgcatgag agggatttga gaggggttat cacaagtatt    180
aaaaaggaaa gggaggaaga tgttgatttg agaagtaacg aaagttagtg tggtgttcaa    240
tagatgaagc agagggtgtt ggaggttttt gaatgtggag acaagttcaa atgagaaaaa    300
ttcagaccct ggggctttag cttatagaac aagagaacat aatttccttt taagaaaagg    360
gtatattcag agtattata attcttatga taaattgtgg atggattctt tttccagggt    420
cgtgggatgg atgattgctt tctcaatcca tcgttccttg tagaatccct gcaaatattc    480
attgtattct ttatttcttg tcggttttga tgtttctatt taattttact ggtggtgaga    540
gctaaactca catttcacaa tgttgaatgt tgatgttcat aaaagaatgc cttacgtttt    600
atgaaagtat aatgatcgga tttgactctt ttgtcatata taatggatga tgcttaagtg    660
gtagtggtat actcaaaaac tgcaaaattt agctttacag ttcatctgca tttttggtg    720 aatattcatc tgtgattta gattctgttt ccaggatcct tgcctatgac aatgaaattg    780
aaatgcacaa attgaaccag tagtaaaagt agatatactg atgtcttttg ttaggggaca    840
ttgaatcaga aaactgtgcg accaattttc tcagccatgt atgatgaaga agcagagttg    900
gccatataac atgtatttta actttaagca taagtatgct tgagttatat aagtggacat    960
tatccaccat ctatacagaa accatttaga tcatgggaca agacatttgc aaaaggtgcc   1020
tagttaatcc aagatttcta gataaaatgt aaaggctttc agctatttga tcaaaaactt   1080
tgatggttgc tctcttcgat tt                                            1102
```

<210> SEQ ID NO 209
<211> LENGTH: 697
<212> TYPE: DNA
<213> ORGANISM: Glycine max

<400> SEQUENCE: 209

```
aagtcgcata attttgctat gaacagcttt ttgtcttaga ataatactat tttcaatcct     60
gaatataaaa acaattatc taattcatca agatcaataa agtaatcat attagttaat    120 ttatcataaa ttttaattat attccatgac tatccatgat tacttttcaa agataattt    180 ttcaaccaat aagcttacct tgttttattg atagctcaat aaagacgcca ctttatggg    240 aaaatgaatg taatcattag ggataaaaaa taaatttagc aagaaaaaat tacctttgt    300 ttctgatata tgggatggaa gtggatggaa gtagtataat gatactcatg ccattggatt    360
atctatattg cacatgctaa tttcaagcta ttggaaaatg tggaaaagag atggaattat    420
aggcatgcaa ctttaatcaa ttactatttt ctagggtgac aatgtgttta gctctaaccc    480
gaattgaaac tattaaaaaa atagatcacg atgcatgaag atagaagata tatatatcat    540
ttgagtcttt gtaatgcatg aatgctcata ttttattacc cattaaaaaa tatgggttga    600
gtggtatatt gaattttgat ttattttgtc aatcagatta gattcgaacc aactatttag    660
```

| | |
|---|---|
| tataaaaaat acttttcaaa gcatttcaaa ttttcaa | 697 |

<210> SEQ ID NO 210
<211> LENGTH: 934
<212> TYPE: DNA
<213> ORGANISM: Glycine max

<400> SEQUENCE: 210

| | |
|---|---|
| ttttcacttt atctgtccct agtgtgttgt tgttattgat tggtttatgg tggtattgga | 60 |
| atgttgacca cttgtcttga cttgagtttt gactgtgtat aatggttaac tccggtctct | 120 |
| ctgttgaatg ttgttgagtt attccaagat ttgtgtgctg cttttttttt ttttttttt | 180 |
| ggagtggtta ggtgtaacct ttgtacttat ttttggatgc agacaaggag aaacttggct | 240 |
| aaactggagc tctaccgaaa gtttacaaac acgctcgcgg tgtctgtgtt gctgtccatt | 300 |
| gcgtggattg gctttgaggt agttcttgga aaaaatattt tgatgctcag aaatatgcaa | 360 |
| atttaggaga tttgctctat ctgtaggagt ttccaaacat tttcatttat gtattttat | 420 |
| gcgagttgat gatgctcact aagcgttctt actgtgttca accagctata cttcaatgcc | 480 |
| actgatccat tgagtgaatt gtggcaaatt gcttggatta ttccagcttt ctggtgtctg | 540 |
| ctttcatatg ctctcttggt ggtgatatgc atcctttggg ctccatcacg gaaccctact | 600 |
| aggtacttgt tcttcccatg gtcttggggg gtgaatggta ttttttaga gtttacctgg | 660 |
| tggttttatg cttatgtagt tagccctttt attgaaaggt ggttaatttt ttgaaattaa | 720 |
| actagttttg cattacaaag tgcttggggc tcatttgccg attttttcct tcatgcaact | 780 |
| ggattatgtc cgccacttag gggggggta ttttgcttgt aaatatacac agcaagtgtc | 840 |
| ttcctttaaa aaagaaaaac taccccctt actcttcttt ttattgggta gagagagaaa | 900 |
| aaacataaac aattttatgg ggggtacatt gttt | 934 |

<210> SEQ ID NO 211
<211> LENGTH: 835
<212> TYPE: DNA
<213> ORGANISM: Glycine max

<400> SEQUENCE: 211

| | |
|---|---|
| ttgcatgcct gcagacatcc tttgaaacac gctgtaaatt gagaattgta tactgattat | 60 |
| tgaatcacct ttgcagtctt acatcattgt caatgattgt accataacta tttcatttcc | 120 |
| cattacttgt aataaaagtg gctagtttat ttttgaacat atgtattaat aatagttgca | 180 |
| catgtgtgag atgatgatac atgtgcatcc tgaactcttg gaaaggtgct aaaatgagaa | 240 |
| actatctttt taaatcaggc tactttagtt ggttgaattc tgaataaagt cctctaattt | 300 |
| cttgttatga attgatatat cctctaagaa ataagaatat cgaattaaaa gttgtttaga | 360 |
| gggaaaaaga ttccccagct tttaaatgga cccagtttgt tcaaatatcc catgcaacat | 420 |
| tttactctga ccatttcact tcaacccaag taactaattg catcatagta gcatcaaata | 480 |
| cacaaacaaa aataagttaa aatcacttaa tagaattaga agaaaaaaaa atcaaaatca | 540 |
| agattctaga tattcattgc caaataaaca acgaactttg acagaagctg aaccagaaaa | 600 |
| gactaacaat aactgcttaa aataaaatca tgccagacac tgaattatgt ggtcctattg | 660 |
| attaactgaa agctccttcc gcttatatcg gaccatcact ttccccttca ctcccacaac | 720 |
| catgcattc caatcgatct ctggaaaagg tgacaccaac tccagctcaa aattcctaag | 780 |
| cagatgagtc catattgctt ttatctgcag gtcgactcta gagggaccc gggtt | 835 |

<210> SEQ ID NO 212
<211> LENGTH: 733
<212> TYPE: DNA
<213> ORGANISM: Glycine max
<220> FEATURE:
<221> NAME/KEY: unsure
<222> LOCATION: (1)..(733)
<223> OTHER INFORMATION: unsure at all n locations; n = a, t, c, or g

<400> SEQUENCE: 212

```
agagatcttt catgtcttca acgcccaaag actcgcactg tcacagaaac agaaacagtg      60
aaacactata aaatgctata catctacagc aaataatgaa ctatatggaa atctcctgta     120
ttttacatct atatcaaaca atacacattg aaatagcaac aatgactatt tcaaccattt     180
tttataagaa aaaattttac agataaaagg gagaaaaaaa aaattggaaa ggacaaggta     240
tttcccaaac caaggggagg tgtgggatac tgaatcttca gcttaagccc aataattgag     300
ctgaatagga taaggatatg ttaagagtat tataataaag ggctttagaa gttagttgta     360
tgtacattta taaaaatttt ttttcacaat ctttcttta tcaaaaattg agtgtgatct      420
tttcattcta aatgacagca ttactggaat attattaata ttttttttgg aaaatagatt     480
ttgaaaaact tatatgggct tggcccacat gcctttatgt acataaccta gtaatataaa     540
tatgagagtc actacacatt ggagtggagt ggatcccatt atagtttatt gacacacctc     600
tttatctttc tctctctcta ctctacatgg tatcaagagc caggtagggt ttggtgccat     660
cttcagcagc ctttctccac aaccctaaaa aactgccaaa ggaggccaac caagactgta     720 naggggggg ggg                                                         733
```

<210> SEQ ID NO 213
<211> LENGTH: 834
<212> TYPE: DNA
<213> ORGANISM: Glycine max
<220> FEATURE:
<221> NAME/KEY: unsure
<222> LOCATION: (1)..(834)
<223> OTHER INFORMATION: unsure at all n locations; n = a, t, c, or g

<400> SEQUENCE: 213

```
ctcggtnacc cggggaatcc ctctaggatc gacctgcaga aaacacaaag cctgaactca      60
gccctatcaa ggcagtgcct atgtgtaatg cagctccact gccagatatg ccagcaaaa      120 tgaatgcaat tggtgttagc accaaggctg ctccaaacca tccagttctt gcaatgtgta     180
tcttcctgca ttgtcataca acattagttg attttacgtg taatgtttgg tttcgtgtca     240
tgttctccag aatcatgtat atgtgaagca acgaagggtt gattttacgt tttggatctg     300
aattttgatc cgaatgtaca taaccaatgc atttactttg tttgccaaat ttgactgtat     360
ggtttgagaa ttttttttgca ttcactttgt ttcctgtttt ctgaagttta tacaggaaaa    420
aatggaaaca gaaatgaaa aaagaaaaa ataaaaagtt gttttcact gttcttgtac       480 aaaatcttta aacatttgt ttcctgtttt ctgaagttta tactggaaaa aatggcaaca     540
gaaaatgaaa aaaataaaaa aataaaaagt tgttttcact gttcttgtac aaaatcttta     600
aaacaagaaa caaagtgaaa acagaaaatg ttttctcaaa ccaaacggtg agtgacatgc     660 ttattaccctc tagaataaat cacattatgt tatgtagcaa tcactcttga atctagttga    720
attctatcaa aattctagat aatttttata ctatcaacag agacccttta naatacctgc     780
tnaagaggtc angtgaagct gcaagaaggc gaccgaagaa ggacatgttg agta           834
```

<210> SEQ ID NO 214
<211> LENGTH: 14
<212> TYPE: DNA
<213> ORGANISM: Artificial sequence
<220> FEATURE:
<223> OTHER INFORMATION: Synthetic Probe

<400> SEQUENCE: 214
ctctcgtggc ttca                                                      14

<210> SEQ ID NO 215
<211> LENGTH: 14
<212> TYPE: DNA
<213> ORGANISM: Artificial sequence
<220> FEATURE:
<223> OTHER INFORMATION: Synthetic Probe

<400> SEQUENCE: 215
tccaagcgtg tgcg                                                      14

<210> SEQ ID NO 216
<211> LENGTH: 16
<212> TYPE: DNA
<213> ORGANISM: Artificial sequence
<220> FEATURE:
<223> OTHER INFORMATION: Synthetic Probe

<400> SEQUENCE: 216
ttccccagtt gagttt                                                    16

<210> SEQ ID NO 217
<211> LENGTH: 15
<212> TYPE: DNA
<213> ORGANISM: Artificial sequence
<220> FEATURE:
<223> OTHER INFORMATION: Synthetic Probe

<400> SEQUENCE: 217
ctctcatggc ttcaa                                                     15

<210> SEQ ID NO 218
<211> LENGTH: 15
<212> TYPE: DNA
<213> ORGANISM: Artificial sequence
<220> FEATURE:
<223> OTHER INFORMATION: Synthetic Probe

<400> SEQUENCE: 218
aatgtggtca aagat                                                     15

<210> SEQ ID NO 219
<211> LENGTH: 17
<212> TYPE: DNA
<213> ORGANISM: Artificial sequence
<220> FEATURE:
<223> OTHER INFORMATION: Synthetic Probe

<400> SEQUENCE: 219
cttccccatt tgagttt                                                   17

<210> SEQ ID NO 220
<211> LENGTH: 17
<212> TYPE: DNA
<213> ORGANISM: Artificial sequence
<220> FEATURE:
<223> OTHER INFORMATION: Synthetic Probe

```
<400> SEQUENCE: 220
cacacatgta taaaaga                                                  17

<210> SEQ ID NO 221
<211> LENGTH: 16
<212> TYPE: DNA
<213> ORGANISM: Artificial sequence
<220> FEATURE:
<223> OTHER INFORMATION: Synthetic Probe

<400> SEQUENCE: 221
aatgtgatca aagatg                                                   16

<210> SEQ ID NO 222
<211> LENGTH: 16
<212> TYPE: DNA
<213> ORGANISM: Artificial sequence
<220> FEATURE:
<223> OTHER INFORMATION: Synthetic Probe

<400> SEQUENCE: 222
tgtcacaggt atacca                                                   16

<210> SEQ ID NO 223
<211> LENGTH: 19
<212> TYPE: DNA
<213> ORGANISM: Artificial sequence
<220> FEATURE:
<223> OTHER INFORMATION: Synthetic Probe

<400> SEQUENCE: 223
cacacatgta tataagaag                                                19

<210> SEQ ID NO 224
<211> LENGTH: 14
<212> TYPE: DNA
<213> ORGANISM: Artificial sequence
<220> FEATURE:
<223> OTHER INFORMATION: Synthetic Probe

<400> SEQUENCE: 224
tgatggaaat cttc                                                     14

<210> SEQ ID NO 225
<211> LENGTH: 15
<212> TYPE: DNA
<213> ORGANISM: Artificial sequence
<220> FEATURE:
<223> OTHER INFORMATION: Synthetic Probe

<400> SEQUENCE: 225
ttgtcacggg tatac                                                    15

<210> SEQ ID NO 226
<211> LENGTH: 19
<212> TYPE: DNA
<213> ORGANISM: Artificial sequence
<220> FEATURE:
<223> OTHER INFORMATION: Synthetic Probe

<400> SEQUENCE: 226
atttgaaggg ttttagctt                                                19

<210> SEQ ID NO 227
<211> LENGTH: 15
```

```
<212> TYPE: DNA
<213> ORGANISM: Artificial sequence
<220> FEATURE:
<223> OTHER INFORMATION: Synthetic Probe

<400> SEQUENCE: 227
ctctgatgga atcat                                                        15

<210> SEQ ID NO 228
<211> LENGTH: 16
<212> TYPE: DNA
<213> ORGANISM: Artificial sequence
<220> FEATURE:
<223> OTHER INFORMATION: Synthetic Probe

<400> SEQUENCE: 228
ccagagtttg aatcta                                                       16

<210> SEQ ID NO 229
<211> LENGTH: 16
<212> TYPE: DNA
<213> ORGANISM: Artificial sequence
<220> FEATURE:
<223> OTHER INFORMATION: Synthetic Probe

<400> SEQUENCE: 229
aagggtgtta gcttat                                                       16

<210> SEQ ID NO 230
<211> LENGTH: 16
<212> TYPE: DNA
<213> ORGANISM: Artificial sequence
<220> FEATURE:
<223> OTHER INFORMATION: Synthetic Probe

<400> SEQUENCE: 230
ttcaatggaa tcaatg                                                       16

<210> SEQ ID NO 231
<211> LENGTH: 16
<212> TYPE: DNA
<213> ORGANISM: Artificial sequence
<220> FEATURE:
<223> OTHER INFORMATION: Synthetic Probe

<400> SEQUENCE: 231
ccagagtatg aatcta                                                       16

<210> SEQ ID NO 232
<211> LENGTH: 19
<212> TYPE: DNA
<213> ORGANISM: Artificial sequence
<220> FEATURE:
<223> OTHER INFORMATION: Synthetic Probe

<400> SEQUENCE: 232
tcacctttag ttacaccaa                                                    19

<210> SEQ ID NO 233
<211> LENGTH: 18
<212> TYPE: DNA
<213> ORGANISM: Artificial sequence
<220> FEATURE:
<223> OTHER INFORMATION: Synthetic Probe

<400> SEQUENCE: 233
```

```
tcaatgaaat caatgttg                                                 18

<210> SEQ ID NO 234
<211> LENGTH: 17
<212> TYPE: DNA
<213> ORGANISM: Artificial sequence
<220> FEATURE:
<223> OTHER INFORMATION: Synthetic Probe

<400> SEQUENCE: 234
cataagcagt agaatat                                                  17

<210> SEQ ID NO 235
<211> LENGTH: 18
<212> TYPE: DNA
<213> ORGANISM: Artificial sequence
<220> FEATURE:
<223> OTHER INFORMATION: Synthetic Probe

<400> SEQUENCE: 235
caccttcagt tacaccaa                                                 18

<210> SEQ ID NO 236
<211> LENGTH: 15
<212> TYPE: DNA
<213> ORGANISM: Artificial sequence
<220> FEATURE:
<223> OTHER INFORMATION: Synthetic Probe

<400> SEQUENCE: 236
atgctcgagt tggat                                                    15

<210> SEQ ID NO 237
<211> LENGTH: 17
<212> TYPE: DNA
<213> ORGANISM: Artificial sequence
<220> FEATURE:
<223> OTHER INFORMATION: Synthetic Probe

<400> SEQUENCE: 237
cataagcact agaatat                                                  17

<210> SEQ ID NO 238
<211> LENGTH: 18
<212> TYPE: DNA
<213> ORGANISM: Artificial sequence
<220> FEATURE:
<223> OTHER INFORMATION: Synthetic Probe

<400> SEQUENCE: 238
tagtagcatg acacaaaa                                                 18

<210> SEQ ID NO 239
<211> LENGTH: 16
<212> TYPE: DNA
<213> ORGANISM: Artificial sequence
<220> FEATURE:
<223> OTHER INFORMATION: Synthetic Probe

<400> SEQUENCE: 239
aatgctgagt tggatc                                                   16

<210> SEQ ID NO 240
<211> LENGTH: 16
<212> TYPE: DNA
<213> ORGANISM: Artificial sequence
```

```
<220> FEATURE:
<223> OTHER INFORMATION: Synthetic Probe

<400> SEQUENCE: 240
ttgaaccgtt tcgagc                                                    16

<210> SEQ ID NO 241
<211> LENGTH: 15
<212> TYPE: DNA
<213> ORGANISM: Artificial sequence
<220> FEATURE:
<223> OTHER INFORMATION: Synthetic Probe

<400> SEQUENCE: 241
tagcaggaca caaaa                                                     15

<210> SEQ ID NO 242
<211> LENGTH: 16
<212> TYPE: DNA
<213> ORGANISM: Artificial sequence
<220> FEATURE:
<223> OTHER INFORMATION: Synthetic Probe

<400> SEQUENCE: 242
ctccaaccta tgattg                                                    16

<210> SEQ ID NO 243
<211> LENGTH: 16
<212> TYPE: DNA
<213> ORGANISM: Artificial sequence
<220> FEATURE:
<223> OTHER INFORMATION: Synthetic Probe

<400> SEQUENCE: 243
caattgaacc atttcg                                                    16

<210> SEQ ID NO 244
<211> LENGTH: 16
<212> TYPE: DNA
<213> ORGANISM: Artificial sequence
<220> FEATURE:
<223> OTHER INFORMATION: Synthetic Probe

<400> SEQUENCE: 244
caagccttgt ctaact                                                    16

<210> SEQ ID NO 245
<211> LENGTH: 16
<212> TYPE: DNA
<213> ORGANISM: Artificial sequence
<220> FEATURE:
<223> OTHER INFORMATION: Synthetic Probe

<400> SEQUENCE: 245
agctccaaca tatgat                                                    16

<210> SEQ ID NO 246
<211> LENGTH: 18
<212> TYPE: DNA
<213> ORGANISM: Artificial sequence
<220> FEATURE:
<223> OTHER INFORMATION: Synthetic Probe

<400> SEQUENCE: 246
ttcttgtagg tttcattg                                                  18
```

```
<210> SEQ ID NO 247
<211> LENGTH: 15
<212> TYPE: DNA
<213> ORGANISM: Artificial sequence
<220> FEATURE:
<223> OTHER INFORMATION: Synthetic Probe

<400> SEQUENCE: 247
agcctcgtct aactt                                                    15

<210> SEQ ID NO 248
<211> LENGTH: 14
<212> TYPE: DNA
<213> ORGANISM: Artificial sequence
<220> FEATURE:
<223> OTHER INFORMATION: Synthetic Probe

<400> SEQUENCE: 248
atggctaaaa actg                                                     14

<210> SEQ ID NO 249
<211> LENGTH: 16
<212> TYPE: DNA
<213> ORGANISM: Artificial sequence
<220> FEATURE:
<223> OTHER INFORMATION: Synthetic Probe

<400> SEQUENCE: 249
tcttgttggt ttcatt                                                   16

<210> SEQ ID NO 250
<211> LENGTH: 14
<212> TYPE: DNA
<213> ORGANISM: Artificial sequence
<220> FEATURE:
<223> OTHER INFORMATION: Synthetic Probe

<400> SEQUENCE: 250
catctcgaac tctc                                                     14

<210> SEQ ID NO 251
<211> LENGTH: 13
<212> TYPE: DNA
<213> ORGANISM: Artificial sequence
<220> FEATURE:
<223> OTHER INFORMATION: Synthetic Probe

<400> SEQUENCE: 251
atggctgaaa act                                                      13

<210> SEQ ID NO 252
<211> LENGTH: 15
<212> TYPE: DNA
<213> ORGANISM: Artificial sequence
<220> FEATURE:
<223> OTHER INFORMATION: Synthetic Probe

<400> SEQUENCE: 252
cagtttccat atttc                                                    15

<210> SEQ ID NO 253
<211> LENGTH: 16
<212> TYPE: DNA
<213> ORGANISM: Artificial sequence
<220> FEATURE:
<223> OTHER INFORMATION: Synthetic Probe
```

```
<400> SEQUENCE: 253
tctcgaactc attacc                                                   16

<210> SEQ ID NO 254
<211> LENGTH: 15
<212> TYPE: DNA
<213> ORGANISM: Artificial sequence
<220> FEATURE:
<223> OTHER INFORMATION: Synthetic Probe

<400> SEQUENCE: 254
atccgtcgtc aactt                                                    15

<210> SEQ ID NO 255
<211> LENGTH: 16
<212> TYPE: DNA
<213> ORGANISM: Artificial sequence
<220> FEATURE:
<223> OTHER INFORMATION: Synthetic Probe

<400> SEQUENCE: 255
cagtttccgt atttca                                                   16

<210> SEQ ID NO 256
<211> LENGTH: 22
<212> TYPE: DNA
<213> ORGANISM: Artificial sequence
<220> FEATURE:
<223> OTHER INFORMATION: Synthetic Probe

<400> SEQUENCE: 256
ttttatttaa ttgtcggcct at                                            22

<210> SEQ ID NO 257
<211> LENGTH: 16
<212> TYPE: DNA
<213> ORGANISM: Artificial sequence
<220> FEATURE:
<223> OTHER INFORMATION: Synthetic Probe

<400> SEQUENCE: 257
aatccgtcat caactt                                                   16

<210> SEQ ID NO 258
<211> LENGTH: 18
<212> TYPE: DNA
<213> ORGANISM: Artificial sequence
<220> FEATURE:
<223> OTHER INFORMATION: Synthetic Probe

<400> SEQUENCE: 258
cagtatagtc agtaaaac                                                 18

<210> SEQ ID NO 259
<211> LENGTH: 20
<212> TYPE: DNA
<213> ORGANISM: Artificial sequence
<220> FEATURE:
<223> OTHER INFORMATION: Synthetic Probe

<400> SEQUENCE: 259
cttttattta atggtcggcc                                               20

<210> SEQ ID NO 260
```

```
<211> LENGTH: 18
<212> TYPE: DNA
<213> ORGANISM: Artificial sequence
<220> FEATURE:
<223> OTHER INFORMATION: Synthetic Probe

<400> SEQUENCE: 260
aggagaaatt aagaaaat                                                       18

<210> SEQ ID NO 261
<211> LENGTH: 18
<212> TYPE: DNA
<213> ORGANISM: Artificial sequence
<220> FEATURE:
<223> OTHER INFORMATION: Synthetic Probe

<400> SEQUENCE: 261
cagtatagtc attaaaac                                                       18

<210> SEQ ID NO 262
<211> LENGTH: 17
<212> TYPE: DNA
<213> ORGANISM: Artificial sequence
<220> FEATURE:
<223> OTHER INFORMATION: Synthetic Probe

<400> SEQUENCE: 262
taggtaccat acaaaaa                                                        17

<210> SEQ ID NO 263
<211> LENGTH: 18
<212> TYPE: DNA
<213> ORGANISM: Artificial sequence
<220> FEATURE:
<223> OTHER INFORMATION: Synthetic Probe

<400> SEQUENCE: 263
agaaattagg aaaataac                                                       18

<210> SEQ ID NO 264
<211> LENGTH: 18
<212> TYPE: DNA
<213> ORGANISM: Artificial sequence
<220> FEATURE:
<223> OTHER INFORMATION: Synthetic Probe

<400> SEQUENCE: 264
tgtttgttat gaaattaa                                                       18

<210> SEQ ID NO 265
<211> LENGTH: 17
<212> TYPE: DNA
<213> ORGANISM: Artificial sequence
<220> FEATURE:
<223> OTHER INFORMATION: Synthetic Probe

<400> SEQUENCE: 265
taggtagcat acaaaaa                                                        17

<210> SEQ ID NO 266
<211> LENGTH: 21
<212> TYPE: DNA
<213> ORGANISM: Artificial sequence
<220> FEATURE:
<223> OTHER INFORMATION: Synthetic Probe

<400> SEQUENCE: 266
```
ttgaaaataa caaagataaa t                                       21

<210> SEQ ID NO 267
<211> LENGTH: 17
<212> TYPE: DNA
<213> ORGANISM: Artificial sequence
<220> FEATURE:
<223> OTHER INFORMATION: Synthetic Probe

<400> SEQUENCE: 267
tgtttggtat gaaatta                                            17

<210> SEQ ID NO 268
<211> LENGTH: 20
<212> TYPE: DNA
<213> ORGANISM: Artificial sequence
<220> FEATURE:
<223> OTHER INFORMATION: Synthetic Probe

<400> SEQUENCE: 268
ttgctgattt atgtttatta                                         20

<210> SEQ ID NO 269
<211> LENGTH: 18
<212> TYPE: DNA
<213> ORGANISM: Artificial sequence
<220> FEATURE:
<223> OTHER INFORMATION: Synthetic Probe

<400> SEQUENCE: 269
attgaaaaca acaaagat                                           18

<210> SEQ ID NO 270
<211> LENGTH: 15
<212> TYPE: DNA
<213> ORGANISM: Artificial sequence
<220> FEATURE:
<223> OTHER INFORMATION: Synthetic Probe

<400> SEQUENCE: 270
tgccactaat tatca                                              15

<210> SEQ ID NO 271
<211> LENGTH: 19
<212> TYPE: DNA
<213> ORGANISM: Artificial sequence
<220> FEATURE:
<223> OTHER INFORMATION: Synthetic Probe

<400> SEQUENCE: 271
tgctgatcta tgtttatta                                          19

<210> SEQ ID NO 272
<211> LENGTH: 18
<212> TYPE: DNA
<213> ORGANISM: Artificial sequence
<220> FEATURE:
<223> OTHER INFORMATION: Synthetic Probe

<400> SEQUENCE: 272
tgaaaagcat tagattaa                                           18

<210> SEQ ID NO 273
<211> LENGTH: 13
<212> TYPE: DNA

```
<213> ORGANISM: Artificial sequence
<220> FEATURE:
<223> OTHER INFORMATION: Synthetic Probe

<400> SEQUENCE: 273
tgccacaaat tat                                                          13

<210> SEQ ID NO 274
<211> LENGTH: 15
<212> TYPE: DNA
<213> ORGANISM: Artificial sequence
<220> FEATURE:
<223> OTHER INFORMATION: Synthetic Probe

<400> SEQUENCE: 274
tggttgctca tcata                                                        15

<210> SEQ ID NO 275
<211> LENGTH: 20
<212> TYPE: DNA
<213> ORGANISM: Artificial sequence
<220> FEATURE:
<223> OTHER INFORMATION: Synthetic Probe

<400> SEQUENCE: 275
tgtgaaaaac attagattaa                                                   20

<210> SEQ ID NO 276
<211> LENGTH: 16
<212> TYPE: DNA
<213> ORGANISM: Artificial sequence
<220> FEATURE:
<223> OTHER INFORMATION: Synthetic Probe

<400> SEQUENCE: 276
tcgacaagaa tgggat                                                       16

<210> SEQ ID NO 277
<211> LENGTH: 16
<212> TYPE: DNA
<213> ORGANISM: Artificial sequence
<220> FEATURE:
<223> OTHER INFORMATION: Synthetic Probe

<400> SEQUENCE: 277
aatgtggttg ttcatc                                                       16

<210> SEQ ID NO 278
<211> LENGTH: 18
<212> TYPE: DNA
<213> ORGANISM: Artificial sequence
<220> FEATURE:
<223> OTHER INFORMATION: Synthetic Probe

<400> SEQUENCE: 278
ttattcaatg aaaatctt                                                     18

<210> SEQ ID NO 279
<211> LENGTH: 15
<212> TYPE: DNA
<213> ORGANISM: Artificial sequence
<220> FEATURE:
<223> OTHER INFORMATION: Synthetic Probe

<400> SEQUENCE: 279
ttcgacatgg gattt                                                        15
```

```
<210> SEQ ID NO 280
<211> LENGTH: 15
<212> TYPE: DNA
<213> ORGANISM: Artificial sequence
<220> FEATURE:
<223> OTHER INFORMATION: Synthetic Probe

<400> SEQUENCE: 280
ccggttgtat ttgat                                                    15

<210> SEQ ID NO 281
<211> LENGTH: 16
<212> TYPE: DNA
<213> ORGANISM: Artificial sequence
<220> FEATURE:
<223> OTHER INFORMATION: Synthetic Probe

<400> SEQUENCE: 281
ttattcgatg aaaatc                                                   16

<210> SEQ ID NO 282
<211> LENGTH: 16
<212> TYPE: DNA
<213> ORGANISM: Artificial sequence
<220> FEATURE:
<223> OTHER INFORMATION: Synthetic Probe

<400> SEQUENCE: 282
atggcattgg taaact                                                   16

<210> SEQ ID NO 283
<211> LENGTH: 16
<212> TYPE: DNA
<213> ORGANISM: Artificial sequence
<220> FEATURE:
<223> OTHER INFORMATION: Synthetic Probe

<400> SEQUENCE: 283
ccggttgtat gtgatc                                                   16

<210> SEQ ID NO 284
<211> LENGTH: 19
<212> TYPE: DNA
<213> ORGANISM: Artificial sequence
<220> FEATURE:
<223> OTHER INFORMATION: Synthetic Probe

<400> SEQUENCE: 284
aatagcaaat cctaattat                                                19

<210> SEQ ID NO 285
<211> LENGTH: 16
<212> TYPE: DNA
<213> ORGANISM: Artificial sequence
<220> FEATURE:
<223> OTHER INFORMATION: Synthetic Probe

<400> SEQUENCE: 285
tggcattggt gaactc                                                   16

<210> SEQ ID NO 286
<211> LENGTH: 13
<212> TYPE: DNA
<213> ORGANISM: Artificial sequence
<220> FEATURE:
```

<223> OTHER INFORMATION: Synthetic Probe

<400> SEQUENCE: 286
tgggacagct ttg                                                                                         13

<210> SEQ ID NO 287
<211> LENGTH: 19
<212> TYPE: DNA
<213> ORGANISM: Artificial sequence
<220> FEATURE:
<223> OTHER INFORMATION: Synthetic Probe

<400> SEQUENCE: 287
aggaaataat agcatatcc                                                                                   19

<210> SEQ ID NO 288
<211> LENGTH: 16
<212> TYPE: DNA
<213> ORGANISM: Artificial sequence
<220> FEATURE:
<223> OTHER INFORMATION: Synthetic Probe

<400> SEQUENCE: 288
ttccatggag caacaa                                                                                      16

<210> SEQ ID NO 289
<211> LENGTH: 13
<212> TYPE: DNA
<213> ORGANISM: Artificial sequence
<220> FEATURE:
<223> OTHER INFORMATION: Synthetic Probe

<400> SEQUENCE: 289
tgggacaact ttg                                                                                         13

<210> SEQ ID NO 290
<211> LENGTH: 15
<212> TYPE: DNA
<213> ORGANISM: Artificial sequence
<220> FEATURE:
<223> OTHER INFORMATION: Synthetic Probe

<400> SEQUENCE: 290
tgtgcattag aaaaa                                                                                       15

<210> SEQ ID NO 291
<211> LENGTH: 15
<212> TYPE: DNA
<213> ORGANISM: Artificial sequence
<220> FEATURE:
<223> OTHER INFORMATION: Synthetic Probe

<400> SEQUENCE: 291
ccatgaagca acaag                                                                                       15

<210> SEQ ID NO 292
<211> LENGTH: 16
<212> TYPE: DNA
<213> ORGANISM: Artificial sequence
<220> FEATURE:
<223> OTHER INFORMATION: Synthetic Probe

<400> SEQUENCE: 292
ttccatggag caacaa                                                                                      16

```
<210> SEQ ID NO 293
<211> LENGTH: 15
<212> TYPE: DNA
<213> ORGANISM: Artificial sequence
<220> FEATURE:
<223> OTHER INFORMATION: Synthetic Probe

<400> SEQUENCE: 293
ttgtgcatta aaaaa                                                          15

<210> SEQ ID NO 294
<211> LENGTH: 13
<212> TYPE: DNA
<213> ORGANISM: Artificial sequence
<220> FEATURE:
<223> OTHER INFORMATION: Synthetic Probe

<400> SEQUENCE: 294
ctggcgactg cat                                                            13

<210> SEQ ID NO 295
<211> LENGTH: 15
<212> TYPE: DNA
<213> ORGANISM: Artificial sequence
<220> FEATURE:
<223> OTHER INFORMATION: Synthetic Probe

<400> SEQUENCE: 295
ccatgaagca acaag                                                          15

<210> SEQ ID NO 296
<211> LENGTH: 16
<212> TYPE: DNA
<213> ORGANISM: Artificial sequence
<220> FEATURE:
<223> OTHER INFORMATION: Synthetic Probe

<400> SEQUENCE: 296
tcatggacaa ttggat                                                         16

<210> SEQ ID NO 297
<211> LENGTH: 14
<212> TYPE: DNA
<213> ORGANISM: Artificial sequence
<220> FEATURE:
<223> OTHER INFORMATION: Synthetic Probe

<400> SEQUENCE: 297
ctggcaactg catc                                                           14

<210> SEQ ID NO 298
<211> LENGTH: 16
<212> TYPE: DNA
<213> ORGANISM: Artificial sequence
<220> FEATURE:
<223> OTHER INFORMATION: Synthetic Probe

<400> SEQUENCE: 298
agcacttggt tgattt                                                         16

<210> SEQ ID NO 299
<211> LENGTH: 15
<212> TYPE: DNA
<213> ORGANISM: Artificial sequence
<220> FEATURE:
<223> OTHER INFORMATION: Synthetic Probe
```

```
<400> SEQUENCE: 299
catggacaaa tggat                                               15

<210> SEQ ID NO 300
<211> LENGTH: 15
<212> TYPE: DNA
<213> ORGANISM: Artificial sequence
<220> FEATURE:
<223> OTHER INFORMATION: Synthetic Probe

<400> SEQUENCE: 300
aggtttggaa gaggg                                               15

<210> SEQ ID NO 301
<211> LENGTH: 16
<212> TYPE: DNA
<213> ORGANISM: Artificial sequence
<220> FEATURE:
<223> OTHER INFORMATION: Synthetic Probe

<400> SEQUENCE: 301
cacttggtta atttag                                              16

<210> SEQ ID NO 302
<211> LENGTH: 15
<212> TYPE: DNA
<213> ORGANISM: Artificial sequence
<220> FEATURE:
<223> OTHER INFORMATION: Synthetic Probe

<400> SEQUENCE: 302
tgcactttgc gtggc                                               15

<210> SEQ ID NO 303
<211> LENGTH: 15
<212> TYPE: DNA
<213> ORGANISM: Artificial sequence
<220> FEATURE:
<223> OTHER INFORMATION: Synthetic Probe

<400> SEQUENCE: 303
aggtttcgaa gaggg                                               15

<210> SEQ ID NO 304
<211> LENGTH: 14
<212> TYPE: DNA
<213> ORGANISM: Artificial sequence
<220> FEATURE:
<223> OTHER INFORMATION: Synthetic Probe

<400> SEQUENCE: 304
ccttaccgat ggcg                                                14

<210> SEQ ID NO 305
<211> LENGTH: 14
<212> TYPE: DNA
<213> ORGANISM: Artificial sequence
<220> FEATURE:
<223> OTHER INFORMATION: Synthetic Probe

<400> SEQUENCE: 305
cacttcgcgt ggct                                                14

<210> SEQ ID NO 306
<211> LENGTH: 16
```

```
<212> TYPE: DNA
<213> ORGANISM: Artificial sequence
<220> FEATURE:
<223> OTHER INFORMATION: Synthetic Probe

<400> SEQUENCE: 306
ctggtttagg agaaat                                              16

<210> SEQ ID NO 307
<211> LENGTH: 17
<212> TYPE: DNA
<213> ORGANISM: Artificial sequence
<220> FEATURE:
<223> OTHER INFORMATION: Synthetic Probe

<400> SEQUENCE: 307
ccttactgat ggcggtg                                             17

<210> SEQ ID NO 308
<211> LENGTH: 16
<212> TYPE: DNA
<213> ORGANISM: Artificial sequence
<220> FEATURE:
<223> OTHER INFORMATION: Synthetic Probe

<400> SEQUENCE: 308
ctgcttctaa gatcac                                              16

<210> SEQ ID NO 309
<211> LENGTH: 16
<212> TYPE: DNA
<213> ORGANISM: Artificial sequence
<220> FEATURE:
<223> OTHER INFORMATION: Synthetic Probe

<400> SEQUENCE: 309
ctggttaagg agaaat                                              16

<210> SEQ ID NO 310
<211> LENGTH: 14
<212> TYPE: DNA
<213> ORGANISM: Artificial sequence
<220> FEATURE:
<223> OTHER INFORMATION: Synthetic Probe

<400> SEQUENCE: 310
cagaacaaat atgg                                                14

<210> SEQ ID NO 311
<211> LENGTH: 16
<212> TYPE: DNA
<213> ORGANISM: Artificial sequence
<220> FEATURE:
<223> OTHER INFORMATION: Synthetic Probe

<400> SEQUENCE: 311
ctgcttctag gatcac                                              16

<210> SEQ ID NO 312
<211> LENGTH: 15
<212> TYPE: DNA
<213> ORGANISM: Artificial sequence
<220> FEATURE:
<223> OTHER INFORMATION: Synthetic Probe

<400> SEQUENCE: 312
```
ccagagacga ctact                                                    15

<210> SEQ ID NO 313
<211> LENGTH: 16
<212> TYPE: DNA
<213> ORGANISM: Artificial sequence
<220> FEATURE:
<223> OTHER INFORMATION: Synthetic Probe

<400> SEQUENCE: 313
tgcagaataa atatgg                                                   16

<210> SEQ ID NO 314
<211> LENGTH: 15
<212> TYPE: DNA
<213> ORGANISM: Artificial sequence
<220> FEATURE:
<223> OTHER INFORMATION: Synthetic Probe

<400> SEQUENCE: 314
tggaacccca cataa                                                    15

<210> SEQ ID NO 315
<211> LENGTH: 16
<212> TYPE: DNA
<213> ORGANISM: Artificial sequence
<220> FEATURE:
<223> OTHER INFORMATION: Synthetic Probe

<400> SEQUENCE: 315
cagagacaac tacttc                                                   16

<210> SEQ ID NO 316
<211> LENGTH: 22
<212> TYPE: DNA
<213> ORGANISM: Artificial sequence
<220> FEATURE:
<223> OTHER INFORMATION: Synthetic Probe

<400> SEQUENCE: 316
tgagttttaa agtagatatt aa                                            22

<210> SEQ ID NO 317
<211> LENGTH: 16
<212> TYPE: DNA
<213> ORGANISM: Artificial sequence
<220> FEATURE:
<223> OTHER INFORMATION: Synthetic Probe

<400> SEQUENCE: 317
tggaactcca cataat                                                   16

<210> SEQ ID NO 318
<211> LENGTH: 14
<212> TYPE: DNA
<213> ORGANISM: Artificial sequence
<220> FEATURE:
<223> OTHER INFORMATION: Synthetic Probe

<400> SEQUENCE: 318
cctaaccaaa gttc                                                     14

<210> SEQ ID NO 319
<211> LENGTH: 21
<212> TYPE: DNA
<213> ORGANISM: Artificial sequence

```
<220> FEATURE:
<223> OTHER INFORMATION: Synthetic Probe

<400> SEQUENCE: 319
agttttaaag tagacattaa t                                              21

<210> SEQ ID NO 320
<211> LENGTH: 18
<212> TYPE: DNA
<213> ORGANISM: Artificial sequence
<220> FEATURE:
<223> OTHER INFORMATION: Synthetic Probe

<400> SEQUENCE: 320
ctcacaaaaa aattaaag                                                  18

<210> SEQ ID NO 321
<211> LENGTH: 16
<212> TYPE: DNA
<213> ORGANISM: Artificial sequence
<220> FEATURE:
<223> OTHER INFORMATION: Synthetic Probe

<400> SEQUENCE: 321
tcctaatcaa agttcg                                                    16

<210> SEQ ID NO 322
<211> LENGTH: 15
<212> TYPE: DNA
<213> ORGANISM: Artificial sequence
<220> FEATURE:
<223> OTHER INFORMATION: Synthetic Probe

<400> SEQUENCE: 322
ttctcgacaa tcgtg                                                     15

<210> SEQ ID NO 323
<211> LENGTH: 14
<212> TYPE: DNA
<213> ORGANISM: Artificial sequence
<220> FEATURE:
<223> OTHER INFORMATION: Synthetic Probe

<400> SEQUENCE: 323
ctctcacaaa aatt                                                      14

<210> SEQ ID NO 324
<211> LENGTH: 14
<212> TYPE: DNA
<213> ORGANISM: Artificial sequence
<220> FEATURE:
<223> OTHER INFORMATION: Synthetic Probe

<400> SEQUENCE: 324
ctcctttaaa gccc                                                      14

<210> SEQ ID NO 325
<211> LENGTH: 15
<212> TYPE: DNA
<213> ORGANISM: Artificial sequence
<220> FEATURE:
<223> OTHER INFORMATION: Synthetic Probe

<400> SEQUENCE: 325
ttctccacaa tcgtg                                                     15
```

```
<210> SEQ ID NO 326
<211> LENGTH: 16
<212> TYPE: DNA
<213> ORGANISM: Artificial sequence
<220> FEATURE:
<223> OTHER INFORMATION: Synthetic Probe

<400> SEQUENCE: 326
catgatgcta gtttct                                                     16

<210> SEQ ID NO 327
<211> LENGTH: 15
<212> TYPE: DNA
<213> ORGANISM: Artificial sequence
<220> FEATURE:
<223> OTHER INFORMATION: Synthetic Probe

<400> SEQUENCE: 327
cctttgaagc ccttc                                                      15

<210> SEQ ID NO 328
<211> LENGTH: 19
<212> TYPE: DNA
<213> ORGANISM: Artificial sequence
<220> FEATURE:
<223> OTHER INFORMATION: Synthetic Probe

<400> SEQUENCE: 328
ttgttatgaa gtgatttta                                                  19

<210> SEQ ID NO 329
<211> LENGTH: 16
<212> TYPE: DNA
<213> ORGANISM: Artificial sequence
<220> FEATURE:
<223> OTHER INFORMATION: Synthetic Probe

<400> SEQUENCE: 329
catgatccta gtttct                                                     16

<210> SEQ ID NO 330
<211> LENGTH: 15
<212> TYPE: DNA
<213> ORGANISM: Artificial sequence
<220> FEATURE:
<223> OTHER INFORMATION: Synthetic Probe

<400> SEQUENCE: 330
cactctcaag atcac                                                      15

<210> SEQ ID NO 331
<211> LENGTH: 21
<212> TYPE: DNA
<213> ORGANISM: Artificial sequence
<220> FEATURE:
<223> OTHER INFORMATION: Synthetic Probe

<400> SEQUENCE: 331
agatgtaaac ttgttataaa g                                               21

<210> SEQ ID NO 332
<211> LENGTH: 15
<212> TYPE: DNA
<213> ORGANISM: Artificial sequence
<220> FEATURE:
<223> OTHER INFORMATION: Synthetic Probe
```

```
<400> SEQUENCE: 332
agtggtccct caaat                                                     15

<210> SEQ ID NO 333
<211> LENGTH: 15
<212> TYPE: DNA
<213> ORGANISM: Artificial sequence
<220> FEATURE:
<223> OTHER INFORMATION: Synthetic Probe

<400> SEQUENCE: 333
ctcactctca atatc                                                     15

<210> SEQ ID NO 334
<211> LENGTH: 15
<212> TYPE: DNA
<213> ORGANISM: Artificial sequence
<220> FEATURE:
<223> OTHER INFORMATION: Synthetic Probe

<400> SEQUENCE: 334
cacaacacat agttc                                                     15

<210> SEQ ID NO 335
<211> LENGTH: 15
<212> TYPE: DNA
<213> ORGANISM: Artificial sequence
<220> FEATURE:
<223> OTHER INFORMATION: Synthetic Probe

<400> SEQUENCE: 335
agtggtccct taaat                                                     15

<210> SEQ ID NO 336
<211> LENGTH: 18
<212> TYPE: DNA
<213> ORGANISM: Artificial sequence
<220> FEATURE:
<223> OTHER INFORMATION: Synthetic Probe

<400> SEQUENCE: 336
agtaagggtt gaagtaaa                                                  18

<210> SEQ ID NO 337
<211> LENGTH: 14
<212> TYPE: DNA
<213> ORGANISM: Artificial sequence
<220> FEATURE:
<223> OTHER INFORMATION: Synthetic Probe

<400> SEQUENCE: 337
acacacagtt cggc                                                      14

<210> SEQ ID NO 338
<211> LENGTH: 19
<212> TYPE: DNA
<213> ORGANISM: Artificial sequence
<220> FEATURE:
<223> OTHER INFORMATION: Synthetic Probe

<400> SEQUENCE: 338
catcataatt ggtaaatat                                                 19

<210> SEQ ID NO 339
```

```
<211> LENGTH: 15
<212> TYPE: DNA
<213> ORGANISM: Artificial sequence
<220> FEATURE:
<223> OTHER INFORMATION: Synthetic Probe

<400> SEQUENCE: 339
agggttgaaa gactc                                                    15

<210> SEQ ID NO 340
<211> LENGTH: 19
<212> TYPE: DNA
<213> ORGANISM: Artificial sequence
<220> FEATURE:
<223> OTHER INFORMATION: Synthetic Probe

<400> SEQUENCE: 340
agaaaagggt tagtagaac                                                19

<210> SEQ ID NO 341
<211> LENGTH: 18
<212> TYPE: DNA
<213> ORGANISM: Artificial sequence
<220> FEATURE:
<223> OTHER INFORMATION: Synthetic Probe

<400> SEQUENCE: 341
agcaattcat cataatag                                                 18

<210> SEQ ID NO 342
<211> LENGTH: 15
<212> TYPE: DNA
<213> ORGANISM: Artificial sequence
<220> FEATURE:
<223> OTHER INFORMATION: Synthetic Probe

<400> SEQUENCE: 342
atggatggtg cttaa                                                    15

<210> SEQ ID NO 343
<211> LENGTH: 18
<212> TYPE: DNA
<213> ORGANISM: Artificial sequence
<220> FEATURE:
<223> OTHER INFORMATION: Synthetic Probe

<400> SEQUENCE: 343
aaaagggtta gtaaaact                                                 18

<210> SEQ ID NO 344
<211> LENGTH: 18
<212> TYPE: DNA
<213> ORGANISM: Artificial sequence
<220> FEATURE:
<223> OTHER INFORMATION: Synthetic Probe

<400> SEQUENCE: 344
atgtgcaata tagataat                                                 18

<210> SEQ ID NO 345
<211> LENGTH: 17
<212> TYPE: DNA
<213> ORGANISM: Artificial sequence
<220> FEATURE:
<223> OTHER INFORMATION: Synthetic Probe

<400> SEQUENCE: 345
```
aatggatgat gcttaag                                                  17

<210> SEQ ID NO 346
<211> LENGTH: 16
<212> TYPE: DNA
<213> ORGANISM: Artificial sequence
<220> FEATURE:
<223> OTHER INFORMATION: Synthetic Probe

<400> SEQUENCE: 346
tctgtgttgc tgtcca                                                   16

<210> SEQ ID NO 347
<211> LENGTH: 18
<212> TYPE: DNA
<213> ORGANISM: Artificial sequence
<220> FEATURE:
<223> OTHER INFORMATION: Synthetic Probe

<400> SEQUENCE: 347
tgcaatatag gtaatcca                                                 18

<210> SEQ ID NO 348
<211> LENGTH: 14
<212> TYPE: DNA
<213> ORGANISM: Artificial sequence
<220> FEATURE:
<223> OTHER INFORMATION: Synthetic Probe

<400> SEQUENCE: 348
catgcagcat ttta                                                     14

<210> SEQ ID NO 349
<211> LENGTH: 14
<212> TYPE: DNA
<213> ORGANISM: Artificial sequence
<220> FEATURE:
<223> OTHER INFORMATION: Synthetic Probe

<400> SEQUENCE: 349
tctgtgctgc tgtc                                                     14

<210> SEQ ID NO 350
<211> LENGTH: 14
<212> TYPE: DNA
<213> ORGANISM: Artificial sequence
<220> FEATURE:
<223> OTHER INFORMATION: Synthetic Probe

<400> SEQUENCE: 350
acaaggtatt tccc                                                     14

<210> SEQ ID NO 351
<211> LENGTH: 13
<212> TYPE: DNA
<213> ORGANISM: Artificial sequence
<220> FEATURE:
<223> OTHER INFORMATION: Synthetic Probe

<400> SEQUENCE: 351
cccatgcaac att                                                      13

<210> SEQ ID NO 352
<211> LENGTH: 13
<212> TYPE: DNA

```
<213> ORGANISM: Artificial sequence
<220> FEATURE:
<223> OTHER INFORMATION: Synthetic Probe

<400> SEQUENCE: 352
ccaaggctgc tcc                                                     13

<210> SEQ ID NO 353
<211> LENGTH: 15
<212> TYPE: DNA
<213> ORGANISM: Artificial sequence
<220> FEATURE:
<223> OTHER INFORMATION: Synthetic Probe

<400> SEQUENCE: 353
aggacaagct atttc                                                   15

<210> SEQ ID NO 354
<211> LENGTH: 13
<212> TYPE: DNA
<213> ORGANISM: Artificial sequence
<220> FEATURE:
<223> OTHER INFORMATION: Synthetic Probe

<400> SEQUENCE: 354
ccaaggctgc tcc                                                     13

<210> SEQ ID NO 355
<211> LENGTH: 23
<212> TYPE: DNA
<213> ORGANISM: Artificial sequence
<220> FEATURE:
<223> OTHER INFORMATION: Synthetic Probe

<400> SEQUENCE: 355
acattgcaag aactggatgg ttt                                          23

<210> SEQ ID NO 356
<211> LENGTH: 11
<212> TYPE: DNA
<213> ORGANISM: Glycine max

<400> SEQUENCE: 356
ttcgaagatt t                                                       11
```